(12) United States Patent
Binggeli et al.

(10) Patent No.: US 6,809,110 B2
(45) Date of Patent: Oct. 26, 2004

(54) THIAZOLE DERIVATIVES

(75) Inventors: Alfred Binggeli, Binningen (CH); Uwe Grether, Loerrach (DE); Hans Hilpert, Muenchenstein (CH); Georges Hirth, Huningue (FR); Hans-Peter Maerki, Basel (CH); Markus Meyer, Neuenburg (DE); Peter Mohr, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/650,434

(22) Filed: Aug. 28, 2003

(65) Prior Publication Data

US 2004/0110807 A1 Jun. 10, 2004

(30) Foreign Application Priority Data

Aug. 30, 2002 (EP) ............................................. 02019146

(51) Int. Cl.$^7$ ...................... C07D 277/24; A61K 31/426
(52) U.S. Cl. ........................................ 514/365; 548/204
(58) Field of Search ............................ 548/204; 514/365

(56) References Cited

U.S. PATENT DOCUMENTS

| | | |
|---|---|---|
| 4,011,326 A | 3/1977 | Jensen |
| 5,089,514 A | 2/1992 | Hulin |
| 5,599,826 A | 2/1997 | Mertens et al. |
| 5,856,529 A | 1/1999 | Catt et al. |
| 6,048,883 A * | 4/2000 | Haigh et al. ............. 514/370 |
| 6,121,397 A | 9/2000 | MacLeod et al. |
| 6,291,685 B1 | 9/2001 | Junghans et al. |
| 6,441,185 B2 | 8/2002 | Kühnle et al. |
| 6,498,174 B1 * | 12/2002 | Collins et al. ............. 514/365 |
| 6,710,063 B1 * | 3/2004 | Chao et al. ................ 514/365 |

FOREIGN PATENT DOCUMENTS

| | | |
|---|---|---|
| EP | 0903343 | 3/1999 |
| EP | 1 078 923 | 2/2001 |
| WO | WO 91/19702 | 12/1991 |
| WO | WO 94/01420 | 1/1994 |
| WO | WO 94/13650 | 6/1994 |
| WO | WO 95/17394 | 6/1995 |
| WO | WO 97/25042 | 7/1997 |
| WO | WO 99/08501 | 2/1999 |
| WO | WO 99/10339 | 3/1999 |
| WO | WO 00 08002 | 2/2000 |
| WO | WO 02 16331 | 2/2002 |

OTHER PUBLICATIONS

Keller and Wahli: Trends Endocrin. Metab. (1993); 4:291–296.
MacDougald and Lane: Current Biology vol. 5 pp. 618–621 (1995).
Guerre–Millo, et al.; J Biol Chem2000; 275: 16638–16642.
Balfour, et al.; Drugs 57 (1999) 921–930.
Haigh et. al., Tetrahedron: Asymmetry, 10, pp. 1353–1367.
Gotteland et al., Synlëtt, 9 pp. 931–932 (1995).
Hulin et al., J. Med. Chem., 39, pp. 3897–3907 (1996).
Nicolaou et al., J. Am. Chem. Soc., 122, pp. 3830–3838 (2000).
Nichols et al., Anal. Biochem., 257, pp. 112–119 (1998).
Einsiedel et. al., Bioorg. Med. Chem. Lett., 10, pp. 2041–2044 (2000).
Goto et al., Chem. Pharm. Bull., 19, pp. 2050–2057 (1971).
Reichstein et al., Helvetica Chimica Acta, 16, pp. 121–129 (1933).
Diels et al., chem.. Ber., 48, pp. 897–905 (1915).
Wightman et al., J. Org. chem.., 43, pp. 2167–2170 (1978).
Musser et al., J. Med. Chem. 30, pp. 62–67 (1987).
Rahman et al., J. Chem. Soc. Perkin Trans. 1, 12, pp. 2973–2977 (1983).
Kelly et al., J. Am. Chem. Soc., 110, pp. 6471–6480 (1988).
Kneen et al., Synthetic Communications, 16, pp. 1635–1640 (1986).
Kim et al., Can. J. Chem., 60, pp. 2093–2098 (1982).
Párkányi et al., Monatsh. Chem., 123, pp. 637–645 (1992).
STN International ® CAPLUS Database, Accession No. 2000; 117035; Collins et al., WO 2000008002, abstract.
Malamas, MS et al, Eur. J. Med. Chem. vol. 36, No. 1 (2001) pp. 31–42.
Hulin, B. et al., Current Pharmaceutical Design, vol. 2 (1990) pp. 85–102.
Oplinger, et. al., ACS National Meeting, San Diego, Apr. 1–5, 2001, Poster 238, Division of Medicinal Chemistry, Section C.

* cited by examiner

Primary Examiner—Fiona T. Powers
(74) Attorney, Agent, or Firm—George W. Johnston; Dennis P. Tramaloni; Eileen M. Ebel

(57) ABSTRACT

The present invention provides compounds of formula (I)

wherein $R^1$ to $R^{10}$, X, Y and n are indicated in the specification, and pharmaceutically acceptable salts and esters thereof. The compounds are useful for the treatment of non-insulin dependent diabetes mellitus.

27 Claims, No Drawings

THIAZOLE DERIVATIVES

BACKGROUND OF THE INVENTION

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ (also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80–90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease syndrome. Among the comorbidities associated with T2D are for example insulin resistance, dyslipidemia, hypertension, endothelial dysfunction and inflammatory atherosclerosis.

Current first line treatment for diabetes generally involves low fat—and glucose—diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives that had been approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i. e. such compounds should improve the lipid profile in addition to the normalization of glucose- and insulin-levels (Keller and Wahli: Trends Endocrin. Metab. 1993; 4:291–296, Macdonald and Lane: Current Biology Vol.5 pp.618–621 (1995)). Recent observations suggest furthermore that there is an independent PPARα mediated effect on insulin-sensitzation that could result secondary to the reduction in lipids (Guerre-Millo et al; J Biol Chem2000; 275: 16638–16642). Consequently, the incorporation of PPARα activity into PPARγ agonists is expected to give rise to more efficacious drugs for the treatment and/or prevention of diabetes.

SUMMARY OF THE INVENTION

The present invention provides compounds of the formula (I)

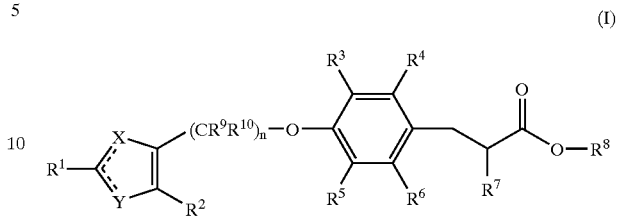

wherein
X is N and Y is S; or
X is S and Y is N;
$R^1$ is aryl or heteroaryl;
$R^2$ is hydrogen, lower-alkyl or fluoro-lower-alkyl;
$R^3$, $R^4$, $R^5$ and $R^6$ independently from each other are selected from hydrogen, hydroxy, lower-alkenyl, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, and lower-alkoxy-lower-alkoxy, wherein at least one of $R^3$, $R^4$, $R^5$ and $R^6$ is not hydrogen, or
$R^3$ and $R^4$ are bonded to each other to form a ring together with the carbon atoms to which they are attached, and $R^3$ and $R^4$ together are —CH=CH—S—, —S—CH=CH—, —CH—CH—O—, —O—CH=CH—, —CH—SH—CH=CH—, —(CH$_2$)$_{3-5}$—, —O—(CH$_2$)$_{2-3}$— or —(CH$_2$)$_{2-3}$—O—, and $R^5$ and $R^6$ are as defined above;
$R^7$ is lower-alkyl, lower-alkoxy, lower-alkenyloxy, aryloxy or aryl-lower-alkoxy,
$R^8$ is hydrogen or lower-alkyl;
$R^9$ and $R^{10}$ independently from each other are hydrogen, lower-alkyl, lower-alkenyl, cycloalkyl, phenyl or [1,3] dioxan-2-ethyl;
n is 1, 2 or 3;
and pharmaceutically acceptable salts and pharmaceutically acceptable esters thereof.

DETAILED DESCRIPTION OF THE INVENTION

The compounds of the present invention exceed the compounds known in the art, inasmuch as they bind to and activate both, PPARα and PPARγ, simultaneously and very efficiently. Therefore, these compounds combine the antiglycemic effect of PPARγ activation with the antidyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential compared to the compounds already known in the art.

The compounds of the present invention further exhibit improved pharmacological properties compared to known compounds.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine.

The term "protecting group" refers to groups such as e.g., acyl, alkoxycarbonyl, aryloxycarbonyl, silyl, or imine-derivatives, which are used to temporarily block the reactivity of functional groups. Well known protecting groups are e.g., t-butyloxycarbonyl, benzyloxycarbonyl, fluorenyl-methyloxycarbonyl or diphenylmethylene which can be used for the protection of amino groups, or lower-alkyl-, β-trimethylsilylethyl- and β-trichloroethyl-esters, which can be used for the protection of carboxy groups.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalyl" refers to a monovalent carbocyclic radical of 3 to 10 carbon atom(s), preferably 3 to 6 carbon atoms, such as cyclopropyl, cyclobutyl, cyclopentyl, or cyclohexyl.

The term "fluoro-lower-alkyl" refers to lower alkyl groups which are mono- or multiply substituted with fluorine. Examples of fluoro-lower-alkyl groups are e.g. $CF_3$, $CF_3CH_2$ and $(CF_3)_2CH$.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy.

The term "fluoro-lower-alkoxy" refers to the group R"—O—, wherein R" is fluoro-lower-alkyl. Examples of fluoro-lower-alkoxy groups are e.g. $CF_3$—O, $CF_3CH_2$—O and $(CF_3)_2CH$—O.

The term "lower-alkenyl", alone or in combination signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower-alkenyloxy" means a group R"—O—, wherein R" is lower-alkenyl. Examples of lower-alkenyloxy groups are butenyloxy, particularly but-3-enyloxy.

The term "aryl" relates to the phenyl or naphthyl group, preferably the phenyl group, which can optionally be mono- or multiply-substituted, particularly mono- or di-substituted by a group or groups selected from halogen, hydroxy, CN, $CF_3$, $NO_2$, $NH_2$, N(H, lower-alkyl), N(lower-alkyl)$_2$, carboxy, aminocarbonyl, lower-alkyl, lower-alkoxy, aryl and aryloxy. Preferred substituents are halogen, $CF_3$, lower-alkyl and/or lower-alkoxy.

The term "heteroaryl" refers to an aromatic 5- or 6-membered ring which can comprise 1, 2 or 3 atoms selected from nitrogen, oxygen and sulphur, such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen and sulphur, such as e.g., indole or quinoline, or partially hydrogenated bicyclic aromatic groups such as e.g., indolinyl. A heteroaryl group may have a substitution pattern as described earlier in connection with the term "aryl". Preferred heteroaryl groups are e.g., thienyl and furyl, which can optionally be substituted as described above, preferably with a group selected from halogen, $CF_3$, lower-alkyl and lower-alkoxy.

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The present invention provides compounds of formula (I)

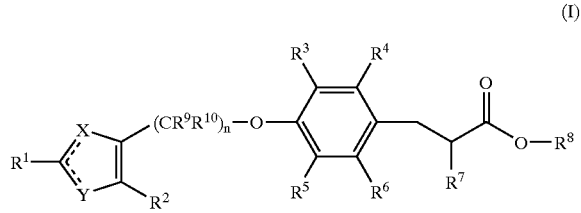

(I)

wherein
X is N and Y is S; or
X is S and Y is N;
$R^1$ is aryl or heteroaryl;
$R^2$ is hydrogen, lower-alkyl or fluoro-lower-alkyl;
$R^3$, $R^4$, $R^5$ and $R^6$ independently from each other are selected from hydrogen, hydroxy, lower-alkenyl, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, and lower-alkoxy-lower-alkoxy, wherein at least one of $R^3$, $R^4$, $R^5$ and $R^6$ is not hydrogen, or $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH—, —(CH$_2$)$_{3-5}$—, —O—(CH$_2$)$_{2-3}$— or —(CH$_2$)$_{2-3}$—O—, and $R^5$ and $R^6$ are as defined above;

$R^7$ is lower-alkyl, lower-alkoxy, lower-alkenyloxy, aryloxy or aryl-lower-alkoxy;

$R^8$ is hydrogen or lower-alkyl;

$R^9$ and $R^{10}$ independently from each other are hydrogen, lower-alkyl, lower-alkenyl, cycloalkyl, phenyl or [1,3] dioxan-2-ethyl;

n is 1, 2 or 3;

and pharmaceutically acceptable salts and pharmaceutically acceptable esters thereof.

Preferably, $R^7$ is lower-alkoxy, lower-alkenyloxy, aryloxy or aryl-lower-alkoxy, $R^9$ is hydrogen and $R^{10}$ is hydrogen. Such compounds are characterized by formula (Ia)

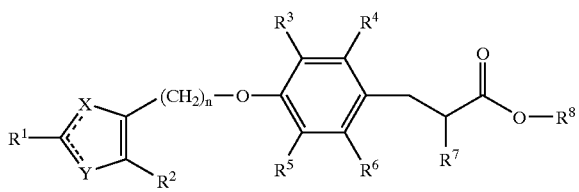

(Ia)

wherein

X is N and Y is S; or
X is S and Y is N;

$R^1$ is aryl or heteroaryl;

$R^2$ is hydrogen, lower-alkyl or fluoro-lower-alkyl;

$R^3$, $R^4$, $R^5$ and $R^6$ independently from each other are selected from hydrogen, hydroxy, lower-alkenyl, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, and lower-alkoxy-lower-alkoxy, wherein at least one of $R^3$, $R^4$, $R^5$ and $R^6$ is not hydrogen, or $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH—, —(CH$_2$)$_{3-5}$—, —O—(CH$_2$)$_{2-3}$— or —(CH$_2$)$_{2-3}$—O—, and $R^5$ and $R^6$ are as defined above;

$R^7$ is lower-alkoxy, lower-alkenyloxy, aryloxy or aryl-lower-alkoxy;

$R^8$ is hydrogen or lower-alkyl;

n is 1, 2 or 3;

and pharmaceutically acceptable salts and/or pharmaceutically acceptable esters thereof.

Preferred compounds of the of the present invention are those, in which X is N and Y is S. Compounds, in which X is S and Y is N are also preferred. Compounds of formula (I) as defined above, in which $R^1$ is aryl are also preferred, with those compounds wherein $R^1$ is phenyl optionally substituted with 1 to 3 substituents independently selected from the group consisting of lower-alkyl, lower-alkoxy, halogen and CF$_3$ being more preferred, and with those compounds wherein $R^1$ is phenyl, 4-isopropyl-phenyl, 4-chloro-phenyl, 4-trifluoromethyl-phenyl or 3,5-dimethoxy-phenyl being particularly preferred. Compounds, wherein $R^1$ is phenyl, 4-isopropyl-phenyl, 4-chloro-phenyl or 4-trifluoromethyl-phenyl are also particularly preferred.

Furthermore, compounds as defined above in which $R^2$ is lower-alkyl or hydrogen are preferred, with methyl or hydrogen being particularly preferred. Methyl and hydrogen individually constitute separate preferred embodiments. Other preferred compounds are those, in which $R^5$ and $R^6$ are hydrogen.

Compounds of formula (I), wherein $R^3$, $R^4$, $R^5$ and $R^6$ independently from each other are hydrogen, halogen, lower-alkyl or lower-alkoxy, wherein one or two of $R^3$, $R^4$, $R^5$ and $R^6$ are not hydrogen, or $R^3$ and $R^4$ are bonded to each other to form a ring together with the carbon atoms to which they are attached, and $R^3$ and $R^4$ together are —CH=CH—S—, —S—CH=CH—, —(CH$_2$)$_{3-5}$—, —CH=CH—CH=CH—, —O—CH=CH— or —O—(CH$_2$)$_{2-3}$—, and $R^5$ and $R^6$ are hydrogen are preferred. Furthermore, compounds as defined above, wherein one or two of $R^3$, $R^4$, $R^5$ and $R^6$ independently from each other are halogen, lower-alkyl or lower-alkoxy, and the others are hydrogen are also preferred. Compounds as defined above, wherein $R^4$ is methyl and $R^3$, $R^5$ and $R^6$ are hydrogen are also preferred.

Compounds of formula (I), wherein $R^3$ and $R^4$ independently from each other are hydrogen, lower-alkyl, lower-alkoxy or halogen, wherein one of $R^3$ and $R^4$ is not hydrogen and $R^5$ and $R^6$ are hydrogen, or $R^3$ and $R^4$ are bonded to each other to form a ring together with the carbon atoms to which they are attached, and $R^3$ and $R^4$ together are —CH=CH—S—, —S—CH=CH—, —(CH$_2$)$_{3-5}$—, and $R^5$ and $R^6$ are hydrogen also relate to a preferred embodiment of the present invention. Such compounds, wherein $R^5$ and $R^6$ are hydrogen; and $R^3$ is lower-alkyl or halogen and $R^4$ is hydrogen, or $R^3$ is hydrogen and $R^4$ is lower-alkyl or halogen are particularly preferred.

Further preferred compounds of formula (I) as described above are those, wherein $R^5$ and $R^6$ are hydrogen; and $R^3$ and $R^4$ are bonded to each other to form a ring together with the carbon atoms to which they are attached, and $R^3$ and $R^4$ together are —CH=CH—S—, —S—CH=CH—, —(CH$_2$)$_{3-5}$—, —CH=CH—CH=CH—, —O—CH=CH—, or —O—(CH$_2$)$_{2-3}$—. Those compounds, wherein $R^5$ and $R^6$ are hydrogen; and $R^3$ and $R^4$ are bonded to each other to form a ring together with the carbon atoms to which they are attached, and $R^3$ and $R^4$ together are —CH=CH—S—, —(CH$_2$)$_{3-5}$—, or —CH=CH—CH=CH—, are particularly preferred.

Other preferred compounds of the present invention are those, wherein $R^5$ and $R^6$ are hydrogen; and $R^3$ and $R^4$ are bonded to each other to form a ring together with the carbon atoms to which they are attached, and $R^3$ and $R^4$ together are —CH=CH—S—. Such compounds consequently comprise the following moiety

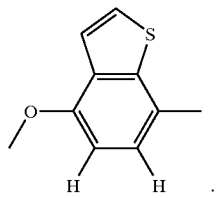

Further preferred compounds of formula (I) are those, wherein $R^7$ is lower-alkyl or lower-alkoxy, particularly lower-alkoxy, more particularly ethoxy. Compounds, in which $R^7$ is ethyl, ethoxy or isopropoxy are also preferred. Also preferred are compounds of formula (I), wherein $R^8$ is hydrogen.

Also preferred are compounds of formula (I), wherein n is 1. Further preferred are compounds of formula (I), wherein n is 2. Other preferred compounds are those, wherein n is 3.

In another preferred embodiment of the present invention, $R^9$ and $R^{10}$ independently from each other are hydrogen, lower-alkyl or cycloalkyl. Preferably, $R^9$ and $R^{10}$ are hydrogen.

The pharmaceutically acceptable salts of the compound of formula (I) and the pharmaceutically acceptable esters of the compounds of formula (I) individually constitute preferred embodiments of the present invention. Particularly preferred are compounds of formula (I).

Preferred compounds of general formula (I) are those selected from the group consisting of

[rac]-2-Ethoxy-3-{4-[2-(5-methyl-2-phenyl-thiazol-4-yl)-ethoxy]-benzo[b]thiophen-7-yl}-propionic acid,

[rac]-2-Ethoxy-3-{4-[2-(5-methyl-2-phenyl-thiazol-4-yl)-ethoxy]-5,6,7,8-tetrahydro-naphthalen-1-yl}-propionic acid,

[rac]-2-Ethoxy-3-{7-[2-(5-methyl-2-phenyl-thiazol-4-yl)-ethoxy]-benzo[b]thiophen-4-yl}-propionic acid,

[rac]-3-{4-[2-(4-tert-Butyl-phenyl)-thiazol-4-ylmethoxy]-3-methyl-phenyl}-2-ethoxy-propionic acid,

[rac]-2-Ethoxy-3-{4-[2-(4-isopropyl-phenyl)-thiazol-4-ylmethoxy]-3-methyl-phenyl}-propionic acid,

[rac]-2-Ethoxy-3-{3-methyl-[2-(4-trifluoromethyl-phenyl)-thiazol-4-ylmethoxy]-phenyl}-propionic acid,

[rac]-3-{4-[2-(4-tert-Butyl-phenyl)-thiazol-4-ylmethoxy]-3-fluoro-phenyl}-2-ethoxy-propionic acid,

[rac]-2-Ethoxy-3-{3-fluoro-4-[2-(4-trifluoromethyl-phenyl)-thiazol-4-ylmethoxy]-phenyl}-propionic acid,

[rac]-2-Ethoxy-3-{3-fluoro-4-[2-(4-isopropyl-phenyl)-thiazol-4-ylmethoxy]-phenyl}-propionic acid,

[rac]-2-Ethoxy-3-(2-methyl-4-{2-[5-methyl-2-(4-trifluoromethyl-phenyl)-thiazol-4-yl]-ethoxy}-phenyl)-propionic acid,

[rac]-2-Ethoxy-3-{2-methyl-4-[2-(5-methyl-2-phenyl-thiazol-4-yl)-ethoxy]-phenyl}-propionic acid,

[rac]-3-(4-{2-[2-(4-tert-Butyl-phenyl)-5-methyl-thiazol-4-yl]-ethoxy}-2-methyl-phenyl)-2-ethoxy-propionic acid,

[rac]-2-Ethoxy-3-(4-{2-[2-(4-isopropyl-phenyl)-thiazol-4-yl]-ethoxy}-2-methyl-phenyl)-propionic acid,

[rac]-3-{4-[2-(4-Chloro-phenyl)-thiazol-4-ylmethoxy]-2-methyl-phenyl}-2-ethoxy-propionic acid,

[rac]-3-{4-[2-(4-tert-Butyl-phenyl)-thiazol-4-ylmethoxy]-2-methyl-phenyl}-2-ethoxy-propionic acid,

[rac]-2-Ethoxy-3-{4-[2-(4-isopropyl-phenyl)-thiazol-4-ylmethoxy]-2-methyl-phenyl}-propionic acid, (2S)-3-{4-[2-(3-Chloro-4-fluoro-phenyl)-thiazol-4-ylmethoxy]-2-methyl-phenyl}-2-ethoxy-propionic acid, (2S)-2-Ethoxy-3-{2-methyl-4-[2-(4-trifluoromethyl-phenyl)-thiazol-4-ylmethoxy]-phenyl}-propionic acid, (2S)-3-{4-[2-(3-Chloro-phenyl)-thiazol-4-ylmethoxy]-2-methyl-phenyl}-2-ethoxy-propionic acid, (2S)-3-{4-[2-(4-Chloro-phenyl)-thiazol-4-ylmethoxy]-2-methyl-phenyl}-2-ethoxy-propionic acid, (2S)-3-{4-[2-(4-Chloro-phenyl)-thiazol-4-ylmethoxy]-2-methoxy-phenyl}-2-ethoxy-propionic acid, (2S)-3-{2-Chloro-4-[2-(4-chloro-phenyl)-thiazol-4-ylmethoxy]-phenyl}-2-ethoxy-propionic acid, (2S)-3-{4-[2-(4-Chloro-phenyl)-thiazol-4-ylmethoxy]-2-ethyl-phenyl}-2-ethoxy-propionic acid,

[rac]-2-Ethoxy-3-{3-fluoro-4-[2-(5-methyl-2-phenyl-thiazol-4-yl)-ethoxy]-phenyl}-propionic acid,

[rac]-2-Ethoxy-3-(3-fluoro-4-{2-[2-(4-trifluoromethyl-phenyl)-thiazol-4-yl]-ethoxy}-phenyl)-propionic acid,

[rac]-2-Ethoxy-3-{3-fluoro-4-[2-(2-phenyl-thiazol-4-yl)-ethoxy]-phenyl}-propionic acid,

[rac]-2-Ethoxy-3-[3-fluoro-4-(4-methyl-2-phenyl-thiazol-5-ylmethoxy)-phenyl]-propionic acid,

[rac]-2-Ethoxy-3-{3-fluoro-4-[3-(2-phenyl-thiazol-4-yl)-propoxy]-phenyl}-propionic acid,

[rac]-2-Ethoxy-3-(3-fluoro-4-{2-[5-methyl-2-(4-trifluoromethyl-phenyl)-thiazol-4-yl]-ethoxy}-phenyl)-propionic acid,

[rac]-3-(4-{2-[2-(4-tert-Butyl-phenyl)-thiazol-4-yl]-ethoxy}-3-fluoro-phenyl)-2-ethoxy-propionic acid,

[rac]-2-Ethoxy-3-[2-methyl-4-(2-phenyl-thiazol-4-ylmethoxy)-phenyl]-propionic acid,

[rac]-3-{4-[2-(2-Chloro-phenyl)-thiazol-4-ylmethoxy]-2-methyl-phenyl}-2-ethoxy-propionic acid,

[rac]-3-{4-[2-(4-tert-Butyl-phenyl)-4-methyl-thiazol-5-ylmethoxy]-3-fluoro-phenyl}-2-ethoxy-propionic acid,

[rac]-3-(4-{2-[2-(4-tert-Butyl-phenyl)-5-methyl-thiazol-4-yl]-ethoxy}-3-methyl-phenyl)-2-ethoxy-propionic acid,

[rac]-2-Ethoxy-3-(3-fluoro-4-{2-[2-(4-methoxy-phenyl)-thiazol-4-yl]-ethoxy}-phenyl)-propionic acid,

[rac]-3-{4-[2-(4-Chloro-phenyl)-4-methyl-thiazol-5-ylmethoxy]-2-methyl-phenyl}-2-ethoxy-propionic acid,

[rac]-2-Ethoxy-3-{2-methyl-4-[4-methyl-2-(3-trifluoromethyl-phenyl)-thiazol-5-ylmethoxy]-phenyl}-propionic acid,

[rac]-3-{4-[2-(3-Chloro-4-fluoro-phenyl)-4-methyl-thiazol-5-ylmethoxy]-2-methyl-phenyl}-2-ethoxy-propionic acid,

[rac]-2-Ethoxy-3-(4-{2-[2-(4-methoxy-phenyl)-5-methyl-thiazol-4-yl]-ethoxy}-3-methyl-phenyl)-propionic acid,

[rac]-2-Ethoxy-3-(3-fluoro-4-{2-[2-(4-methoxy-phenyl)-5-methyl-thiazol-4-yl]-ethoxy}-phenyl)-propionic acid,

[rac]-2-Ethoxy-3-(3-fluoro-4-{2-[2-(4-isopropyl-phenyl)-5-methyl-thiazol-4-yl]-ethoxy}-phenyl)-propionic acid,

[rac]-3-(4-{2-[2-(4-tert-Butyl-phenyl)-5-methyl-thiazol-4-yl]-ethoxy}-3-fluoro-phenyl)-2-ethoxy-propionic acid,

[rac]-2-Ethoxy-3-{3-fluoro-4-[2-(4-isopropyl-phenyl)-thiazol-4-yl]-propoxy}-phenyl)-propionic acid, and

[rac]-3-(4-{3-[2-(4-tert-Butyl-phenyl)-5-methyl-thiazol-4-yl]-propoxy}-3-fluoro-phenyl)-2-ethoxy-propionic acid, and pharmaceutically acceptable salts and/or pharmaceutically acceptable esters thereof.

Other preferred compounds of general formula (I) are those selected from the group consisting of

[rac]-3-(4-{2-[2-(4-tert-Butyl-phenyl)-5-methyl-thiazol-4-yl]-ethoxy}-3,5-dimethyl-phenyl)-2-ethoxy-propionic acid;

[rac]-2-Ethoxy-3-(4-{2-[2-(4-isopropyl-phenyl)-5-methyl-thiazol-4-yl]-ethoxy}-3,5-dimethyl-phenyl)-propionic acid;

[rac]-2-Ethoxy-3-(4-{2-[2-(4-isopropyl-phenyl)-5-methyl-thiazol-4-yl]-ethoxy}-3-methyl-phenyl)-propionic acid;

[rac]-3-(4-{2-[2-(4-tert-Butyl-phenyl)-5-methyl-thiazol-4-yl]-ethoxy}-3-methoxy-phenyl)-2-ethoxy-propionic acid;

[rac]-2-Ethoxy-3-(3-fluoro-4-{2-[2-(4-isopropyl-phenyl)-thiazol-4-yl]-ethoxy}-phenyl)-propionic acid;

[rac]-2-Ethoxy-3-{3-fluoro-4-[2-(2-p-tolyl-thiazol-4-yl)-ethoxy]-phenyl}-propionic acid;

[rac]-2-Ethoxy-3-{4-[2-(5-methyl-2-phenyl-thiazol-4-yl)-ethoxy]-naphthalen-1-yl}-propionic acid;

[rac]-3-{4-[2-(2-Benzo[1,3]dioxol-5-yl-5-methyl-thiazol-4-yl)-ethoxy]-3-fluoro-phenyl}-2-ethoxy-propionic acid;

[rac]-2-Ethoxy-3-{3-fluoro-4-[4-methyl-2-(4-trifluoromethyl-phenyl)-thiazol-5-ylmethoxy]-phenyl}-propionic acid;

[rac]-3-{3-Fluoro-4-[4-methyl-2-(4-trifluoromethyl-phenyl)-thiazol-5-ylmethoxy]-phenyl}-2-isopropoxy-propionic acid;

[rac]-3-{4-[2-(3,5-Dimethoxy-phenyl)-thiazol-4-ylmethoxy]-3-fluoro-phenyl}-2-ethoxy-propionic acid;

[rac]-2-Ethoxy-3-[3-fluoro-4-(2-phenyl-thiazol-4-ylmethoxy)-phenyl]-propionic acid;

[rac]-2-Ethoxy-3-[3-fluoro-4-(2-p-tolyl-thiazol-4-ylmethoxy)-phenyl]-propionic acid;

[rac]-2-Ethoxy-3-{2-ethoxy-4-[2-(5-methyl-2-phenyl-thiazol-4-yl)-ethoxy]-phenyl}-propionic acid;

[rac]-2-Ethoxy-3-(2-ethoxy-4-{2-[5-methyl-2-(4-trifluoromethyl-phenyl)-thiazol-4-yl]-ethoxy}-phenyl)-propionic acid;

[rac]-2-Ethoxy-3-(3-methyl-4-{2-[5-methyl-2-(4-trifluoromethoxy-phenyl)-thiazol-4-yl]-ethoxy}-phenyl)-propionic acid;

[rac]-2-Ethoxy-3-(3-fluoro-4-{2-[5-methyl-2-(4-trifluoromethoxy-phenyl)-thiazol-4-yl]-ethoxy}-phenyl)-propionic acid;

[rac]-2-Isopropoxy-3-{3-methoxy-4-[2-(5-methyl-2-p-tolyl-thiazol-4-yl)-ethoxy]-phenyl}-propionic acid;

[rac]-3-(3-Fluoro-4-{2-[2-(4-trifluoromethyl-phenyl)-thiazol-4-yl]-ethoxy}-phenyl)-2-isopropoxy-propionic acid;

[rac]-3-(4-{2-[2-(3,4-Dimethoxy-phenyl)-5-methyl-thiazol-4-yl]-ethoxy}-3-methoxy-phenyl)-2-ethoxy-propionic acid;

[rac]-3-(4-{2-[2-(3,5-Dimethoxy-phenyl)-5-methyl-thiazol-4-yl]-ethoxy}-3-methoxy-phenyl)-2-isopropoxy-propionic acid;

[rac]-3-(4-{2-[2-(3,5-Dimethyl-phenyl)-5-methyl-thiazol-4-yl]-ethoxy}-3-methoxy-phenyl)-2-isopropoxy-propionic acid;

[rac]-3-(4-{2-[2-(3,5-Dimethyl-phenyl)-5-methyl-thiazol-4-yl]-ethoxy}-3-methoxy-phenyl)-2-ethoxy-propionic acid;

[rac]-2-Ethoxy-3-{5-ethoxy-2-fluoro-4-[2-(4-isopropyl-phenyl)-thiazol-4-ylmethoxy]-phenyl}-propionic acid;

[rac]-3-(4-{2-[2-(4-Chloro-phenyl)-5-methyl-thiazol-4-yl]-ethoxy}-5-ethoxy-2-fluoro-phenyl)-2-ethoxy-propionic acid;

[rac]-3-(4-{2-[2-(3,5-Dimethoxy-phenyl)-5-methyl-thiazol-4-yl]-ethoxy}-3,5-difluoro-phenyl)-2-ethoxy-propionic acid;

[rac]-3-(4-{2-[2-(4-Chloro-phenyl)-5-methyl-thiazol-4-yl]-ethoxy}-3,5-difluoro-phenyl)-2-ethoxy-propionic acid;

[rac]-2-Ethoxy-3-{4-[2-(5-methyl-2-p-tolyl-thiazol-4-yl)-ethoxy]-benzo[b]thiophen-7-yl}-propionic acid;

[rac]-3-(4-{2-[2-(4-tert-Butyl-phenyl)-5-methyl-thiazol-4-yl]-ethoxy}-naphthalen-1-yl)-2-ethoxy-propionic acid;

[rac]-3-(4-{2-[2-(4-tert-Butyl-phenyl)-5-methyl-thiazol-4-yl]-ethoxy}-benzo[b]thiophen-7-yl)-2-ethoxy-propionic acid;

[rac]-2-Ethoxy-3-(4-{2-[2-(4-isopropyl-phenyl)-5-methyl-thiazol-4-yl]-ethoxy}-benzo[b]thiophen-7-yl)-propionic acid;

[rac]-2-Isopropoxy-3-(4-{2-[2-(4-isopropyl-phenyl)-5-methyl-thiazol-4-yl]-ethoxy}-naphthalen-1-yl)-propionic acid;

[rac]-2-Ethoxy-3-(4-{2-[2-(4-isopropyl-phenyl)-5-methyl-thiazol-4-yl]-ethoxy}-naphthalen-1-yl)-propionic acid;

[rac]-2-Ethoxy-3-{4-[2-(5-methyl-2-p-tolyl-thiazol-4-yl)-ethoxy]-naphthalen-1-yl}-propionic acid;

[rac]-2-Isopropoxy-3-{4-[2-(5-methyl-2-phenyl-thiazol-4-yl)-ethoxy]-benzo[b]thiophen-7-yl}-propionic acid;

[rac]-3-{4-[2-(5-Methyl-2-phenyl-thiazol-4-yl)-ethoxy]-naphthalen-1-yl}-2-propoxy-propionic acid;

[rac]-2-Methoxy-3{-4-[2-(5-methyl-2-p-tolyl-thiazol-4-yl)-ethoxy]-naphthalen-1-yl}-propionic acid;

[rac]-3-{4-[2-(5-Methyl-2-p-tolyl-thiazol-4-yl)-ethoxy]-naphthalen-1-yl}-2-propoxy-propionic acid;

[rac]-3-(4-{2-[2-(3,5-Dimethoxy-phenyl)-5-methyl-thiazol-4-yl]-ethoxy}-benzo[b]thiophen-7-yl)-2-ethoxy-propionic acid;

[rac]-3-(4-{2-[2-(3,5-Dimethoxy-phenyl)-5-methyl-thiazol-4-yl]-ethoxy}-benzo[b]thiophen-7-yl)-2-methoxy-propionic acid;

[rac]-3-(4-{2-[2-(3,5-Dimethoxy-phenyl)-5-methyl-thiazol-4-yl]-ethoxy}-benzo[b]thiophen-7-yl)-2-isopropoxy-propionic acid;

[rac]-3-(4-{2-[2-(4-tert-Butyl-phenyl)-5-methyl-thiazol-4-yl]-ethoxy}-naphthalen-1-yl)-2-isopropoxy-propionic acid;

[rac]-3-(4-{2-[2-(4-tert-Butyl-phenyl)-5-methyl-thiazol-4-yl]-ethoxy}-benzo[b]thiophen-7-yl)-2-propoxy-propionic acid;

[rac]-3-(4-{2-[2-(3,5-Dimethoxy-phenyl)-5-methyl-thiazol-4-yl]-ethoxy}-naphthalen-1-yl)-2-ethoxy-propionic acid;

[rac]-2-Ethoxy-3-{4-[2-(5-methyl-2-phenyl-thiazol-4-yl)-ethoxy]-naphthalen-1-yl}-propionic acid;

[rac]-2-Ethoxy-3-{4-[2-(5-methyl-2-phenyl-thiazol-4-yl)-ethoxy]-benzo[b]thiophen-7-yl}-propionic acid;

[rac]-2-Ethoxy-3-[2-methyl-4-(4-methyl-2-phenyl-thiazol-5-ylmethoxy)-phenyl]-propionic acid;

[rac]-3-{4-[2-(2-Chloro-phenyl)-4-methyl-thiazol-5-ylmethoxy]-2-methyl-phenyl}-2-ethoxy-propionic acid;

(S)-3-{4-[2-(4-Chloro-phenyl)-thiazol-4-ylmethoxy]-2-fluoro-phenyl}-2-ethoxy-propionic acid;

[rac]-3-{7-[2-(4-Chloro-phenyl)-thiazol-4-ylmethoxy]-2,3-dihydro-benzofuran-4-yl}-2-ethoxy-propionic acid;

[rac]-3-{7-[2-(4-Chloro-phenyl)-thiazol-4-ylmethoxy]-benzofuran-4-yl}-2-ethoxy-propionic acid;

[rac]-2-Ethoxy-3-[2-methyl-4-(5-methyl-2-phenyl-thiazol-4-ylmethoxy)-phenyl]-propionic acid;

[rac]-3-{4-[2-(4-Chloro-phenyl)-5-methyl-thiazol-4-ylmethoxy]-2-methyl-phenyl}-2-ethoxy-propionic acid;

[rac]-2-Ethoxy-3-(4-{2-[2-(4-methoxy-phenyl)-5-methyl-thiazol-4-yl]-ethoxy}-2-methyl-phenyl)-propionic acid;

[rac]-2-Ethoxy-3-(4-{2-[2-(4-methoxy-phenyl)-thiazol-4-yl]-ethoxy}-2-methyl-phenyl)-propionic acid;

[rac]-2-Ethoxy-3-{4-[2-(3-methoxy-phenyl)-4-methyl-thiazol-5-ylmethoxy]-2-methyl-phenyl}-propionic acid;

[rac]-3-{4-[2-(2,4-Dichloro-phenyl)-4-methyl-thiazol-5-ylmethoxy]-2-methyl-phenyl}-2-ethoxy-propionic acid;

[rac]-3-(4-{3-[2-(4-tert-Butyl-phenyl)-5-methyl-thiazol-4-yl]-propoxy}-2-methyl-phenyl)-2-ethoxy-propionic acid;

(S)-3-{4-[2-(4-Chloro-phenyl)-thiazol-4-ylmethoxy]-2,6-dimethyl-phenyl}-2-ethoxy-propionic acid;

[rac]-3-(4-{2-[2-(4-Chloro-phenyl)-4-methyl-thiazol-5-yl]-ethoxy}-2-methyl-phenyl)-2-ethoxy-propionic acid;

[rac]-2-Ethoxy-3-{2-methyl-4-[4-methyl-2-(4-trifluoromethyl-phenyl)-thiazol-5-ylmethoxy]-phenyl}-propionic acid;

[rac]-3-(4-{2-[2-(2-Chloro-phenyl)-4-methyl-thiazol-5-yl]-ethoxy}-2-methyl-phenyl)-2-ethoxy-propionic acid;

(S)-2-Ethoxy-3-{2-ethyl-4-[4-methyl-2-(4-trifluoromethyl-phenyl)-thiazol-5-ylmethoxy]-phenyl}-propionic acid;

(S)-3-{2,6-Dimethyl-4-[4-methyl-2-(4-trifluoromethyl-phenyl)-thiazol-5-ylmethoxy]-phenyl}-2-ethoxy-propionic acid;

[rac]-2-Ethoxy-3-{2-methyl-4-[2-(4-trifluoromethyl-phenyl)-thiazol-5-ylmethoxy]-phenyl}-propionic acid;

[rac]-2-Ethoxy-3-(2-methyl-4-{2-[4-methyl-2-(3-trifluoromethyl-phenyl)-thiazol-5-yl]-ethoxy}-phenyl)-propionic acid;

[rac]-2-Ethoxy-3-{2-methyl-4-[2-(4-methyl-2-phenyl-thiazol-5-yl)-ethoxy]-phenyl}-propionic acid;

2-Ethoxy-3-(2-methyl-4-{1-[4-methyl-2-(4-trifluoromethyl-phenyl)-thiazol-5-yl]-ethoxy}-phenyl)-propionic acid, (mixture of two diastereomeric racemates);

[rac]-2-Ethoxy-3-(2-methyl-4-{1-methyl-1-[4-methyl-2-(4-trifluoromethyl-phenyl)-thiazol-5-yl]-ethoxy}-phenyl)-propionic acid;

2-Ethoxy-3-(2-methyl-4-{2-methyl-1-[4-methyl-2-(4-trifluoromethyl-phenyl)-thiazol-5-yl]-propoxy}-phenyl)-propionic acid, (mixture of two diastereomeric racemates);

[rac]-2-Ethoxy-3-(2-methyl-4-{1-methyl-1-[2-(4-trifluoromethyl-phenyl)-thiazol-5-yl]-ethoxy}-phenyl)-propionic acid;

2-Ethoxy-3-(2-methyl-4-{1-[2-(4-trifluoromethyl-phenyl)-thiazol-5-yl]-ethoxy}-phenyl)-propionic acid, (mixture of two diastereomeric racemates);

2-Ethoxy-3-(2-methyl-4-{1-[4-methyl-2-(4-trifluoromethyl-phenyl)-thiazol-5-yl]-but-3-enyloxy}-phenyl)-propionic acid, (mixture of two diastereomeric racemates);

2-Ethoxy-3-(2-methyl-4-{1-[4-methyl-2-(4-trifluoromethyl-phenyl)-thiazol-5-yl]-butoxy}-phenyl)-propionic acid, (mixture of two diastereomeric racemates);

(2S)-2-Ethoxy-3-(2-ethyl-4-{(1R/S)-[4-methyl-2-(4-trifluoromethyl-phenyl)-thiazol-5-yl]-ethoxy}-phenyl)-propionic acid;

(2S)-2-Ethoxy-3-(2-methoxy-4-{(1R/S)-[4-methyl-2-(4-trifluoromethyl-phenyl)-thiazol-5-yl]-ethoxy}-phenyl)-propionic acid;

3-(4-{Cyclopropyl-[4-methyl-2-(4-trifluoromethyl-phenyl)-thiazol-5-yl]-methoxy}-2-methyl-phenyl)-2-ethoxy-propionic acid, (mixture of two diastereomeric racemates);

3-(4-{Cyclopentyl-[4-methyl-2-(4-trifluoromethyl-phenyl)-thiazol-5-yl]-methoxy}-2-methyl-phenyl)-2-ethoxy-propionic acid, (mixture of two diastereomeric racemates);

2-Ethoxy-3-(2-methyl-4-{[4-methyl-2-(4-trifluoromethyl-phenyl)-thiazol-5-yl]-phenyl-methoxy}-phenyl)-propionic acid, (mixture of two diastereomeric racemates);

3-(4-{3-[1,3]Dioxan-2-yl-1-[4-methyl-2-(4-trifluoromethyl-phenyl)-thiazol-5-yl]-propoxy}-2-methyl-phenyl)-2-ethoxy-propionic acid, (mixture of two diastereomeric racemates);

[rac]-2-{2-Methyl-4-[4-methyl-2-(4-trifluoromethyl-phenyl)-thiazol-5-ylmethoxy]-benzyl}-butyric acid;

[rac]-2-{2-Methyl-4-[4-methyl-2-(4-trifluoromethyl-phenyl)-thiazol-5-ylmethoxy]-benzyl}-heptanoic acid;

2-(4-{Cyclopropyl-[4-methyl-2-(4-trifluoromethyl-phenyl)-thiazol-5-yl]-methoxy}-2-methyl-benzyl)-heptanoic acid, (mixture of two diastereomeric racemates);

2-(4-{Cyclopropyl-[4-methyl-2-(4-trifluoromethyl-phenyl)-thiazol-5-yl]-methoxy}-2-methyl-benzyl)-butyric acid, (mixture of two diastereomeric racemates);

[rac]-2-(2-Methyl-4-{1-methyl-1-[4-methyl-2-(4-trifluoromethyl-phenyl)-thiazol-5-yl]-ethoxy}-benzyl)-butyric acid;

[rac]-2-(2-Methyl-4-{1-methyl-1-[4-methyl-2-(4-trifluoromethyl-phenyl)-thiazol-5-yl)-ethoxy}-benzyl)-heptanoic acid;

[rac]-2-Butoxy-3-{2-methyl-4-[4-methyl-2-(4-trifluoromethyl-phenyl)-thiazol-5-ylmethoxy]-phenyl}-propionic acid;

2-Butoxy-3-(4-{cyclopropyl-[4-methyl-2-(4-trifluoromethyl-phenyl)-thiazol-5-yl]-methoxy}-2-methyl-phenyl)-propionic acid, (mixture of two diastereomeric racemates);

[rac]-2-Ethoxy-3-(4-{2-[4-methyl-2-(4-trifluoromethyl-phenyl)-thiazol-5-yl]-ethoxy}-5,6,7,8-tetrahydro-naphthalen-1-yl)-propionic acid;

[rac]-2-Ethoxy-3-{4-[4-methyl-2-(4-trifluoromethyl-phenyl)-thiazol-5-ylmethoxy]-5,6,7,8-tetrahydro-naphthalen-1-yl}-propionic acid;

[rac]-2-Ethoxy-3-{4-[2-(4-trifluoromethyl-phenyl)-thiazol-5-ylmethoxy]-5,6,7,8-tetrahydro-naphthalen-1-yl}-propionic acid;

[rac]-2-Methoxy-3-{4-[4-methyl-2-(4-trifluoromethyl-phenyl)-thiazol-5-ylmethoxy]-naphthalen-1-yl}-propionic acid;

[rac]-2-Ethoxy-3-{4-[4-methyl-2-(4-trifluoromethyl-phenyl)-thiazol-5-ylmethoxy]-naphthalen-1-yl}-propionic acid;

[rac]-2-Methoxy-3-{4-[4-methyl-2-(4-trifluoromethyl-phenyl)-thiazol-5-ylmethoxy]-benzo[b]thiophen-7-yl}-propionic acid;

[rac]-2-Ethoxy-3-{4-[4-methyl-2-(4-trifluoromethyl-phenyl)-thiazol-5-ylmethoxy]-benzo[b]thiophen-7-yl}-propionic acid; and 2-Methoxy-3-(4-{2-methyl-1-[4-methyl-2-(4-trifluoromethyl-phenyl)-thiazol-5-yl]-propoxy}-benzo[b]thiophen-7-yl)-propionic acid, (mixture of two diastereomeric racemates);

and pharmaceutically acceptable salts and/or pharmaceutically acceptable esters thereof.

Particularly preferred compounds of formula (I) are those selected from the group consisting of

[rac]-2-Ethoxy-3-{4-[2-(5-methyl-2-phenyl-thiazol-4-yl)-ethoxy]-benzo[b]thiophen-7-yl}-propionic acid,

[rac]-2-Ethoxy-3-{4-[2-(4-isopropyl-phenyl)-thiazol-4-ylmethoxy]-3-methyl-phenyl}-propionic acid,

[rac]-2-Ethoxy-3-{3-fluoro-4-[2-(4-trifluoromethyl-phenyl)-thiazol-4-ylmethoxy]-phenyl}-propionic acid,

[rac]-2-Ethoxy-3-{2-methyl-4-[2-(5-methyl-2-phenyl-thiazol-4-yl)-ethoxy]-phenyl}-propionic acid,

[rac]-3-{4-[2-(4-Chloro-phenyl)-thiazol-4-ylmethoxy]-2-methyl-phenyl}-2-ethoxy-propionic acid, (2S)-3-{4-[2-(4-Chloro-phenyl)-thiazol-4-ylmethoxy]-2-methyl-phenyl}-2-ethoxy-propionic acid, (2S)-3-{2-Chloro-4-[2-(4-chloro-phenyl)-thiazol-4-ylmethoxy]-phenyl}-2-ethoxy-propionic acid, and

[rac]-2-Ethoxy-3-(3-fluoro-4-{2-[2-(4-trifluoromethyl-phenyl)-thiazol-4-yl]-ethoxy}-phenyl)-propionic acid, and pharmaceutically acceptable salts and/or pharmaceutically acceptable esters thereof.

Other particularly preferred compounds of formula (I) are those selected from the group consisting of

[rac]-2-Ethoxy-3-(3-fluoro-4-{3-[2-(4-isopropyl-phenyl)-thiazol-4-yl]-propoxy}-phenyl)-propionic acid;

[rac]-2-Ethoxy-3-{5-ethoxy-2-fluoro-4-[2-(4-isopropyl-phenyl)-thiazol-4-ylmethoxy]-phenyl}-propionic acid;

[rac]-3-{4-{2-[2-(3,5-Dimethoxy-phenyl)-5-methyl-thiazol-4-yl]-ethoxy}-benzo[b]thiophen-7-yl)-2-isopropoxy-propionic acid;

(S)-3-{4-[2-(4-Chloro-phenyl)-thiazol-4-ylmethoxy]-2-fluoro-phenyl}-2-ethoxy-propionic acid;

2-Ethoxy-3-(2-methyl-4-{1-[4-methyl-2-(4-trifluoromethyl-phenyl)-thiazol-5-yl]-ethoxy}-phenyl)-propionic acid, (mixture of two diastereomeric racemates);

2-Ethoxy-3-(2-methyl-4-{2-methyl-1-[4-methyl-2-(4-trifluoromethyl-phenyl)-thiazol-5-yl]-propoxy}-phenyl)-propionic acid, (mixture of two diastereomeric racemates);

2-(4-{Cyclopropyl-[4-methyl-2-(4-trifluoromethyl-phenyl)-thiazol-5-yl]-methoxy}-2-methyl-benzyl)-butyric acid, (mixture of two diastereomeric racemates);

[rac]-2-Ethoxy-3-{4-[2-(4-trifluoromethyl-phenyl)-thiazol-5-ylmethoxy]-5,6,7,8-tetrahydro-naphthalen-1-yl}-propionic acid; and

[rac]-2-Ethoxy-3-{4-[4-methyl-2-(4-trifluoromethyl-phenyl)-thiazol-5-ylmethoxy]-naphthalen-1-yl}-propionic acid;

and pharmaceutically acceptable salts and/or pharmaceutically acceptable esters thereof.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula (I) in this invention maybe derivatised at functional groups to provide derivatives which are capable of conversion back to the parent compound in vivo. Physiologically acceptable and metabolically labile derivatives, which are capable of producing the parent compounds of general formula (I) in vivo are also within the scope of this invention.

A further aspect of the present invention is the process for the manufacture of compounds of formula (I) as defined above, which process comprises removing a protecting group in a compound of formula (II)

(II)

[Chemical structure of formula (II) showing a thiazole ring with substituents $R^1$, $R^2$, X, Y connected via $(CR^9R^{10})_n$—O— to a phenyl ring with substituents $R^3$, $R^4$, $R^5$, $R^6$, and a propionic acid ester group with $R^7$ and —O—PG]

wherein $R^1$, $R^2$, $R^3$, $R^4$, $R^5$, $R^6$, $R^7$, $R^9$, $R^{10}$, X, Y and n are as defined as before and PG is a protecting group.

Possible protecting groups PG in compounds of formula (II) are e.g. lower-alkyl-, β-trimethylsilylethyl- and β-trichloroethyl-esters, which can be used for the protection of the corresponding carboxy group. Lower-alkyl-ester protecting groups can be removed in the presence of a base such as e.g. LiOH or NaOH in a solvent such as e.g. $H_2O$, ethanol, tetrahydrofuran, or dioxan, or in a mixture of such solvents, e.g. in a temperature range of 10–50° C. The β-trichloroethyl-ester protecting group can be removed in the presence of Zn in acetic acid, e.g. in a temperature range of 10–50° C. The β-trimethylsilylethyl-ester protecting group can be removed in the presence of tetrabutylammonium fluoride in tetrahydrofuran, e.g. in a temperature range of 20–65° C. Methods for converting a compound of formula (I) as defined above to a pharmaceutically acceptable salt are known in the art.

The invention further relates to compounds of formula (I) as defined above, when manufactured according to a process as defined above.

As described above, the compounds of formula (I) of the present invention can be used as medicaments for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases (such as e.g. crown disease, inflammatory bowel disease, collitis, pancreatitis, cholestasis/fibrosis of the liver, and diseases that have an inflammatory component such as e.g. Alzheimer's disease or impaired/improvable cognitive function) and proliferative diseases (cancers such as e.g.

liposarcoma, colon cancer, prostate cancer, pancreatic cancer and breast cancer). The use as medicament for the treatment and/or prevention of non-insulin dependent diabetes mellitus is preferred.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus.

In another embodiment, the invention relates to a method for the treatment and/or prevention of diseases which are modulated by PPARα and/or PPARγ agonists, which method comprises administering a compound of formula (I) to a human or animal. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably for the treatment and/or prevention of non-insulin dependent diabetes mellitus.

The invention further relates to the use of compounds as defined above for the treatment and/or prevention of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus.

In addition, the invention relates to the use of compounds as defined above for the preparation of medicaments for the treatment and/or prevention of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Racemates of compounds of formula (I) [compounds 9 and compounds 10 in scheme 1] can e.g. be synthesized according to the methods depicted in scheme 1 or by analogous methods.

Homochiral compounds of formula (I) (compounds 8 and 9 in scheme 2 and compounds 6 and 7 in scheme 3) can be prepared according to the methods depicted in scheme 2 and 3 or by analogous methods.

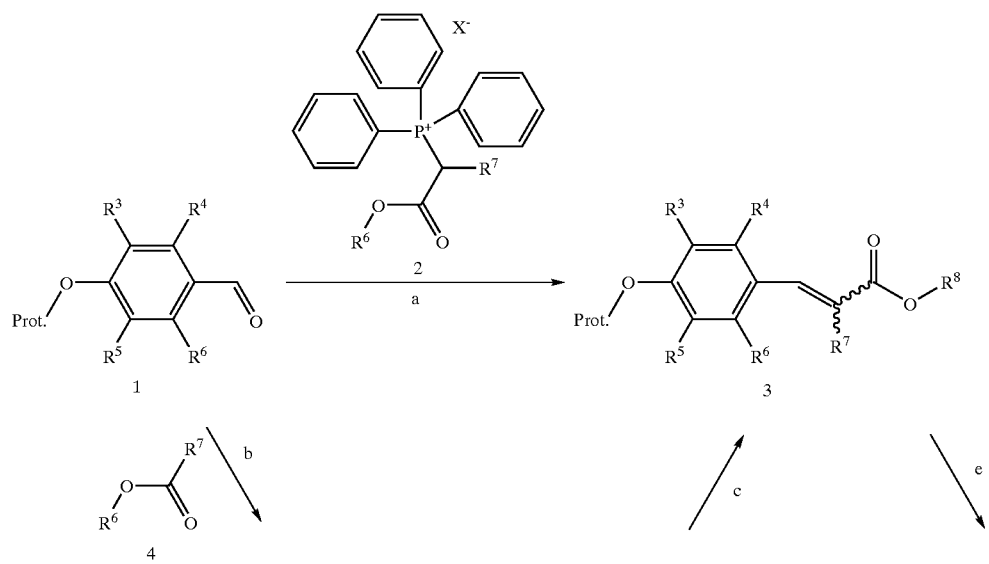

Scheme 1

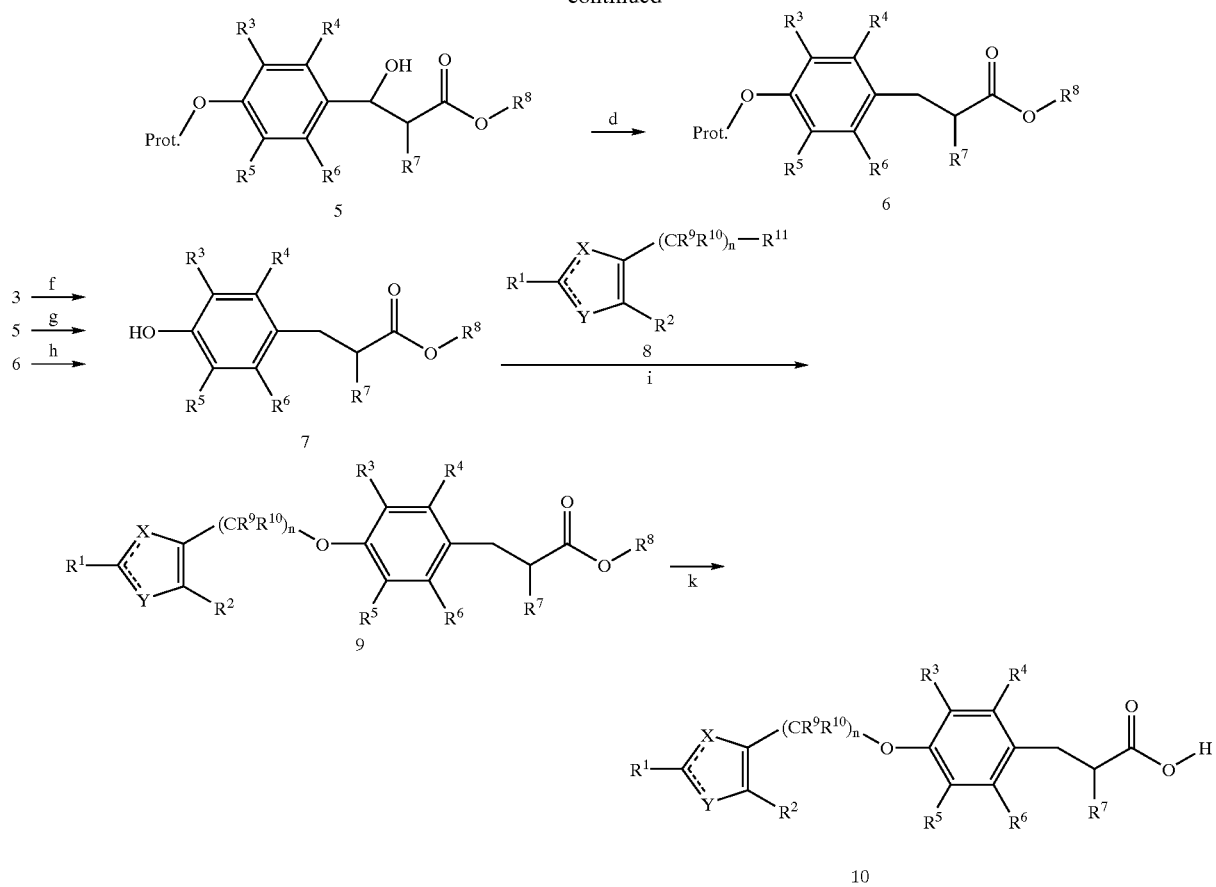

Aldehydes 1 can be reacted with a Wittig salt 2 such as (1,2-diethoxy-2-oxoethyl)triphenyl phosphonium chloride or (1,2-dimethoxy-2-oxoethyl)triphenyl phosphonium bromide in solvents like isopropanol, dichloromethane or tetrahydrofuran or mixtures thereof in the presence of a base like potassium carbonate, 1,8-diazabicyclo[5.4.0]undec-7-ene (DBU) or 1,1,3,3-tetramethyl-guanidine, preferably between 0° C. and the reflux temperature of the solvents, giving acrylic esters 3 as E and/or Z isomers (step a). Hydrogenation of acrylic esters 3 using palladium on charcoal as catalyst, preferably at room temperature and 1 atm. pressure of hydrogen, in solvents like methanol, ethanol, tetrahydrofuran, acetic acid, dichloromethane and mixtures thereof, affords racemic esters 7, provided that the protecting group can be cleaved reductively (step f). Hydrogenation of compounds in which $R^3$–$R^4$ together with the attached benzene ring form a benzofuran moiety can be performed using extended reaction times to provide the corresponding benzo-dihydrofuran analogues. In compounds, in which $R^3$–$R^4$ together with the attached benzene ring form a benzothiophene or a benzofuran moiety, the reduction of the double bond is preferably performed with a reducing metal like magnesium in solvent mixtures like tetrahydrofuran/methanol between room temperature and the reflux temperature of the solvents leading to saturated compounds 6 (step e). Subsequently, the protecting group like a benzyl ether is cleaved, e.g. by using dimethyl sulfide and boron trifluoride diethyl etherate in a solvent like dichloromethane between room temperature and the reflux temperature of the solvent to give phenolic compounds 7 (step h).

Alternatively, aldehydes 1 are reacted with the enolate of alkanoic acid esters or alkoxy- or aryloxy-acetic acid esters 4 (preferably the lithium-enolate, prepared at –78° C. by treatment of 4 with a strong, non-nucleophilic base like lithium diisopropylamide in an inert solvent like tetrahydrofuran), preferably at temperatures around –78° C., in solvents like tetrahydrofuran giving the aldol product 5 as a mixture of diasteromers (step b). Removal of the benzylic hydroxy group in 5 with a reducing agent like e.g. triethylsilane in the presence of a Lewis acid, like boron-trifluoride, or a protic acid, like trifluoroacetic acid, in a suitable solvent like trifluoroacetic acid itself or dichloromethane between 0° C. and 60° C. yields racemic esters 6 (step d); ensuing removal of the protecting group, e.g. a benzyloxy function, can then be performed by standard technology, e.g. catalytic hydrogenation using hydrogen and a catalyst like palladium to give phenolic compounds 7 (step h). Catalytic hydrogenation can also be used to convert in one step benzyl protected hydroxy compounds 5 into phenolic compounds 7 (step g), preferably using palladium on charcoal as catalyst in the presence of an acid like oxalic acid in solvents like alcohols at temperatures around room temperature and a hydrogen pressure up to 100 bar. The cleavage of the protective function can also be performed before the removal of the benzylic hydroxy group; in such a case, similar reaction conditions can be chosen for the removal of the benzylic hydroxy group as just described for the transformation of compounds 5.

As an alternative method, compounds 5 can be treated with catalytic amounts of an acid like para toluene sulfonic acid in a solvent like benzene or toluene, preferably under conditions allowing the removal of the water formed (e.g. with a Dean Stark trap or in the presence of molecular sieves) at temperatures between room temperature and the reflux temperature of the solvents to yield acrylic esters 3 (step c).

Aryl-thiazole compounds 8 (prepared as outlined in schemes 11–14) are condensed with phenols 7 according to well known procedures: if $R^{11}$ represents a hydroxy group e.g. via Mitsunobu-reaction, with triphenylphosphine and di-tert-butyl-, diisopropyl- or diethyl-azodicarboxylate as reagents; this transformation is preferably carried out in a solvent like toluene, dichloromethane or tetrahydrofuran at ambient temperature. Alternatively, if $R^{11}$ represents a halide, mesylate or tosylate moiety, the aryl-thiazole compounds 8 can be reacted with phenols 7 in solvents like N,N-dimethylformamide, acetonitrie, acetone or methylethyl ketone in the presence of a weak base like cesium or potassium carbonate at a temperature ranging from room temperature to 140° C., preferably around 50° C. to yield ether compounds 9 (step i). Those can optionally be hydrolyzed according to standard procedures, e.g. by treatment with an alkali hydroxide like LiOH or NaOH in a polar solvent mixture like tetrahydrofuran/ethanol/water leading to carboxylic acids 10 (step k). If the aryl-thiazole compounds 8 (prepared as described in schemes 11–14) contain chiral centers, ester compounds 9 and carboxylic acids 10 are obtained as mixtures of diastereomers, which can be separated by methods well known in the art, e.g. HPLC chromatography or crystallization.

Scheme 2

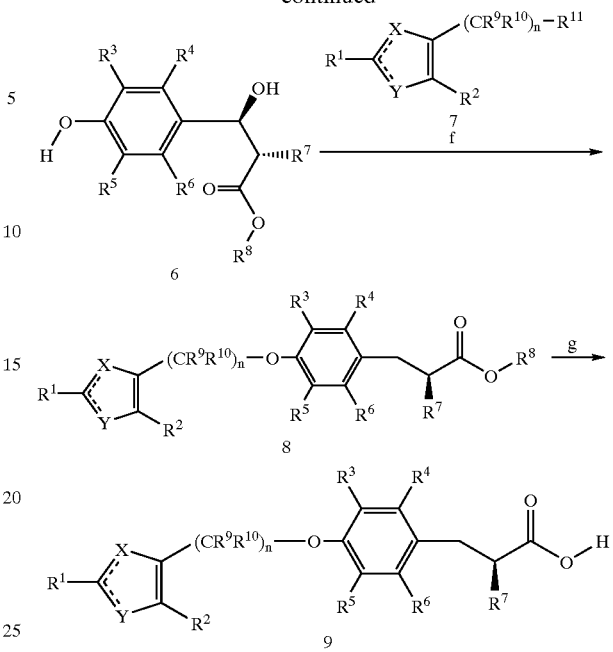

Homochiral alpha-substituted-phenyl-propionic acid esters of formula 8 and free acids of formula 9 can be prepared according to the method depicted in scheme 2 or by analogous methods known in the art.

The well known chiral auxiliary 2[(S)-4-benzyl-oxazolidin-2-one] is condensed with an alkanoyl chloride or an alkoxy- or aryloxy-acetyl chloride 1 in the presence of a strong base like n-butyl lithium in an inert solvent like tetrahydrofuran at temperatures around −78° C. to produce building block 3 (step a). The latter is then treated according to literature precedence [Tetrahedron Asymmetry (1999), 10, 1353–1367] with dibutylboron-triflate and a tertiary amine like triethylamine in dichloromethane to generate the corresponding boron enolate, which is subsequently reacted at low temperatures with aldehydes 4 resulting in compounds 5 (step b). In compounds 5, one of all four possible stereoisomers is strongly predominating (stereochemistry as indicated without rigorous proof with respect to the benzylic position). Compounds 5 are converted into phenolic intermediates 6 via a three step sequence encompassing: i) carefully controlled ester formation using only a minimal excess of alcoholate in the corresponding alcohol as solvent or in solvents like tetrahydrofuran or dioxane at temperatures ranging from −20° C. to room temperature (step c); ii) reductive removal of the benzylic hydroxy group as described above for the conversion of compounds 5 to compounds 6 in scheme 1 (step d); iii) removal of the protecting group by standard technology (step e); the order of the three reaction steps c, d, e is interchangeable, and the simultaneous removal of the benzylic hydroxy function and a benzyl protecting group as described for the conversion of compounds 5 to compounds 7 in scheme 1 is also possible. The transformation of phenolic intermediates 6 into ester 8 and/or acids 9 can be performed in perfect analogy as described for racemic phenolic intermediates 7 in scheme 1 (steps f and g). If carefully controlled reaction conditions are applied as detailed in the experimental part, hardly any racemisation occurs during this reaction sequence. The optical purity of compounds 8 and 9 can be determined by chiral HPLC or by $^1$H-NMR-spectroscopy in the presence of a chiral solvent like 1-(9-anthryl)-2,2,2-trifluoro-ethanol. If the aryl-thiazole compounds 7 (prepared as described in schemes 11–14) contain chiral centers and are not optically pure, ester compounds 8 and carboxylic acids 9 are obtained as mixtures of diastereomers, which can be separated by methods well known in the art, e.g. HPLC chromatography or crystallization.

4 (step b). Removal of the benzylic hydroxy function in compounds 4 leads to compounds 5 (step c), which can be converted into the corresponding esters 6 (step d) or acids 7 (step e) as described for the analogous reactions in scheme 1 and 2, respectively. Optionally, ester compounds 6 can be hydrolysed to acids 7 (step f). If the aryl-thiazole compounds

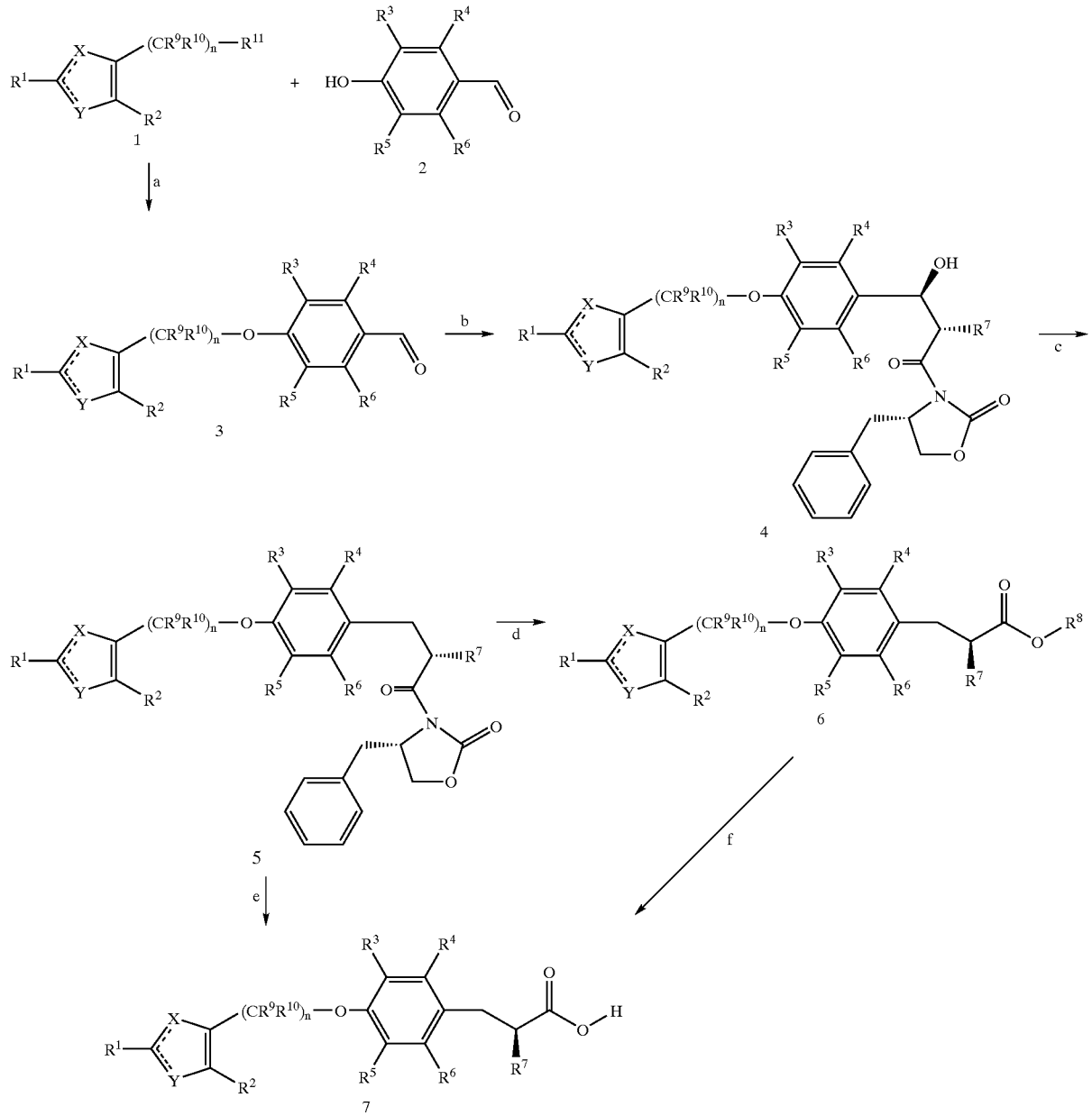

Scheme 3

Homochiral alpha-substituted-phenyl-propionic acid esters of formula 6 and free acids of formula 7 can also be prepared according to a linear synthetic sequence depicted in scheme 3. Thus, reaction types already described in scheme 2 are used in a different order beginning with the condensation of aryl-thiazole synthons 1 with phenols 2 affording ether compounds 3 bearing an aldehyde moiety (step a). These ether compounds 3 are then reacted with the chiral synthons (compounds 3 in scheme 2) to form aldol-adducts 1 (prepared as described in schemes 11–14) contain chiral centers and are not optically pure, ester compounds 6 and carboxylic acids 7 are obtained as mixtures of diastereomers, which can be separated by methods well known in the art, e.g. HPLC chromatography or crystallization.

Aldehydes 1 (scheme 1), aldehydes 4 (scheme 2), aldehydes 2 (scheme 3), are known or can be synthesized by methods known in the art. Examples for possible syntheses of these key intermediates are given in schemes 4–10.

Scheme 4

Known phenols 1 can be transformed into aldehydes 3 either by known formylation reactions such as e.g. the Vismeier formylation, by treatment with hexamethylene tetramine under acidic conditions, e.g. in the presence of sulfuric acid or preferably with trifluoroacetic acid as solvent between 0° C. and the reflux temperature of trifluoroacetic acid, or by formylation with dichloromethyl methyl ether in the presence of titanium tetrachloride, preferably in dichloromethane at temperatures between −78° C. and the reflux temperature of the solvent (step a); alternatively, a two step procedure might be used: introduction of a halogen atom into the para position, e.g. by use of N-bromo- or N-iodo-succinimide, e.g. in a mixture of concentrated sulfuric acid and tetrahydrofuran preferably at ambient temperature, followed by a metal halogen exchange, realized by treatment with an alkyl-lithium reagent like n-butyllithium, preferably at temperatures around −78° C., and quenching the resulting aryl-Li with a formyl transfer reagent like N,N-dimethylformamide or N-formyl-piperidine (steps b and c). Alternatively, a carbonylation reaction can be used for the introduction of the formyl group in step c, e.g. by use of sodium formate, bis(triphenylphosphine)palladium(II) dichloride and CO gas in a solvent like N,N-dimetylformamide, preferably at temperatures around 100° C.

Scheme 5

4-Hydroxy-benzofuran 5 (R⁶=H)[Synthetic Communications (1986), 16(13), 1635–1640; Helvetica Chimica Acta (1933), 16, 121–129) and 4-hydroxy-benzothiophene 9 (R⁶=H) [Jpn. Kokai Tokkyo Koho (2001), 2001048876A2] are known. Thus, cyclohexane-1,3-diones 1 carrying variable substituents $R^6$ at the 5-position can be reacted with bromopyruvic acid in methanol in the presence of a base like potassium hydroxide at temperatures between 0° C. and the reflux temperature of methanol followed by treatment with hydrochloric acid at around 100° C. to give furan-carboxylic acids 3 (step a). Treatment of these furan-carboxylic acids 3 in an inert solvent like decahydro-naphthalene in the presence of a hydrogen acceptor like dodecene and palladium on carbon, preferably at reflux, provides carboxy-benzofurans 4 (step b), which are decarboxylated to benzofurans 5, e.g. by using copper powder in quinoline at temperatures between 200° C. and 240° C. (step c). Similar to the transformations described in scheme 4, benzofurans 5 can finally be converted into formylated benzofuran intermediates 6 (step d).

Treatment of 2-thiophenecarbaldehyde 7 with suitable vinyl-lithium- or vinyl-magnesium-derivatives in solvents like tetrahydrofuran or 1,2-dimethoxy-ethane, preferably in a temperature range between −78° C. and room temperature, followed by in situ treatment with acetic anhydride yields thiophenes 8 with variable substitution R⁶ (step e). Treatment of thiophenes 8 with carbon monoxide, preferably at a pressure of 20 to 60 bar, a palladium catalyst like palladium acetate, a phosphine like triphenylphosphine, in solvent mixtures which may typically contain acetic anhydride, triethylamine, toluene or tetrahydrofuran, preferably in a temperature range between 100° C. to 160° C., affords after saponification of the acetate function benzothiophenes 9 (step f). Similar to the transformations described in scheme 4, benzothiophenes 9 can finally be converted into formylated benzothiophene intermediates 10 (step g).

Scheme 6

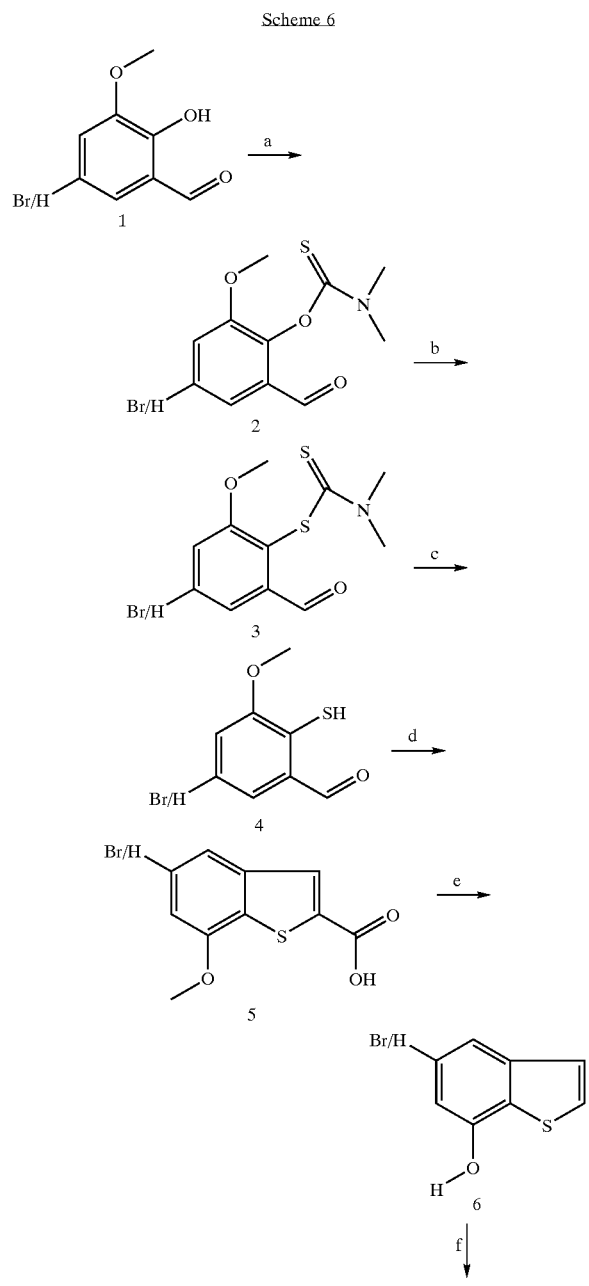

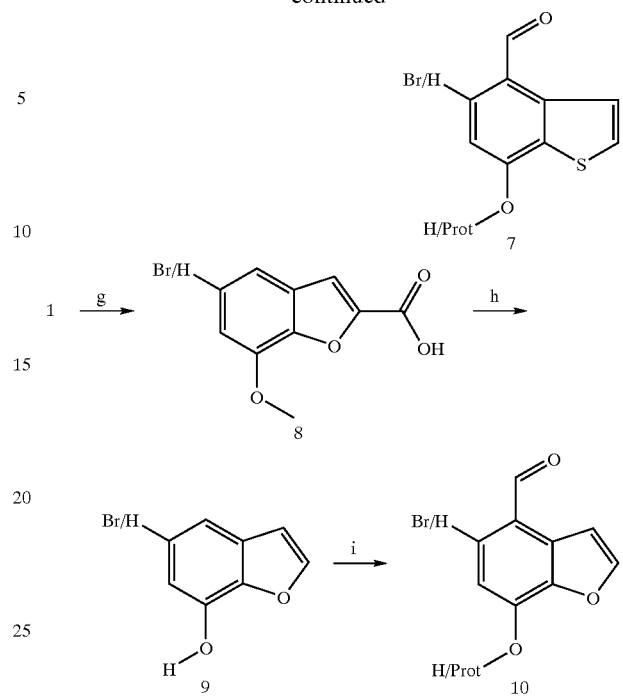

2-Hydroxy-3-methoxy-benzaldehyde 1, optionally substituted with bromine in position 5, can be transformed into benzo[b]thiophen-7-ol 6 or 5-bromo-benzo[b]thiophen-7-ol 6. This sequence can be carried out in analogy to the method described in J. Chem. Soc., Perkin Trans. 1 1983(12), 2973–7; for the transformation of 2-hydroxy-3-methoxy-benzaldehyde into benzo[b]thiophen-7-ol. It involves the following steps: treatment with N,N-dimethylthiocarbamoyl chloride in a solvent like tetrahydrofuran in the presence of an aqueous base like potassium hydroxide in water or in the presence of an organic base like diisopropyl-ethyl-amine, preferably at temperatures between 0° C. and room temperature, generates thionocarbamates 2 (step a); thermal rearrangement of compounds 2 without solvent or preferably in an inert solvent like diphenyl ether at temperatures between 200° C. and 280° C. leads to arylthiocarbamates 3 (step b); saponification in a solvent like an alcohol with a base like sodium or potassium hydroxide, preferably between room temperature and the reflux temperature of the solvents, leads then to thiophenols 4 (step c); reaction of these thiophenols 4 with sodium chloroacetate in water or a water/alcohol mixture in the presence of a base like sodium or potassium hydroxide in a temperature range between room temperature and the reflux temperature of the solvents produces then benzothiophene-carboxylic acids 5 (step d); decarboxylation, e.g. in quinoline in the presence of copper bronze at temperatures between 200° C. and 240° C., followed by cleavage of the methyl ether function, e.g. by treatment with aqueous hydrobromic acid in acetic acid at reflux, then yields benzo[b]thiophen-7-ols 6 (step e). Similar to the transformations described in scheme 4, benzo[b]thiophen-7-ols 6 can finally be converted into formylated benzo[b]thiophen-7-ol intermediates 7 (step f).

7-Hydroxy-benzofuran is known and commercially available [J. Med. Chem. (1987), 30(1), 62–7]. In a sequence similar to that described above, the 5-bromo-analogue can be prepared from 2-hydroxy-3-methoxy-benzaldehyde 1 by reaction with ethyl chloro-actetate in a solvent like N,N-dimethylformamide in the presence of a base like potassium carbonate at temperatures between 60° C. and 120° C. yielding benzofuran carboxylic acid 8 (step g). Decarboxylation as described above and ensuing ether cleavage, preferably with pyridine hydrochloride at temperatures around 200° C., then leads to 5-bromo-7-hydroxy-benzofuran 9 (step h). Similar to the transformations described in scheme 4, 5-bromo-7-hydroxy-benzofuran 9 can finally be converted into formylated 5-bromo-7-hydroxy-benzofuran intermediate 10 (step i).

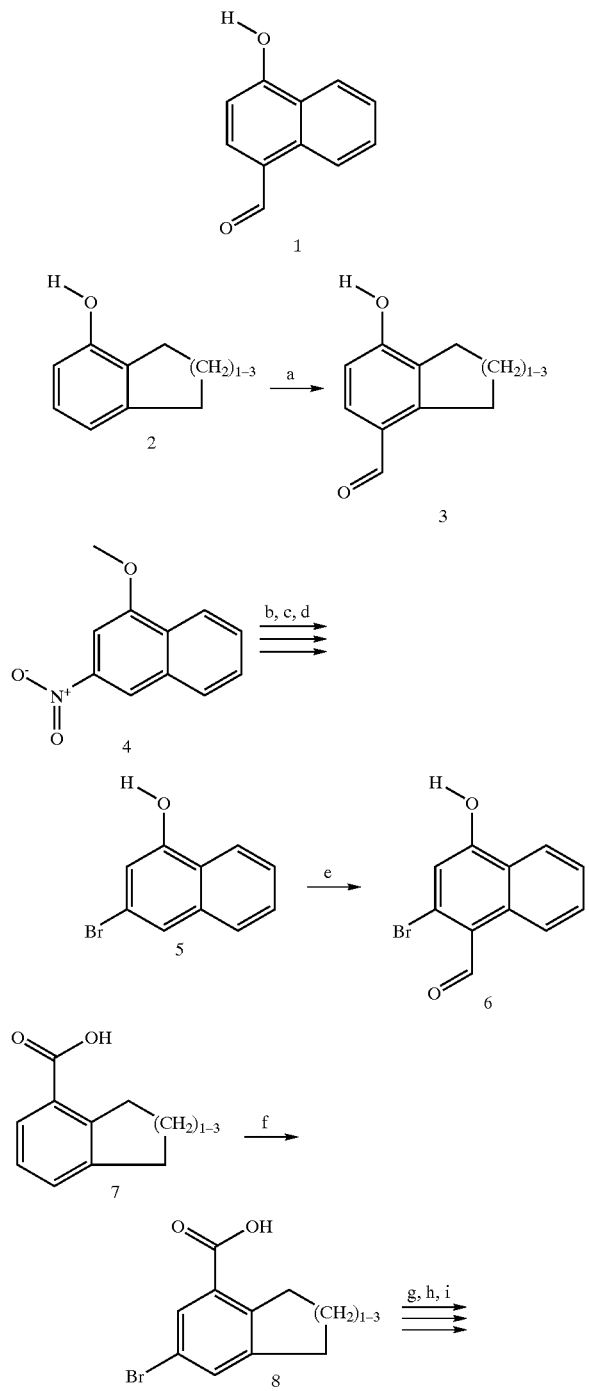

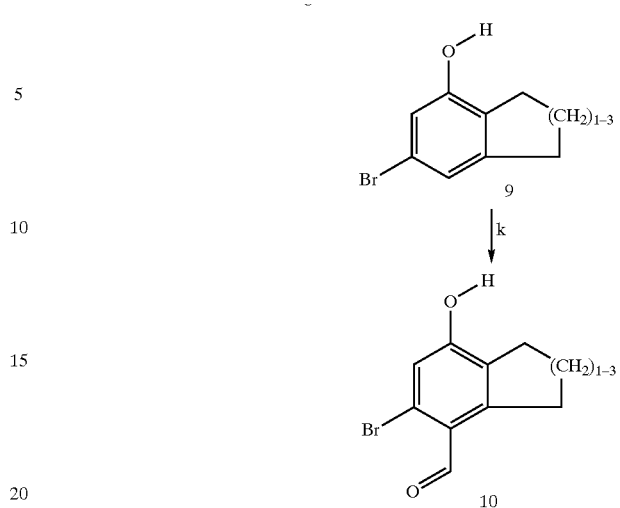

1-Hydroxy-4-formyl-naphthalene 1 and 2,3-annelated phenols 2 with a ring size of 5,6 and 7 are commercially available or known [see J. Am. Chem. Soc. (1988), 110(19), 6471–6480; U.S. (2000) U.S. Pat. No. 6,121,397; PCT Int. Appl. (1999) WO99/10339]. Similar to the transformations described in scheme 4, 2,3-annelated phenols 2 can be converted into formylated 2,3-annelated phenols 3 (step a).

3-Bromo-1-hydroxy-naphthalene 5, an intermediate carrying a functionality, which allows synthetic modifications at a later stage, can be prepared from 3-nitro-1-methoxy-naphthalene 4 [Monatsh. Chem. (1992), 123(6–7), 637–645] by well established procedures, i. e. reduction of the nitro function, e.g. by hydrogenation in the presence of a palladium catalyst, followed by diazotisation, Sandmeyer reaction and cleavage of the methyl ether function giving 3-bromo-1-hydroxy-naphthalene 5 (steps b, c, d). Similar to the transformations described in scheme 4, 3-bromo-1-hydroxy-naphthalene 5 can be converted into 3-bromo-4-formyl-1-hydroxy-naphthalene 6 (step e).

2,3-Annelated carboxylic acids 7 are known, their 3-bromo analogues 8 are known or can be prepared by established methods of bromination of aromatic nuclei [J. Org. Chem. (1978), 43(11), 2167–70; Ger. Offen. (1977), DE 2633905] (step f). Such 3-bromo-benzoic acids can then be converted into the corresponding phenols 9 by known methods such as e.g. exhaustive reduction with borane to the corresponding alcohol, oxidation, e.g. using Swern conditions (oxalyl chloride/dimethylsulfoxide/triethylamine in dichloromethane, −78° C. to room temperature), to the corresponding aldehyde, followed by Baeyer-Viliger oxidation e.g. with peracetic acid (40%) in acetic acid (steps g, h, i). Similar to the transformations described in scheme 4, phenols 9 can be converted into intermediates 10 (step k).

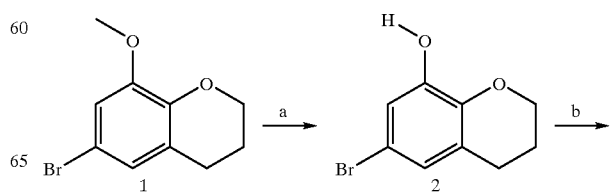

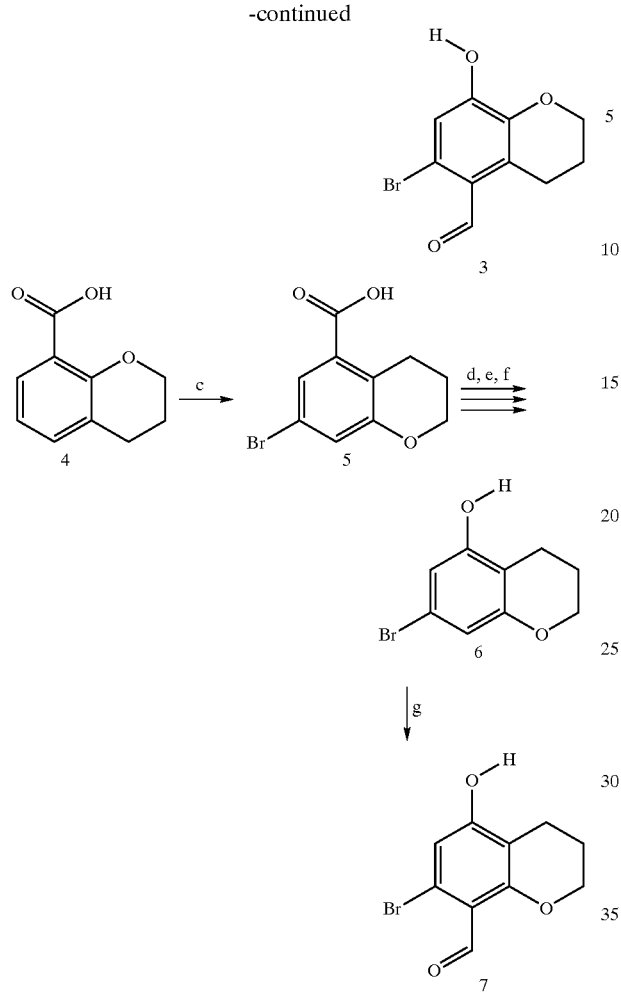

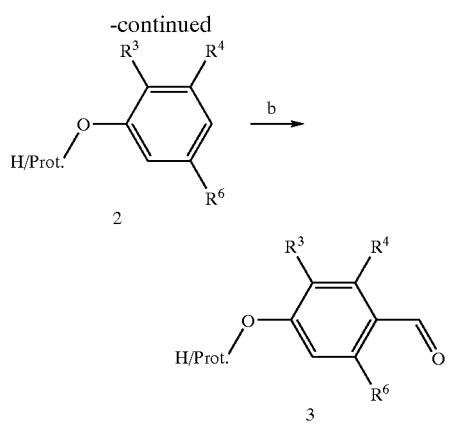

3-Bromo-phenols 1 (intermediates 6, scheme 6, intermediates 9, scheme 6, intermediates 5, scheme 7, intermediates 9, scheme 7, as well as intermediates 2 and 6, scheme 8), optionally carrying a protective function, can be converted into analogous phenols 2 carrying variable substiutents $R^6$ by first transforming the bromo-compound into the corresponding aryl-lithium derivative (e.g. by using an alkyl lithium reagent in a solvent like tetrahydrofuran, preferably at a temperature around −78° C.) and then quenching the latter with a variety of electrophiles using methods well known in the art (step a). For the synthesis of phenols ($R^6$=OH), the aryl lithium compounds are reacted with trimethylborate at temperatures between −78° C. and the reflux temperature of tetrahydrofuran, followed by oxidation e.g. with N-methyl morpholine N-oxide or $H_2O_2$/NaOH, preferably at the reflux temperature of tetrahydrofuran [compare Synlett 1995(09), 931–932]. These phenols 2 with $R^6$ equal OH can then be transformed into the corresponding ether compounds by well known methods. Similar to the reaction sequence described in scheme 4, phenolic compounds 2 can finally be converted into phenolic aldehyde intermediates 3 (step b).

Bromo-methoxy compound 1 characterized by an annelated dihydro-2H-pyran ring is known [Can. J. Chem. (1982), 60(16), 2093–81. Cleavage of the methoxy ether function with pyridine hydrochloride at temperatures around 200° C. leads to 3-bromo-phenol 2 (step a). Similar to the transformations described in scheme 4, compound 2 can be converted into intermediate 3 (step b).

The isomeric building block can be obtained as follows: Carboxylic acid 4 [U.S. (1999), U.S. Pat. No. 5,856,529 A] can be brominated to give the 3-bromo derivative 5 (step c), which can be transformed into phenol 6 by a sequence analogous to that described for the transformation of compounds 8 into compounds 9 in scheme 7 (steps d, e, f). Similar to the transformations described in scheme 4, phenol 6 can be converted into intermediate 7 (step g).

Scheme 9

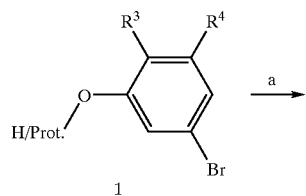

Scheme 10

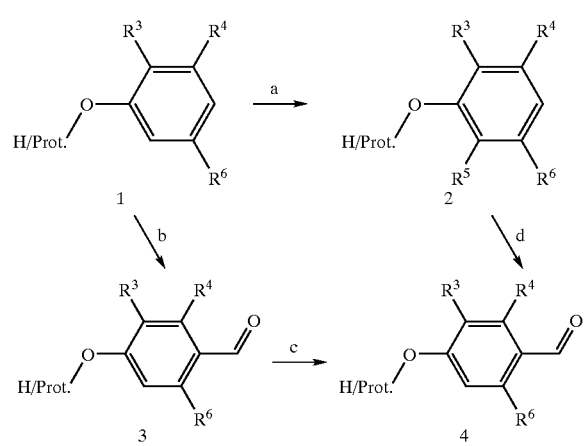

Phenols 1, optionally carrying a protecting group, can be further transformed into phenols 2 carrying additional substiutents $R^5$ by known methods of electrophilic aromatic substitution. In many cases, mixture of ortho/para-substitution-, and ortho/para-disubstitution-products will be formed in ratios depending on the precise reaction conditions. In such cases, the reaction conditions can be optimized in order to achieve the highest possible yield of mono-ortho product; optionally, product mixtures can also be separated into pure isomers by known methods such as silica gel chromatography (step a). 4-Formyl compounds 3 can be obtained from phenols 1, optionally carrying a protecting group, by transformations as described in scheme 4 (step b). 4-Formyl compounds 3 can then again be used as starting materials applying known methods of electrophilic aromatic substitutions leading to compounds 4 carrying an additional $R^5$ substituent (step c). Alternatively, compounds 4 may be obtained from phenols 2 by transformations as described in scheme 4 (step d).

hydride in ether or tetrahydrofuran (step c). Alternatively, ester compounds 4 can be transformed into compounds 5 by i) saponification to the corresponding acid; ii) treatment with $R^9Li$ optionally in the presence of a Cu(I) salt in ether or tetrahydrofuran to yield the alkyl ketones —$COR^9$; iii) subsequent reaction with $R^{10}Li$ or lithium aluminium hydride in ether or tetrahydrofuran (step c). Optionally, an elongation of the side chain can then be performed by standard methods, such as transformation of the alcohol function into a leaving group, e.g. a mesylate, ensuing treatment with cyanide, saponification and reduction, afford- Scheme 11

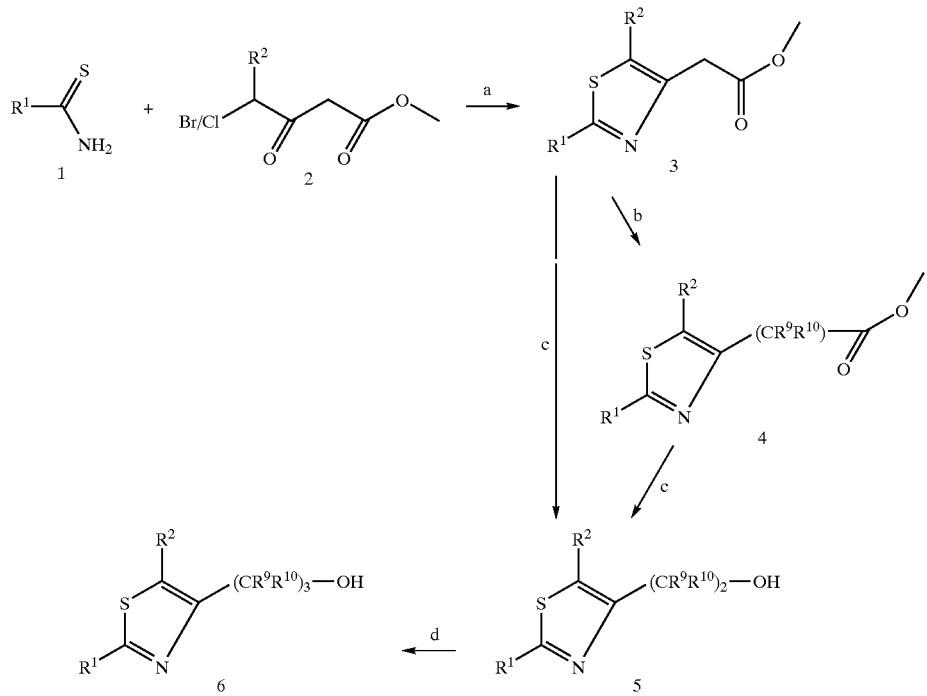

Thioamides 1 are known or can be prepared by methods known in the art, e.g. by treatment of the corresponding carboxamide with phosphorus pentasulfide or with Lawesson's Reagent [2,4-bis(4-methoxyphenyl)-1,3-dithia-2,4-diphosphetane-2,4-disulfide] in a solvent like toluene at temperatures preferably between 60° C. and the reflux temperature of the solvent Condensation of thioamides 1 with a suitable bis-electrophile, e.g. methyl 4-bromo- or 4-chloro-3-oxo-alkanoates 2, preferably in a solvent like toluene at elevated temperatures (e.g. at reflux temperature), gives thiazoles 3 carrying an acetic acid ester function at position 4 (step a) [compare PCT Int. Appl. (1997), WO97/31907 A1]. 4-Bromo-3-oxo-alkanoates 2 are known or can be prepared by methods known in the art [compare PCT Int. Appl. (2001), WO 01/79202 A1]. Thiazoles 3 can then be reduced, e.g. with lithium aluminum hydride in solvents like in ether or tetrahydrofuran, to thiazoles 5 with $R^9$=$R^{10}$=H (step c). Alternatively, alkyl groups $R^9$ and/or $R^{10}$ can be introduced into ester compounds 3 by treatment with a base like potassium tert-butoxide or sodium hydride in solvents like tetrahydrofuran or 1,2-dimethoxyethane followed by addition of one or sequentially two different alkyl halides, a reaction preferably performed between 0° C. and 80° C. (step b). Mono and/or dialkyl ester compounds 4 can be reduced to compounds 5 e.g. with lithium aluminium ing thiazoles 6 with an optionally substituted hydroxypropyl function attached to position 4 (step d). Alternatively, cyano intermediates of this elongation process can be reacted with alkyl Grignard reagents $R^9MgX$ in solvents like ether or tetrahydrofuran between 0° C. and the reflux temperature of the solvent to form the corresponding $R^9CO$— alkyl ketones which upon treatment with an alkyllithium reagent $R^{10}Li$ or lithium aluminium hydride in solvents like ether or tetrahydrofuran give alcohols 6 (step d). The alcohol compounds 5 or 6 which contain one or more chiral centers can optionally be separated into optically pure antipodes by methods well known in the art, e.g. chromatography on a chiral HPLC column or by derivatization with an optically pure acid to form esters, which can be separated by conventional HPLC chromatography and then be converted back to the original alcohol. The alcohol compounds 5 or 6 correspond to or can be converted into compounds of general formula 8 (scheme 1), 7 (scheme 2) or 1 (scheme 3) e.g. by treatment with methanesulfonyl chloride in dichloromethane in the presence of a base like triethylamine preferably in a temperature range between –20° C. and room temperature or e.g. by reaction with carbon tetrachloride or carbon tetrabromide and triphenylphosphine in solvents like tetrahydrofuran preferably in a temperature range between room temperature and the reflux temperature of the solvents.

Scheme 12

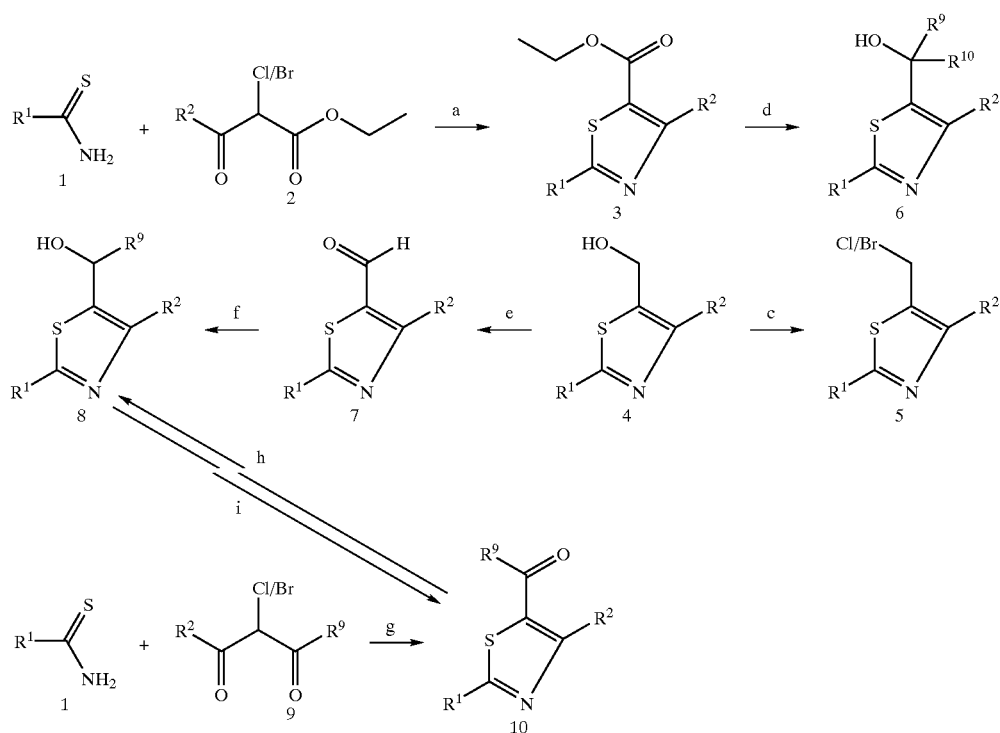

Thioamides 1 can be reacted with 2-halo acetoacetates 2 in solvents like ethanol, preferably at reflux temperature, to give thiazole-carboxylic esters 3 (step a). 2-Halo acetoacetates 2 are known or can be prepared by methods known in the art [compare PCT Int. Appl. (2002), WO 02/062774 A1]. Reduction of these esters 3, preferably using lithium aluminium hydride in a solvent like ether or tetrahydrofuran, preferably between 0° C. and room temperature, gives primary alcohols 4 (step b), which can be used as such or can be converted into the corresponding halides 5, e.g. by treatment with methanesulfonyl chloride in dichloromethane in the presence of 2,6-lutidine, preferably between −20° C. and the reflux temperature of dichloromethane [compare PCT Int. Appl. (2002), WO 02/28433], by treatment with thionyl chloride in a solvent like dichloromethane or chloroform preferably at temperatures between −20° C. and +50° C. or by treatment with tetrabromomethane, triphenylphosphine in solvents like tetrahydrofuran at temperatures between 0° C. and the reflux temperature of the tetrahydrofuran (step c). Esters 3 can be further converted into tertiary alcohols 6 with $R^9=R^{10}$ through reaction with alkyl organometallic reagents, preferably using alkyl Grignard compounds in a solvent like tetrahydrofuran or ether, preferably between −15° C. and the reflux temperature of the solvent [compare PCT Int. Appl. (2002), WO 02/062774 A1] (step d). Alkohols 6 with $R^9$ not equal to $R^{10}$ can be prepared by a sequential procedure: i) saponification to the acid; ii) treatment with $R^9$Li optionally in the presence of a Cu(I) salt in ether or tetrahydrofuran to yield the alkyl ketones —$COR^9$; iii) subsequent reaction with $R^{10}$Li or lithium aluminium hydride in ether or tetrahydrofuran (step d). Primary alcohols 4 can be oxidized to aldehydes 7 by methods known in the art, e.g. by treatment with pyridinium chlorochromate in dichloromethane, preferably at temperatures between room temperature and the reflux temperature of dichloromethane or by treatment with manganese dioxide in solvents like dichloromethane, preferably at room temperature (step e). These aldehydes 7 can be converted to the corresponding secondary alcohols 8 through reaction with alkyl organometallic compounds, preferably under the conditions given for the transformation of esters 3 to tertiary alcohols 6 (step f).

Reaction of thioamides 1 with 2-halo 1,3-diketones 9 in solvents like ethanol, preferably at reflux temperature, gives thiazole ketones 10 (step g). Alternatively, ketones 10 can be obtained from secondary alcohols 8 by methods known in the art, e.g. by treatment with Cr(VI) reagents like the Jones reagent (Jones et al., *J. Chem. Soc. 1953, 2548*) (step i). These ketones 10 can be reduced to the corresponding secondary alcohols 8 by methods known in the art, e.g. by treatment with sodium borohydride in alcohol, preferably at temperatures between −15° C. and 40° C. (step h). This reaction can also be carried out in stereoselective fashion leading to the (R)- or (S)-alcohols 8, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature according to Corey et al. (E. 1. Corey, R. K. Bakshi, S. Shibata, *J. Am. Chem. Soc.* 1987, 109, 5551–5553). If the alcohol compounds 4, 6, or 8 contains one or more chiral centers and are not optically pure, they can optionally be separated into optically pure antipodes by methods well known in the art, e.g. chromatography on a chiral HPLC column or by derivatization with an optically pure acid to form esters, which can be separated by conventional HPLC chromatography and then be converted back to the original alcohol.

The alcohol compounds 4, 6, and 8 and the halide compound 5 correspond to or can be converted into compounds of general formula 8 (scheme 1), 7 (scheme 2) or 1

(scheme 3) e.g. by treatment with methanesulfonyl chloride in dichloromethane in the presence of a base like triethylamine preferably in a temperature range between −20° C. and room temperature or e.g. by reaction with carbon tetrachloride or carbon tetrabromide and triphenylphosphine in solvents like tetrahydrofuran preferably in a temperature range between room temperature and the reflux temperature of the solvents.

sponding aldehydes using e.g. Swern conditions (oxalyl chloride/dimethylsulfoxide/triethylamine in dichloromethane, −78° C. to room temperature); ii) subsequent oxidation to the acid compounds 8 by using e.g. sodium chlorite in an alcohol like tert-butanol and water in the presence of $NaH_2PO_4$ and 2-methyl-2-butene preferably at room temperature (step e). Acid compounds 8 or the corresponding esters can be further transformed as described Scheme 13

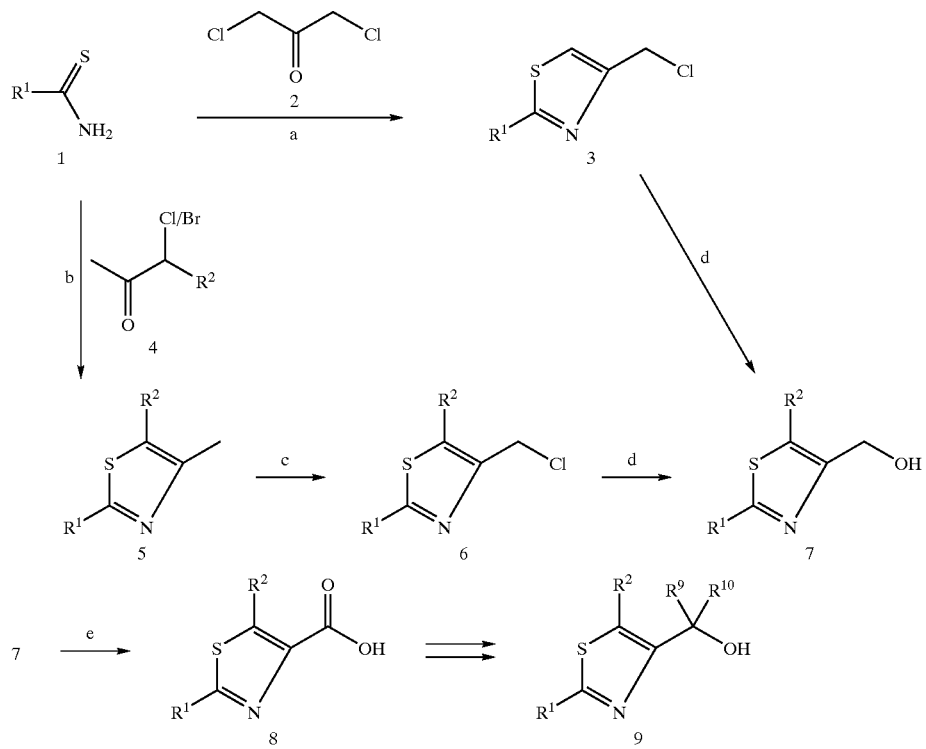

Thioamides 1 may be condensed with 1,3-dichloroacetone in solvents like acetone or acetonitrile between room temperature and the reflux temperature of the solvents, followed by treatment with a strong acid, e.g. concentrated sulfuric acid, preferably at ambient temperature leading to chloromethyl compounds 3 (step a). Alternatively, thioamides 1 are condensed with alpha-bromo or alpha-chloro ketones 4 in a solvent like ethanol, preferably at reflux temperature, to give aryl-thiazoles 5 bearing a methyl function at position 4 (step b) [compare Eur. Pat. Appl. (1987), EP 207453 A2]. By treatment of these aryl-thiazoles 5 with N-chlorosuccinimide in solvents like acetonitrile, preferably at reflux temperature, chloromethyl compounds 6 are obtained (step c) [compare PCT Int. Appl. (2001), WO 01/9805 A1]. Chloromethyl compounds 3 and 6 can be converted into hydroxymethyl compounds 7 e.g. by formation of the primary acetates (e.g. with acetic acid in the presence of sodium iodide, potassium carbonate at elevated temperature) and subsequent saponification (e.g. with lithium hydroxide in ethanol/water at room temperature) (step d). Hydroxymethyl compounds 7 can be oxidized in one step to the corresponding acids 8, e.g. by use of oxidizing agents like chromic acid, permanganate or nitric acid; alternatively, a two step procedure can be used: i) oxidation of the hydroxymethyl compounds 7 to the correfor esters 3 or the corresponding acids in scheme 12 to give the substituted alcohol compounds 9.

The alcohol compounds 7 and 9 and the halide compounds 3 and 6 correspond to or can be converted into compounds of general formula 8 (scheme 1), 7 (scheme 2) or 1 (scheme 3) e.g. by treatment with methanesulfonyl chloride in dichloromethane in the presence of a base like triethylamine preferably in a temperature range between −20° C. and room temperature or e.g. by reaction with carbon tetrachloride or carbon tetrabromide and triphenylphosphine in solvents like tetrahydrofuran preferably in a temperature range between room temperature and the reflux temperature of the solvents.

Scheme 14

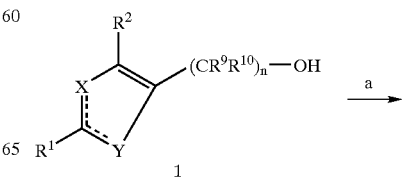

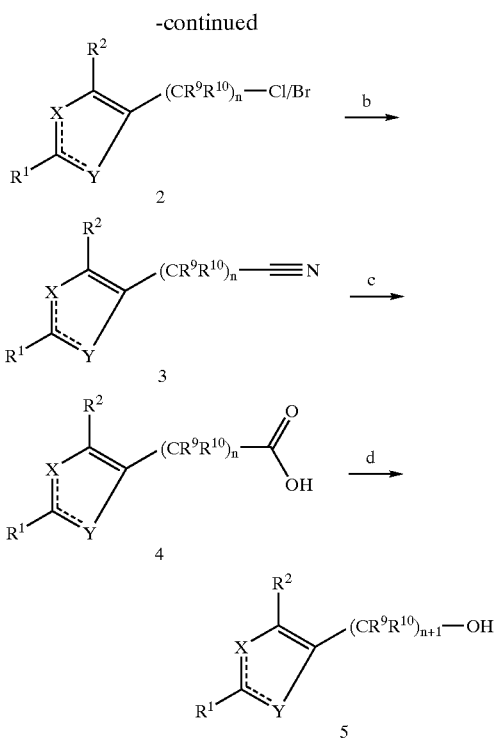

Aryl-thiazole alkanols 1 with a chain length of n carbon atoms can be converted into analogues with a chain length of n+1 carbon atoms by methods well known in the art, e.g. by conversion of the primary alcohol function into a suitable leaving group, e.g. a halide (step a), reaction with cyanide ion (step b), saponification (step c) followed by reduction of the acid formed (compounds 4) to the primary alcohols 5, e.g. by using diborane in tetrahydrofuran (step d). In order to introduce substituents $R^9$ and/or $R^{10}$ different from hydrogen, cyano intermediates 3 of this elongation process can be reacted with alkyl Grignard reagents $R^9MgX$ in solvents like ether or tetrahydrofuran between 0° C. and the reflux temperature of the solvents to form the corresponding $R^9CO$— alkyl ketones which upon treatment with an alkyllithium reagent $R^{10}Li$ or lithium aluminium hydride in solvents like ether or tetrahydrofuran give alcohols 5. $R^9CO$— alkyl ketones can also be reduced e.g. by treatment with sodium borohydride in alcohol, preferably at temperatures between −15° C. and 40° C. This reaction can also be carried out in stereoselective fashion leading to the (R)- or (S)-alcohols 5, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature according to Corey et al. (E. J. Corey, R. K. Bakshi, S. Shibata, *J. Am. Chem. Soc.* 1987, 109, 5551–5553). Alternatively, alcohol compounds 5 which contain one or more chiral centers can optionally be separated into optically pure antipodes by methods well known in the art, e.g. chromatography on a chrial HPLC column or by derivatization with an optically pure acid to form esters, which can be separated by conventional HPLC chromatography and then be converted back to the original alcohol. The alcohol compounds 5 correspond to or can be converted into compounds of general formula 8 (scheme 1), 7 (scheme 2) or 1 (scheme 3) e.g. by treatment with methanesulfonyl chloride in dichloromethane in the presence of a base like triethylamine preferably in a temperature range between −20° C. and room temperature or e.g. by reaction with carbon tetrachloride or carbon tetrabromide and triphenylphosphine in solvents like tetrahydrofuran preferably in a temperature range between room temperature and the reflux temperature of the solvents.

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112–119.

Full-length cDNA clones for human PPARα and mouse PPARγ were obtained by RT-PCR from human adipose and mouse liver cRNA, respectively, cloned into plasmid vectors and verified by DNA sequencing. (With respect to cloning of PPARα cDNA, see Sher, T. et al. "cDNA doning, chromosomel mapping and functional characterization of the human peroxisome proliferator activated receptor", Biochemistry 32(21) 5598–5604 (1993); with respect to cloning of PPARγ2 cDNA, see Tontonoy P., et al. "mPPAR gamma 2: tissue-specific regulator of an adipocyte enhancer", Genes Dev. 8(10) 1224–34 (1994).) Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assays

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction a 140 ng equivalent of GST-PPARα-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the recptor-coated beads was resolved in 50 ul of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-(4-(2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 ug SPA beads (PharmaciaArnersham) in a final volume of 50 ul by shaking. The resulting slurry was incubated for 1 h at RT and centrifuged for 2 min at 1300 g. The supernatant containing unbound protein was removed and the semidry pellet containing the recptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%O2:5%CO$_2$ atmosphere. Cells were seeded in 6 well plates at a density of $10^5$ Cells/well and then batch-transfected with either the pPA-PPARγ-LBD or pFA-PPARα-LBD expression plasmids plus a reporter plasmid and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^8$ is hydrogen) exhibit IC$_{50}$ values of 0.1 nM to 50 μM, preferably 1 nM to 10 μM for PPARα and PPARγ. The compounds further exhibit EC$_{50}$ values of 0.1 nM to 50 μM, preferably 1 nM to 10 μM for PPARα and PPARγ. Compounds, in which $R^8$ is not hydrogen are converted in vivo to compounds in which $R^8$ is hydrogen. The following table shows measured values for some selected compounds of the present invention and for a compound already known in the art (e.g.: Rosiglitazone, Drugs 1999, Vol 57(6), 921–930).

| | PPARα IC$_{50}$ | PPARγ IC$_{50}$ | PPARα EC$_{50}$ | PPARγ EC$_{50}$ |
|---|---|---|---|---|
| Example 5 | 133 nmol/l | 96 nmol/l | 400 nmol/l | 389 nmol/l |
| Example 14 | 109 nmol/l | 457 nmol/l | 77 nmol/l | 608 nmol/l |
| Example 19 | 89 nmol/l | 179 nmol/l | 71 nmol/l | 60 nmol/l |
| Example 20 | 24 nmol/l | 738 nmol/l | 27 nmol/l | 209 nmol/l |
| Example 25 | 370 nmol/l | 535 nmol/l | 116 nmol/l | 508 nmol/l |
| Example 43 | 50 nmol/l | 52 nmol/l | 2115 nmol/l | 543 nmol/l |
| Example 60 | 37 nmol/l | 42 nmol/l | 748 nmol/l | 411 nmol/l |
| Example 64 | 95 nmol/l | 84 nmol/l | 513 nmol/l | 281 nmol/l |
| Example 95 | 114 nmol/l | 925 nmol/l | 54 nmol/l | 1580 nmol/l |
| Example 102 | 15 nmol/l | 20 nmol/l | 215 nmol/l | 42 nmol/l |
| Rosiglitazone | inactive | 1090 nmol/l | inactive | 405 nmol/l |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) or their pharmaceutically acceptable salts, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsify agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1–500 mg, preferably 0.5–100 mg, of a compound of formula (I).

The following examples serve to illustrate the present invention in more detail. They are, however, not intended to limit its scope in any manner.

EXAMPLES

Abbreviations:

AcOEt=ethyl acetate, nBu$_2$BOTf=dibutylboron triflate, n-BuLi=n-butyllithium, DBAD=di-tert-butyl azodicarboxylate, DBU=1,8-diazabicyclo[5.4.0]undec-7-ene, DEAD=diethyl azodicarboxylate, DIAD=diisopropyl azodicarboxylate, DMPU=1,3-dimethyl-3,4,5,6-tetrahydro-2(1H)-pyrimidinone, eq.=equivalents, HPLC=high performance liquid chromatography, LDA=lithium diisopropylamide, POCl$_3$=phosphorous oxychloride, THF=tetrahydrofuran, TMAD=N,N,N',N'-tetramethyl azodicarboxamide.

Example 1 a] (3-(4-Benzyloxy-benzo[b]thiophen-7-yl)-2(Z,E)-ethoxy-acrylic acid ethyl ester 0.537 g (2.00 mmol) 4-Benzyloxy-benzo[b]thiophene-7-carbaldehyde [Ger. Offen. (1998) DE 19711617 A1] were dissolved under an argon atmosphere in 15 ml of 2-propanol. After cooling to −20° C., 0.944 g (2.20 mmol) (1,2-diethoxy-2-oxoethyl)triphenyl phosphonium chloride [Tetrahedron 50(25), 7543–56(1994)], and 0.415 g (3.00 mmol) of dry potassium carbonate were added. The resulting suspension was stirred in an ice bath and allowed to reach room temperature and stirred overnight at ambient temperature. A second addition of the same amounts of Wittig-reagent and potassium carbonate at −20° C. was performed as described above. After filtration and evaporation of the solvent, the residue was purified by flash chromatography (silica gel, hexane/AcOEt from 98:2 to 9:1) giving 0.586 g (77% of theory) of 3-(4-benzyloxy-benzo[b]thiophen-7-yl)-2(Z,E)-ethoxy-acrylic acid ethyl ester as a light yellow oil.

MS: 382.2 (M)$^+$, 291.2, 189.1.

b] [rac]3-(4-Benzyloxy-benzo[b]thiophen-7-yl)-2-ethoxy-propionic acid methyl ester 0.383 g (1.00 mmol) 3-(4-Benzyloxy-benzo[b]thiophen-7-yl)-2(Z,E)-ethoxy-acrylic ethyl ester were dissolved under an argon atmosphere in 20 ml THF/MeOH (1:1). 0.248 g (10.2 mmol) of magnesium were added and the reaction mixture then warmed up to 50° C. After 30 minutes, it was cooled down to room temperature and stirred overnight at ambient temperature. After addition of 5 ml HCl (25% in water) at 25° C., the reaction mixture was stirred vigorously for one hour, then extracted with AcOEt (three times); the organic phases were washed with brine, dried over MgSO$_4$, filtered and evaporated. Purification of the yellow oil by flash chromatography (silica gel, hexane/AcOEt from 9:1 to 4:1) afforded 0.366 g (99% of theory) of [rac]-3-(4-benzyloxy-benzo[b]thiophen-7-yl)-2-ethoxy-propionic acid methyl ester as a yellowish oil.

MS: 370.1 (M)$^+$, 311.2, 253.1.

c] [rac]-2-Ethoxy-3-(4-hydroxy-benzo[b]thiophen-7-yl)-propionic acid methyl ester 4.68 g (12.6 mmol) [rac]-3-(4-Benzyloxy-benzo[b]thiophen-7-yl)-2-ethoxy-propionic acid methyl ester were dissolved under an argon atmosphere in 150 ml dichloromethane at room temperature. 23.9 ml Dimethyl sulfide and 16.03 ml boron trifluoride diethyl etherate were added drop by drop. After 5 hours stirring at room temperature, the reaction mixture was quenched by pouring it into crashed ice/water, then extracted three times with dicloromethane. The organic phases were washed with brine, dried over MgSO$_4$, filtered and evaporated to afford 4.92 g of a yellow oil. Purification by flash chromatography (silica gel, hexane, CH$_2$Cl$_2$ and MeOH) gave 3.51 g (99% of theory) of [rac]-2-ethoxy-3-(4-hydroxy-benzo[b]thiophen-7-yl)-propionic acid methyl ester as light yellow solid.

MS: 279.1 (M−H)$^-$.

d] [rac]-2-Ethoxy-3-{4-[2-(5-methyl-2-phenyl-thiazol-4-yl)-ethoxy]-benzo[b]thiophen-7-yl}-propionic acid methyl ester 0.282 g (1.28 mmol) of 2-(5-methyl-2-phenyl-thiazol-4-yl)-ethanol [PCT Int. Appl. (2002), WO 02/18355 A1] were dissolved in 12 ml THF and treated successively at 0° C. with 0.30 g (1.07 mmol) of [rac]-2-ethoxy-3-(4-hydroxy-benzo[b]thiophen-7-yl)-propionic acid methyl ester, 0.397 g (1.50 mmol) of triphenylphosphine, and 0.32 g (1.39 mmol) of DIAD (diisopropyl azodicarboxylate). The cooling bath was then removed and stirring continued for 6 hours. Afterwards, the reaction mixture was evaporated to dryness in vacuo. Flash chromatography (SiO$_2$, hexane/AcOEt), followed by evaporation, delivered 0.474 g (92% of theory) of [rac]-2-ethoxy-3-{4-[2-(5-methyl-2-phenyl-thiazol-4-yl)-ethoxy]-benzo[b]thiophen-7-yl}-propionic acid methyl ester as colorless viscous oil.

MS: 482.4 (M+H)$^+$.

e] [rac]-2-Ethoxy-3-{4-[2-(5-methyl-2-phenyl-thiazol-4-yl)-ethoxy]-benzo[b]thiophen-7-yl}-propionic acid 0.465 g (0.97 mmol) of [rac]-2-ethoxy-3-{4-[2-(5-methyl-2-phenyl-thiazol-4-yl)-ethoxy]-benzo[b]thiophen-7-yl}-propionic acid methyl ester were dissolved in 10 ml of dioxane; 1.65 ml of a 1N LiOH-solution in water (1.65 mmol) were then added slowly at room temperature. The resulting mixture was stirred for 5 hours at room temperature and then poured onto ice, neutralized to pH 4 with HCl (1N) and extracted 2 times with dichloromethane. The combined organic phases were washed with water, dried over magnesium sulfate and evaporated. Flash chromatography (SiO$_2$, MeCl$_2$/MeOH), followed by evaporation, delivered 0.200 g (39% of theory) of [rac]-2-ethoxy-3-{4-[2-(5-methyl-2-phenyl-thiazol-4-yl)-ethoxy]-benzo[b]thiophen-7-yl}-propionic acid as colorless viscous oil. MS: 466.2 (M−H)$^-$.

Example 2 a] 4-Benzyloxy-5,6,7,8-tetrahydro-naphthalene-1-carbaldehyde g (4.20 mmol) of 5-benzyloxy-1,2,3,4-tetrahydro-naphthalene [J. Org. Chem. (2001), 66(5), 1775–1780] and 0.765 ml (8.39 mmol) of dichloromethyl methyl ether were dissolved in 25 ml of dichloromethane. This solution was cooled down to 0° C., and 2.35 ml (20.98 mmol) of titanium tetrachloride were added slowly. The resulting dark solution was stirred at 0° C. for 30 minutes, and then 2.0 ml of HCl (25% in water) were added slowly at <5° C. The mixture was stirred for 30 minutes at 0° C., the 2 phases were separated and the aqueous phase was extracted 3 times with dichloromethane. The combined organic phases were dried over $MgSO_4$ and evaporated to afford 1.40 g of a light red oil. Flash chromatography (silica gel, cyclohexane/ethyl acetate=95:5, then cyclohexane/ethyl acetate=9:1) left finally 0.73 g (65% of theory) of 4-benzyloxy-5,6,7,8-tetrahydro-naphthalene-1-carbaldehyde as yellow solid.

MS: 266.2 ($M^+$), 91.2.

b] 3-(4-Benzyloxy-5,6,7,8-tetrahydro-naphthalen-1-yl)-2(Z,E)-ethoxy-acrylic acid methyl ester and 3-(4-benzyloxy-5,6,7,8-tetrahydro-naphthalen-1-yl)-2(Z,E)-ethoxy-acrylic acid ethyl ester In analogy to the procedure described in example 1 a], 4-benzyloxy-5,6,7,8-tetrahydro-naphthalene-1-carbaldehyde was reacted with (1,2-diethoxy-2-oxoethyl) triphenyl phosphonium chloride [Tetrahedron 50(25), 7543–56(1994)] to yield 3-(4-benzyloxy-5,6,7,8-tetrahydro-naphthalen-1-yl)-2(Z,E)-ethoxy-acrylic acid methyl ester as colorless solid together with a minor amount of 3-(4-benzyloxy-5,6,7,8-tetrahydro-naphthalen-1-yl)-2(Z,E)-ethoxy-acrylic acid ethyl ester as colorless solid (the use of methanol during the work-up process caused the transesterification observed).

MS (methyl ester): 367.3 $(M+H)^+$.
MS (ethyl ester): 381.4 $(M+H)^+$.

c] [rac]-2-Ethoxy-3-(4-hydroxy-5,6,7,8-tetrahydro-naphthalen-1-yl)-propionic acid methyl ester 2.5 g of Pd/C (10%) were added under argon to 12.5 g (34.1 mmol) of 3-(4-benzyloxy-5,6,7,8-tetrahydro-naphthalen-1-yl)-2(Z,E)-ethoxy-acrylic acid methyl ester dissolved in 180 ml of methanol. The atmosphere was then replaced with $H_2$, and the suspension was rapidly stirred at room temperature for 2 hours. Filtration over dicalite and evaporation of the solvents left 9.25 g of a dark brown oil. Flash chromatography (silica gel, hexane/ethyl acetate=9:1) finally gave 7.40 g (78% of theory) of [rac]-2-ethoxy-3-(4-hydroxy-5,6,7,8-tetrahydro-naphthalen-1-yl)-propionic acid methyl ester as yellow oil. MS: 277.2 $(M-H)^-$.

d] [rac]-2-Ethoxy-3-{4-[2-(5-methyl-2-phenyl-thiazol-4-yl)-ethoxy]-5,6,7,8-tetrahydro-naphthalen-1-yl}-propionic acid methyl ester In analogy to the procedure described in example 1 d], [rac]-2-ethoxy-3-(4-hydroxy-5,6,7,8-tetrahydro-naphthalen-1-yl)-propionic acid methyl ester was reacted with 2-(5-methyl-2-phenyl-thiazol-4-yl)-ethanol [PCT Int. Appl. (2002), WO 02/18355 A1] in tetrahydrofuran in the presence of triphenylphosphine and DIAD (diisopropyl azodicarboxylate) to yield [rac]-2-ethoxy-3-{4-[2-(5-methyl-2-phenyl-thiazol-4-yl)-ethoxy]-5,6,7,8-tetrahydro-naphthalen-1-yl}-propionic acid methyl ester as colorless viscous oil.

MS: 480.5 $(M+H)^+$.

e] [rac]-2-Ethoxy-3-{4-[2-(5-methyl-2-phenyl-thiazol-4-yl)-ethoxy]-5,6,7,8-tetrahydro-naphthalen-1-yl}-propionic acid In analogy to the procedure described in example 1 e], [rac]-2-ethoxy-3-{4-[2-(5-methyl-2-phenyl-thiazol-4-yl)-ethoxy]-5,6,7,8-tetrahydro-naphthalen-1-yl}-propionic acid methyl ester was saponified to yield [rac]-2-ethoxy-3-{4-[2-(5-methyl-2-phenyl-thiazol-4-yl)-ethoxy]-5,6,7,8-tetrahydro-naphthalen-1-yl]-propionic acid as colorless amorphous solid.

MS: 464.2 $(M-H)^-$.

Example 3 a] [rac]-2-Ethoxy-3-(7-hydroxy-benzo[b]thiophen-4-yl)-propionic acid methyl ester In analogy to the procedure described in example 2 a], 7-benzyloxy-benzo[b]thiophene (prepared from benzo[b]thiophen-7-ol [J. Chem. Soc., Perkin Trans. 1 (1983), (12), 2973–71 and benzylchloride by treatment with potassium carbonate in N,N-dimethylformamide at room temperature) was reacted with dichloromethyl methyl ether in dichloromethane at 0° C. to give 7-benzyloxy-benzo[b]thiophene-4-carbaldehyde.

Treatment of 7-benzyloxy-benzo[b]thiophene-4-carbaldehyde with (1,2-diethoxy-2-oxoethyl)triphenyl phosphonium chloride and potassium carbonate in 2-propanol in analogy to the procedure described in example 1 a] gave 3-(7-benzyloxy-benzo[b]thiophen-4-yl)-2(Z,E)-ethoxy-acrylic acid ethyl ester. Reduction of 3-(7-benzyloxy-benzo[b]thiophen-4-yl)-2(Z,E)-ethoxy-acrylic acid ethyl ester with magnesium in THF/MeOH (1:1) at 50° C. in analogy to the procedure described in example 1 b], yielded [rac]-3-(7-benzyloxy-benzo[b]thiophen-4-yl)-2-ethoxy-propionic acid methyl ester; subsequent removal of the benzyl protective function with dimethyl sulfide and boron trifluoride diethyl etherate in dichlormethane at room temperature in analogy to the procedure described in example 1 c], gave [rac]-2-ethoxy-3-(7-hydroxy-benzo[b]thiophen-4-yl)-propionic acid methyl ester as light yellow oil.

MS: 279.0 $(M-H)^-$.

b] [rac]-2-Ethoxy-3-{7-[2-(5-methyl-2-phenyl-thiazol-4-yl)-ethoxy]-benzo[b]thiophen-4-yl}-propionic acid methyl ester In analogy to the procedure described in example 1 d], [rac]-2-ethoxy-3-(7-hydroxy-benzo[b]thiophen-4-yl)-propionic acid methyl ester was reacted with 2-(5-methyl-2-phenyl-thiazol-4-yl)-ethanol [PCT Int. Appl. (2002), WO 02/18355 A1] in tetrahydrofuran in the presence of triphenylphosphine and DIAD (diisopropyl azodicarboxylate) to yield [rac]-2-ethoxy-3-{7-[2-(5-methyl-2-phenyl-thiazol-4-yl)-ethoxy]-benzo[b]thiophen-4-yl}-propionic acid methyl ester as colorless viscous oil.

MS: 482.4 $(M+H)^+$.

c] [rac]-2-Ethoxy-3-{7-[2-(5-methyl-2-phenyl-thiazol-4-yl)-ethoxy]-benzo[b]thiophen-4-yl}-propionic acid In analogy to the procedure described in example 1 e], [rac]-2-ethoxy-3-{7-[2-(5-methyl-2-phenyl-thiazol-4-yl)-ethoxy]-benzo[b]thiophen-4-yl}-propionic acid methyl ester was saponified to yield [rac]-2-ethoxy-3-{7-[2-(5-methyl-2-phenyl-thiazol-4-yl)-ethoxy]-benzo[b]thiophen-4-yl}-propionic acid as colorless amorphous solid.

MS: 466.2 $(M-H)^-$.

Example 4 a] 2-(4-tert-Butyl-phenyl)-4-chloromethyl-thiazole

A mixture of 6.0 g of 4-tert-butyl-thiobenzamide (31 mmol) and 5.24 g of 1,3-dichloroacetone (41.3 mmol), dissolved in 20 ml of acetone, was stirred at room temperature for 5 hours and at reflux for 2 hours. After cooling to room temperature, the solid compound formed was collected and dried. Afterwards, it was dissolved in 20 ml of concentrated sulfuric acid and the homogenous mixture was stirred for 15 minutes at ambient temperature. The reaction mixture was then poured onto crushed ice and the 2-(4-tert-butyl-phenyl)-4-chloromethyl-thiazole was extracted with two 50 ml portions of tert-butyl methyl ether. The combined organic phases were washed with water and with brine, dried over anhydrous sodium sulfate and evaporated, leaving 6.65 g (60.5% of theory) of a colorless viscous oil which solidified upon standing.

MS: 266.3 $(M+H)^+$.

b] 3-(4-Benzyloxy-3-methyl-phenyl)-2(Z,E)-ethoxy-acrylic acid ethyl ester

In analogy to the procedure described in example 1 a], 4-benzyloxy-3-methyl-benzaldehyde [PCT Int. Appl. (2001), WO 0140172 A1] was reacted with (1,2-diethoxy-2-oxoethyl)triphenyl phosphonium chloride (Tetrahedron 50 (25), 7543–56 (1994)] to yield 3-(4-benzyloxy-3-methyl-phenyl)-2(Z,E)-ethoxy-acrylic acid ethyl ester as light yellow oil.

MS: 340.2 (M$^+$).

c] [rac]-2-Ethoxy-3-(4-hydroxy-3-methyl-phenyl)-propionic acid ethyl ester 0.7 g of Pd/C were added under argon to a solution of 7.3 g of 3-(4-benzyloxy-3-methyl-phenyl)-2(Z,E)-ethoxy-acrylic acid ethyl ester (21.4 mmol) in 10 ml of tetrahydrofuran. The atmosphere was then replaced with H$_2$, and the suspension was rapidly stirred at room temperature for four hours. Filtration over dicalite and evaporation of the solvent left 4.3 g (79.4% of theory) of [rac]-2-ethoxy-3-(4-hydroxy-3-methyl-phenyl)-propionic acid ethyl ester as colorless viscous oil.

MS: 252.2 (M$^+$), 206.2 (M$^+$-EtOH).

d] [rac]-3-{4-[2-(4-tert-Butyl-phenyl)-thiazol-4-ylmethoxy]-3-methyl-phenyl}-2-ethoxy-propionic acid ethyl ester A mixture of 150 mg of [rac]-2-ethoxy-3-(4-hydroxy-3-methyl-phenyl)-propionic acid ethyl ester (0.59 mmol), 190 mg of 2-(4-tert-butyl-phenyl)-4-chloromethyl-thiazole (0.71 mmol) and 325 mg of cesium carbonate (1 mmol) in 5 ml of acetonitrile was stirred at 60° C. for 1 h. The solvent was then evaporated and the residue obtained was chromatographed on silicagel using a 98:2 (v/v) mixture of dichloromethane and diethyl ether as the eluent. Thus, 150 mg (52% of theory) of [rac]-3-{4-[2-(4-tert-butyl-phenyl)-thiazol-4-ylmethoxy]-3-methyl-phenyl}-2-ethoxy-propionic acid ethyl ester was obtained as a colorless viscous oil.

MS: 482.4 (M+H)$^+$.

e] [rac]-3-{4-[2-(4-tert-Butyl-phenyl)-thiazol-4-ylmethoxy]-3-methyl-phenyl}-2-ethoxy-propionic acid 140 mg of [rac]-3-{4-[2-(4-tert-butyl-phenyl)-thiazol-4-ylmethoxy]-3-methyl-phenyl}-2-ethoxy-propionic acid ethyl ester (0.29 mmol) were dissolved in 5 ml of methanol; 1 ml of a 2N aqueous lithium hydroxide solution was added and the reaction mixture was stirred at 55° C. for 1 h. After cooling to room temperature, 1 ml of a 2N aqueous hydrochloric acid solution and 0.5 ml of a saturated solution of potassium hydrogen sulfate were added. The reaction mixture was then extracted with two 10 ml portions of dichloromethane. The combined organic phases were washed with brine, dried over anhydrous sodium sulfate and evaporated, leaving 130 mg (98.6% of theory) of [rac]-3-{4-[2-(4-tert-butyl-phenyl)-thiazol-4-ylmethoxy]-3-methyl-phenyl}-2-ethoxy-propionic acid as a colorless solid.

MS: 452.3 (M–H)$^-$.

Example 5 a] [rac]-2-Ethoxy-3-{4-[2-(4-isopropyl-phenyl)-thiazol-4-ylmethoxy]-3-methyl-phenyl}-propionic acid In analogy to the procedure described in example 4 d], [rac]-2-ethoxy-3-(4-hydroxy-3-methyl-phenyl)-propionic acid ethyl ester (example 4 c]) was reacted with 4-chloromethyl-2-(4-isopropyl-phenyl)-thiazole (prepared from 4-isopropyl-thiobenzamide and 1,3-dichloroacetone in analogy to the procedure described in example 4 a]) in acetonitrile in the presence of cesium carbonate to yield [rac]-2-ethoxy-3-{4-[2-(4-isopropyl-phenyl)-thiazol-4-ylmethoxy]-3-methyl-phenyl}-propionic acid ethyl ester, which was further saponified in analogy to the procedure described in example 4 e], to yield [rac]-2-ethoxy-3-{4-[2-(4-isopropyl-phenyl)-thiazol-4-ylmethoxy]-3-methyl-phenyl}-propionic acid as colorless gum.

MS: 438.2 (M–H)$^-$.

Example 6 a] [rac]-2-Ethoxy-3-{3-methyl-4-[2-(4-trifluoromethyl-phenyl)-thiazol-4-ylmethoxy]-phenyl}-propionic acid In analogy to the procedure described in example 4 d], [rac]-2-ethoxy-3-(4-hydroxy-3-methyl-phenyl)-propionic acid ethyl ester (example 4 c]) was reacted with 4-chloromethyl-2-(4-trifluoromethyl-phenyl)-thiazole (prepared from 4-trifluoromethyl-thiobenzamide and 1,3-dichloroacetone in analogy to the procedure described in example 4 a]) in acetonitrile in the presence of cesium carbonate to yield [rac]-2-ethoxy-3-{3-methyl-4-[2-(4-trifluoromethyl-phenyl)-thiazol-4-ylmethoxy]-phenyl}-propionic acid ethyl ester, which was further saponified in analogy to the procedure described in example 4 e], to yield [rac]-2-ethoxy-3-{3-methyl-4-[2-(4-trifluoromethyl-phenyl)-thiazol-4-ylmethoxy]-phenyl}-propionic acid as colorless gum.

MS: 464.1 (M–H)$^-$.

Example 7 a] [rac]-2-Ethoxy-3-(3-fluoro-4-hydroxy-phenyl)-propionic acid ethyl ester

In analogy to the procedure described in example 1 a], 4-benzyloxy-3-fluoro-benzaldehyde [prepared from 3-fluoro-4-hydroxy-benzaldehyde and benzyl bromide, cesium carbonate in acetonitrile] was reacted with (1,2-diethoxy-2-oxoethyl)triphenyl phosphonium chloride [Tetrahedron 50 (25), 7543–56 (1994)] to yield 3-(4-benzyloxy-3-fluoro-phenyl)-2(Z,E)-ethoxy-acrylic acid ethyl ester. Hydrogenation of 3-(4-benzyloxy-3-fluoro-phenyl)-2(Z,E)-ethoxy-acrylic acid ethyl ester as described in example 4 c] yielded [rac]-2-ethoxy-3-(3-fluoro-4-hydroxy-phenyl)-propionic acid ethyl ester as colorless viscous oil.

MS: 255.0 (M–H)$^-$.

b] [rac]-3-{4-[2-(4-tert-Butyl-phenyl)-thiazol-4-ylmethoxy]-3-fluoro-phenyl}-2-ethoxy-propionic acid In analogy to the procedure described in example 4 d], [rac]-2-ethoxy-3-(3-fluoro-4-hydroxy-phenyl)-propionic acid ethyl ester was reacted with 2-(4-tert-butyl-phenyl)-4-chloromethyl-thiazole (example 4 a]) in acetonitrile in the presence of cesium carbonate to yield [rac]-3-{4-[2-(4-tert-butyl-phenyl)-thiazol-4-ylmethoxy]-3-fluoro-phenyl}-2-ethoxy-propionic acid ethyl ester, which was further saponified in analogy to the procedure described in example 4 e], to yield [rac]-3-{4-[2-(4-tert-butyl-phenyl)-thiazol-4-ylmethoxy]-3-fluoro-phenyl}-2-ethoxy-propionic acid as colorless solid.

MS: 456.3 (M–H)$^-$.

Example 8 a] [rac]-2-Ethoxy-3-{3-fluoro-4-[2-(4-trifluoromethyl-phenyl)-thiazol-4-ylmethoxy]-phenyl}-propionic acid In analogy to the procedure described in example 4 d], [rac]-2-ethoxy-3-(3-fluoro-4-hydroxy-phenyl)-propionic acid ethyl ester (example 7 a]) was reacted with 4-chloromethyl-2-(4-trifluoromethyl-phenyl)-thiazole (prepared from 4-trifluoromethyl-thiobenzamide and 1,3-dichloroacetone in analogy to the procedure described in example 4 a]) in acetonitrile in the presence of cesium carbonate to yield [rac]-2-ethoxy-3-{3-fluoro-4-[2-(4- trifluoromethyl-phenyl)-thiazol-4-ylmethoxy]-phenyl}-propionic acid ethyl ester, which was further saponified in analogy to the procedure described in example 4 e], to yield [rac]-2-ethoxy-3-{3-fluoro-4-[2-(4-trifluoromethyl-phenyl)-thiazol-4-ylmethoxy]-phenyl}-propionic acid as colorless solid.

MS: 468.1 (M–H)⁻.

Example 9 a] [rac]-2-Ethoxy-3-{3-fluoro-4-[2-(4-isopropyl-phenyl)-thiazol-4-ylmethoxy]-phenyl}-propionic acid In analogy to the procedure described in example 4 d], [rac]-2-ethoxy-3-(3-fluoro-4-hydroxy-phenyl)-propionic acid ethyl ester (example 7 a]) was reacted with 4-chloromethyl-2-(4-isopropyl-phenyl)-thiazole (prepared from 4-isopropyl-thiobenzamide and 1,3-dichloroacetone in analogy to the procedure described in example 4 a]) in acetonitrile in the presence of cesium carbonate to yield [rac]-2-ethoxy-3-{3-fluoro-4-[2-(4-isopropyl-phenyl)-thiazol-4-ylmethoxy]-phenyl}-propionic acid ethyl ester, which was further saponified in analogy to the procedure described in example 4 e], to yield [rac]-2-ethoxy-3-{3-fluoro-4-[2-(4-isopropyl-phenyl)-thiazol-4-ylmethoxy]-phenyl}-propionic acid as colorless solid.

MS: 442.2 (M–H)⁻.

Example 10 a] 3-(4-Benzyloxy-2-methyl-phenyl)-2(Z,E)-ethoxy-acrylic acid ethyl ester

A suspension of (1,2-diethoxy-2-oxoethyl)triphenyl phosphonium chloride [Tetrahedron 50(25), 7543–56(1994)] (35.5 g, 82.9 mmol) and DBU (13.6 ml, 91.2 mmol) in THF (60 ml) was stirred for 10 min at ambient temperature. 4-Benzyloxy-2-methyl-benzaldehyde (12.5 g, 55.2 mmol) was added and the reaction mixture was heated under reflux for 16 h. The solvent was concentrated at reduced pressure, the residue was taken up in AcOEt and washed with saturated aqueous $NH_4Cl$ solution and brine. The organic layer was dried over sodium sulfate, the solvent removed under reduced pressure and the residue purified by column chromatography (silica gel, hexane/AcOEt) to give 14.5 g (42.6 mmol, 77%) of the title compound as yellow liquid.

MS: 340.2 (M)⁺, 249.2, 147.1, 91.1.

b] [rac]-2-Ethoxy-3-(4-hydroxy-2-methyl-phenyl)-propionic acid ethyl ester

A solution of 3-(4-benzyloxy-2-methyl-phenyl)-2(Z,E)-ethoxy-acrylic acid ethyl ester (1 g, 2.9 mmol) in ethanol (50 ml) was hydrogenated over 10% palladium on charcoal (250 mg) at ambient temperature for 2 h. The catalyst was filtered off and the solvent evaporated under reduced pressure to give 600 mg (2.4 mmol, 81%) of the title compound as yellow liquid which was used in the next step without further purification.

MS: 270.4 (M+$NH_4$)⁺, 253 (M)⁺, 207.2, 165.3.

c] [rac]-2-Ethoxy-3-(2-methyl-4-{2-[5-methyl-2-(4-trifluoromethyl-phenyl)-thiazol-4-yl]-ethoxy}-phenyl)-propionic acid ethyl ester To a ice cold solution of [rac]-2-ethoxy-3-(4-hydroxy-2-methyl-phenyl)-propionic acid ethyl ester (50 mg, 0.2 mmol), 2-[5-methyl-2-(4-trifluoromethyl-phenyl)-thiazol-4-yl]-ethanol (85 mg, 0.3 mmol) [PCT Int. Appl. (2001), WO 01/00603 A1] and triphenylphosphine (78 mg, 0.3 mmol) in dichloromethane (2 ml) was added diethyl azodicarboxylate (46 μl, 0.3 mmol). The cooling bath was removed and stirring continued for 6 h. Evaporation of the solvent under reduced pressure gave an orange oil which was purified by column chromatography (silica gel, cyclohexane/AcOEt) to give 34 mg (70 μmol, 33%) of the title compound as colorless oil.

MS: 522.2 (M+H)⁺, 476.2, 448.2, 270.2.

d] [rac]-2-Ethoxy-3-(2-methyl-4-{2-[5-methyl-2-(4-trifluoromethyl-phenyl)-thiazol-4-yl]-ethoxy}-phenyl)-propionic acid To a solution of [rac]-2-ethoxy-3-(2-methyl-4-{2-[5-methyl-2-(4-trifluoromethyl-phenyl)-thiazol-4-yl]-ethoxy}-phenyl)-propionic acid ethyl ester (34 mg, 70 μmol) in THF/methanol 2/1 (750 μl) was added a 1 N aqueous LiOH solution (390 μl, 420 μmol). The reaction mixture was stirred for 1.5 h at ambient temperature, neutralized with 1 N aqueous HCl solution under ice cooling and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the tide compound (30 mg, 6 μmol, 93%) as colorless solid.

MS: 494.1 (M+H)⁺, 448.2, 420.2, 288.2, 270.2.

Example 11 a] [rac]-2-Ethoxy-3-{2-methyl-4-[2-(5-methyl-2-phenyl-thiazol-4-yl)-ethoxy]-phenyl}-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-(5-methyl-2-phenyl-thiazol-4-yl)-ethanol [PCT Int. Appl. (2002), WO 02/18355 A1] in the presence of triphenylphosphine and diethyl azodicarboxylate to yield [rac]-2-ethoxy-3-{2-methyl-4-[2-(5-methyl-2-phenyl-thiazol-4-yl)-ethoxy]-phenyl}-propionic acid ethyl ester as colorless oil.

MS: 454.3 (M+H)⁺, 426.3, 370.2, 342.3, 279.2, 202.1.

b] [rac]-2-Ethoxy-3-{2-methyl-4-[2-(5-methyl-2-phenyl-thiazol-4-yl)-ethoxy]-phenyl}-propionic acid In analogy to the procedure described in example 10 d], [rac]-2-ethoxy-3-{2-methyl-4-[2-(5-methyl-2-phenyl-thiazol-4-yl)-ethoxy]-phenyl}-propionic acid ethyl ester was treated with LiOH to obtain [rac]-2-ethoxy-3-{2-methyl-4-[2-(5-methyl-2-phenyl-thiazol-4-yl)-ethoxy]-phenyl}-propionic acid as colorless solid.

MS: 424.3 (M–H)⁻, 378.1, 329.1, 260.8.

Example 12 a] [2-(4-tert-Butyl-phenyl)-5-methyl-thiazol-4-yl]-acetic acid methyl ester 6.75 g (32.3 mmol) of [rac]-4-bromo-3-oxo-pentanoic acid methyl ester [PCT Int. Appl. (2001), WO 01/79202] and 5.0 g (25.9 mmol) of 4-tert-butyl-thiobenzamide were dissolved in 10 ml of acetone and the mixture was heated at reflux for 1 h. The solvent was evaporated. In order to reesterificate the acid which was formed during the reaction, the residue was dissolved in 25 ml of methanol, 0.25 g of para-toluene sulfonic acid mono-hydrate and 5 ml of trimethyl orthoformate were added and the mixture was heated at reflux for 2 hours. After cooling to room temperature, a solution of 3 g of potassium hydrogencarbonate in $H_2O$ was added. Afterwards, most of the methanol was distilled off and the residue was extracted with tert-butyl methyl ether. After evaporation of the solvent, the residue was chromatographed on silicagel with dichloromethane as eluent. 6.2 g (79% of theory) of 2-(4-tert-butyl-phenyl)-5-methyl-thiazol-4-yl]-acetic acid methyl ester were obtained as yellow solid.

MS: 303.1 (M⁺).

b] 2-[2-(4-tert-Butyl-phenyl)-5-methyl-thiazol-4-yl-ethanol

A solution of 6.2 g of 2-(4-tert-butyl-phenyl)-5-methyl-thiazol-4-yl]-acetic acid methyl ester (20.4 mmol) in 20 ml of THF was added to a suspension of 0.93 g (24.5 mmol) of lithium aluminium hydride, under an argon atmosphere, at 0–5° C. Afterwards, the mixture was stirred at ambient temperature for 1 hour, treated cautiously with a small amount of $H_2O$ followed by 50 ml of ethyl acetate and 20 g of anhydrous sodium sulfate and stirring was continued for 0.5 hours. Then, the reaction mixture was filtered, the filtrate was evaporated, leaving 5.5 g (97% of theory) of 2-[2-(4-tert-butyl-phenyl)-5-methyl-thiazol-4-yl]-ethanol as colorless solid.

MS: 276.2 $(M+H)^+$.

c] [rac]-3-(4-{2-[2-(4- tert-Butyl-phenyl)-5-methyl-thiazol-4-yl]-ethoxy}-2-methyl-phenyl-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(4-tert-butyl-phenyl)-5-methyl-thiazol-4-yl]-ethanol in the presence of triphenylphosphine and diethyl azodicarboxylate to yield [rac]-3-(4-{2-[2-(4-tert-butyl-phenyl)-5-methyl-thiazol-4-yl]-ethoxy}-2-methyl-phenyl)-2-ethoxy-propionic acid ethyl ester as colorless oil.

MS: 510.4 $(M+H)^+$, 464.2, 436.3, 258.2.

d] [rac]-3-{4-{2-[2-(4-tert-Butyl-phenyl)-5-methyl-thiazol-4-yl]-ethoxy}-2-methyl-phenyl)-2-ethoxy-propionic acid In analogy to the procedure described in example 10 d1, [rac]-3-(4-{2-[2-(4-tert-butyl-phenyl)-5-methyl-thiazol-4-yl]-ethoxy}-2-methyl-phenyl)-2-ethoxy-propionic acid ethyl ester was treated with LiOH to obtain [rac]-3-(4-{2-[2-(4-tert-butyl-phenyl)-5-methyl-thiazol-4-yl]-ethoxy}-2-methyl-phenyl)-2-ethoxy-propionic acid as colorless liquid.

MS: 482.3 $(M+H)^+$, 430.3, 408.3, 371.3, 323.3, 276.2, 258.2.

Example 13 a] [2-(4-Isopropyl-phenyl)-thiazol-4-yl]-acetonitrile 14.5 g (57.6 mmol) of 4-chloromethyl-2-(4-isopropyl-phenyl)-thiazole (prepared from 4-isopropyl-thiobenzamide and 1,3-dichloroacetone in analogy to the procedure described in example 4 a]) and 4.08 g (83.4 mmol) of sodium cyanide in 50 ml of dimethyl sulfoxide were stirred at 40° C. for 2 hours. Then, the reaction mixture was poured into a mixture of ice and water and was subsequently extracted with 3 portions of 75 ml of tert-butyl methyl ether. The combined organic phases were washed with water, then with brine and dried with anhydrous sodium sulfate. After evaporation of the solvent, 13.4 g (96% of theory) of [2-(4-isopropyl-phenyl)-thiazol-4-yl]-acetonitrile were obtained as brown solid.

MS: 243.2 $(M+H)^+$.

b] [2-(4-Isopropyl-phenyl)-thiazol-4-yl]-acetic acid

A mixture of 13 g (53.6 mmol) of 12-(4-isopropyl-phenyl)-thiazol-4-yl]-acetonitrile, 20 g of sodium hydroxide (500 mmol), 20 ml of water and 120 ml of propanol was stirred vigorously at 100° C. Hydrolysis was complete after 4 hours. The reaction mixture was then poured onto crushed ice and aqueous HCl, extracted three times with ethyl acetate, washed with water and brine, and dried with anhydrous sodium sulfate. Evaporation of the solvents left 13.8 g (98.5% of theory) of [2-(4-isopropyl-phenyl)-thiazol-4-yl]-acetic acid as light brown solid.

MS: 260.0 $(M-H)^-$.

c] [2-(4-Isopropyl-phenyl)-thiazol-4-yl]-acetic acid methyl ester

A solution of 6.9 g (26.4 mmol) of [2-(4-isopropyl-phenyl)-thiazol-4-yl]-acetic acid and 0.5 g of p-toluenesulfonic acid mono-hydrate (catalyst) in 70 ml of methanol and 5 ml of trimethyl orthoformate was heated at reflux for 5 hours. After neutralization with aqueous sodium bicarbonate solution, evaporation of the solvents, extraction of the residue with tert-butyl methyl ether, drying over anhydrous sodium sulfate and evaporation of the solvent, 6.4 g (88% of theory) of [2-(4-isopropyl-phenyl)-thiazol-4-yl]-acetic acid methyl ester were obtained as light brown oil.

MS: 275.1 $(M^+)$.

d] 2-[2-(4-Isopropyl-phenyl)-thiazol-4-yl]-ethanol

In analogy to the procedure described for example 12 b], 6.3 g (22.8 mmol) of [2-(4-isopropyl-phenyl)-thiazol-4-yl)-acetic acid methyl ester were reduced with lithium aluminium hydride to 2-[2-(4-isopropyl-phenyl)-thiazol-4-yl]-ethanol. 4.8 g of an orange, viscous oil were obtained (85% of theory).

MS: 248.1 $(M+H)^+$.

e] [rac]-2-Ethoxy-3-(4-{2-[2-(4-isopropyl-phenyl)-thiazol-4-]-ethoxy}-2-methyl-phenyl)-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(4-isopropyl-phenyl)-thiazol-4-yl]-ethanol in the presence of triphenylphosphine and diethyl azodicarboxylate to yield [rac]-2-ethoxy-3-(4-{2-[2-(4-isopropyl-phenyl)-thiazol-4-yl]-ethoxy}-2-methyl-phenyl)-propionic acid ethyl ester as colorless oil.

MS: 482.3 $(M+H)^+$, 436.2, 392.2, 364.2, 320.3, 256.2, 230.2.

f] [rac]-2-Ethoxy-3-(4-{2-[2-(4-isopropyl-phenyl)-thiazol-4-yl]-ethoxy}-2-methyl-phenyl -propionic acid In analogy to the procedure described in example 10 d], [rac]-2-ethoxy-3-(4-{2-[2-(4-isopropyl-phenyl)-thiazol-4-yl]-ethoxy}-2-methyl-phenyl)-propionic acid ethyl ester was treated with LiOH to obtain [rac]-2-ethoxy-3-(4-{2-[2-(4-isopropyl-phenyl)-thiazol-4-yl]-ethoxy}-2-methyl-phenyl)-propionic acid as colorless liquid.

MS: 454.3 $(M+H)^+$, 439.1, 371.3, 335.0, 258.3, 191.3.

Example 14 a] 4-Chloromethyl-2-(4-chloro-phenyl)-thiazole

In analogy to the procedure described in example 4 a], 4-chlorothiobenzamide was reacted with 1,3-dichloroacetone followed by treatment with concentrated sulfuric acid to obtain 4-chloromethyl-2-(4-chloro-phenyl)-thiazole as colorless crystals.

MS: 244.2 $(M+H)^+$, 187.2.

b] [rac]-3-{4-[2-(4-Chloro-phenyl)-thiazol-4-ylmethoxy]-2-methyl-phenyl}-2-ethoxy-propionic acid ethyl ester A mixture of [rac]-2-ethoxy-3-(4-hydroxy-2-methyl-phenyl)-propionic acid ethyl ester (37 mg, 0.15 mmol) (example 10 b]), 4-chloromethyl-2-(4-chloro-phenyl)-thiazole (44 mg, 0.18 mmol), cesium carbonate (59 mg, 0.18 mmol) and a trace of potassium iodide were suspended in acetone (3 ml). The suspension was heated under reflux for 5 h, the solvent evaporated under reduced pressure and the residue dissolved in 2 N HCl/ice water 1/1 and ethyl acetate. The layers were separated and the aqueous layer was extracted two times with ethyl acetate. The combined organic layers were washed two times with brine and dried over sodium sulfate. The solvent was removed under reduced pressure and the residue purified by column chromatography (silica gel, cyclohexane/AcOEt) to give 46 mg (0.1 mmol, 68%) of the title compound as colorless oil.

MS: 482.2 $(M+Na)^+$, 460.2 $(M+H)^+$, 432.3, 389.2, 317.2, 279.3, 211.3, 184.4.

c] [rac]-3-[4-2-(4-Chloro-phenyl)-thiazol-4-ylmethoxy]-2-methyl-phenyl}-2-ethoxy-propionic acid In analogy to the procedure described in example 10 d], [rac]-3-{4-[2-(4-chloro-phenyl)-thiazol-4-ylmethoxy]-2-methyl-phenyl}-2-ethoxy-propionic acid ethyl ester was treated with LiOH to obtain [rac]-3-{4-[2-(4-chlorophenyl)-thiazol-4-ylmethoxy]-2-methyl-phenyl}-2-ethoxy-propionic acid as light yellow liquid.

MS: 432.2 (M+H)+, 386.1, 249.2, 218.3, 176.2.

Example 15 a] rac]-3-{4-[2-(4-tert-Butyl-phenyl)-thiazol-4-ylmethoxy]-2-methyl-phenyl}-2-ethoxy-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 2-(4-tert-butyl-phenyl)-4-chloromethyl-thiazole (example 4 a]) in the presence of cesium carbonate and potassium iodide to yield [rac]-3-{4-[2-(4-tert-butyl-phenyl)-thiazol-4-ylmethoxy]-2-methyl-phenyl}-2-ethoxy-propionic acid ethyl ester as colorless liquid.

MS: 504.3 (M+Na)+, 482.3 (M+H)+, 438.3, 271.3, 230.2.

b] [rac]-3-{4-[2-(4-tert-Butyl-phenyl)-thiazol-4-ylmethoxy]-2-methyl-phenyl}-2-ethoxy-propionic acid In analogy to the procedure described in example 10 d], [rac]-3-{4-[2-(4-tert-butyl-phenyl)-thiazol-4-ylmethoxy]-2-methyl-phenyl}-2-ethoxy-propionic acid ethyl ester was treated with LiOH to obtain [rac]-3-{4-[2-(4-tert-butyl-phenyl)-thiazol-4-ylmethoxy]-2-methyl-phenyl}-2-ethoxy-propionic acid as colorless foam.

MS: 454.3 (M+H)+, 383.1, 320.3, 266.8, 252.3, 234.3, 166.3.

Example 16 a] [rac]-2-Ethoxy-3-{4-[2-(4-isopropyl-phenyl)-thiazol-4-ylmethoxy]-2-methyl-phenyl}-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 4-chloromethyl-2-(4-isopropyl-phenyl)-thiazole (prepared from 4-isopropyl-thiobenzamide and 1,3-dichloroacetone in analogy to the procedure described in example 4 a]) in the presence of cesium carbonate and potassium iodide to yield [rac]-2-ethoxy-3-{4-[2-(4-isopropyl-phenyl)-thiazol-4-ylmethoxy]-2-methyl-phenyl}-propionic acid ethyl ester as colorless liquid.

MS: 490.2 (M+Na)+, 468.2 (M+H)+, 424.4, 257.1, 216.3.

b] [rac]-2-Ethoxy-3-{4-[2-(4-isopropyl-phenyl)-thiazol-4-ylmethoxy]-2-methyl-phenyl}-propionic acid In analogy to the procedure described in example 10 d], [rac]-2-ethoxy-3-{4-[2-(4-isopropyl-phenyl)-thiazol-4-ylmethoxy]-2-methyl-phenyl}-propionic acid ethyl ester was treated with LiOH to obtain [rac]-2-ethoxy-3-{4-[2-(4-isopropyl-phenyl)-thiazol-4-ylmethoxy]-2-methyl-phenyl}-propionic acid as colorless oil.

MS: 438.2 (M−H)−, 392.1, 348.3, 255.2.

Example 17 a] (S)-4-Benzyl-3-[(2S,3R)-3-(4-benzyloxy-2-methyl-phenyl)-2-ethoxy-3-hydroxy-propionyl]-oxazolidin-2-one (S)-4-Benzyl-3-ethoxyacetyl-oxazolidin-2-one (12.45 g, 47 mmol) (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, Tetrahedron: Asymmetry 1999, 10, 1353–1367) was dissolved in dry dichloromethane (270 ml) under an argon atmosphere and the solution was cooled to −78° C. Triethylamine (7.98 ml, 57 mmol) was added, followed by the slow addition, over approximately 20 min, of di-n-butylboron triflate (1 M solution in dichloromethane, 25 ml, 50 mmol) such that the reaction temperature was kept below −70° C. The mixture was stirred at −78° C. for 50 min, the cooling bath was replaced with an ice bath and the mixture stirred at 0° C. for additional 50 min before being recooled to −78° C. A solution of 4-benzyloxy-2-methyl-benzaldehyde (10.7 g, 47 mmol) in dry dichloromethane (130 ml) was added over ca. 45 min, such that the reaction temperature was maintained below −70° C. The resulting mixture was stirred at −78° C. for 45 min, warmed from −78° C. to 0° C. and stirred at 0° C. for a further 1.5 h. The reaction mixture was poured onto ice water/brine and extracted two times with dichloromethane. The combined extracts were washed with brine and dried over sodium sulfate. The solvent was removed under reduced pressure and the residue purified by column chromatography (silica gel, cyclohexane/AcOEt) to give 22.3 g (45.6 mmol, 96%) of the title compound as colorless oil. According to $^1$H-NMR spectroscopy, one of the four isomers is strongly predominating. The configuration was tentatively assigned as 2S,3R according to D. Haigh et al., Tetrahedron: Asymmetry 1999, 10, 1353–1367.

MS: 512.3 (M+Na)+, 472.3, 447.2, 387.2, 327.2, 295.3, 267.3, 232.1, 175.1.

b] (2S,3R)-3-(4-Benzyloxy-2-methyl-phenyl)-2-ethoxy-3-hydroxy-propionic acid methyl ester A 5.4 M solution of sodium methoxide (7.3 ml, 39.5 mmol) was added to an ice-cooled and stirred suspension of (S)-4-benzyl-3-[(2S,3R)-3-(4-benzyloxy-2-methyl-phenyl)-2-ethoxy-3-hydroxy-propionyl]-oxazolidin-2-one (17.6 g, 36 mmol) in dry methanol (87 ml). The mixture was stirred at 0° C. for 15 min, quenched and neutralized by the addition of dilute aqueous hydrochloric acid (1.0 M). The solution was concentrated under reduced pressure and the residue dissolved in ice water/ethyl acetate 1/1. The layers were separated and the aqueous layer was extracted two times with ethyl acetate. The combined organic layers were washed with ice water and dried over sodium sulfate. The solvent was removed under reduced pressure and the residue purified by column chromatography (silica gel, cyclohexane/AcOEt) to give 8.6 g (25 mmol, 69%) of the title compound as light yellow oil. According to $^1$H-NMR spectroscopy, one single diastereomer was obtained.

MS: 367.2 (M+Na)+, 362.2 (M+NH$_4$)+, 327.3, 299.3, 239.3, 211.2.

c] (2S)-3-(4-Benzyloxy-2-methyl-phenyl)-2-ethoxy-propionic acid methyl ester

Triethylsilane (23 ml, 145 mmol) was added to a vigorously stirred, ice-cooled solution of (2S,3R)-3-(4-benzyloxy-2-methyl-phenyl)-2-ethoxy-3-hydroxy-propionic acid methyl ester (5 g, 14.5 mmol) in trifluoroacetic acid (84 ml) under an argon atmosphere. The mixture was stirred at 0° C. for 30 min and for additional 2 h at ambient temperature. The solution was poured onto crashed ice and extracted with ethyl acetate. The organic layer was washed two times with water and neutralized with saturated aqueous sodium bicarbonate solution. The ethyl acetate layer was washed with brine and dried over sodium sulfate. The solvent was removed under reduced pressure to give a colorless oil which was purified by column chromatography (silica gel, cyclohexane/AcOEt) to yield 2.15 g (6.5 mmol, 45%) of the title compound as colorless oil.

MS: 351.2 (M+Na)+, 346.3 (M+NH$_4$)+, 283.2, 276.2, 223.2, 195.5.

d] (2S)-2-Ethoxy-3-(4-hydroxy-2-methyl-phenyl)-propionic acid methyl ester

A solution of (2S)-3-(4-benzyloxy-2-methyl-phenyl)-2-ethoxy-propionic acid methyl ester (3.6 g, 11 mmol) in methanol (300 ml) was hydrogenated over 10% palladium on charcoal (1 g) at ambient temperature for 2 h. The catalyst was filtered off and the solvent evaporated under reduced pressure to give 2 g (8.4 mmol, 77%) of the title compound as yellow liquid which was used in the next step without further purification.

MS: 261.2 (M+Na)+, 256.1 (M+NH$_4$)+, 239.3 (M+H)+, 193.2, 151.1.

e] (2S)-3-{4-[2-(3-Chloro-4-fluoro-phenyl)-thiazol-4-ylmethoxy]-2-methyl-phenyl}-2-ethoxy-propionic acid methyl ester In analogy to the procedure described in example 14 b], (2S)-2-ethoxy-3-(4-hydroxy-2-methyl-phenyl)-propionic acid methyl ester was reacted with 2-(3-chloro-4-fluoro-phenyl)-4-chloromethyl-thiazole (prepared from 3-chloro-4-fluoro-thiobenzamide and 1,3-dichloroacetone in analogy to the procedure described in example 4 a]) in the presence of cesium carbonate and potassium iodide to yield (2S)-3-{4-[2-(3-chloro-4-fluoro-phenyl)-thiazol-4-ylmethoxy]-2-methyl-phenyl}-2-ethoxy-propionic acid methyl ester as yellow liquid.

f] (2S)-3-{4-[2-(3-Chloro-4-fluoro-phenyl)-thiazol-4-ylmethoxy]-2-methyl-phenyl}-2-ethoxy-propionic acid In analogy to the procedure described in example 10 d], (2S)-3-{4-[2-(3-chloro-4-fluoro-phenyl)-thiazol-4-ylmethoxy]-2-methyl-phenyl}-2-ethoxy-propionic acid methyl ester was treated with LiOH to obtain (2S)-3-{4-[2-(3-chloro-4-fluoro-phenyl)-thiazol-4-ylmethoxy]-2-methyl-phenyl}-2-ethoxy-propionic acid as colorless solid.

MS: 448.1 (M–H)–, 402.1, 357.9, 308.8, 283.5, 254.8, 222.8.

Example 18 a] (2S)-2-Ethoxy-3-{2-methyl-4-[2-(4-trifluoromethyl-phenyl)-thiazol-4-ylmethoxy]-phenyl}-propionic acid methyl ester In analogy to the procedure described in example 14 b], (2S)-2-ethoxy-3-(4-hydroxy-2-methyl-phenyl)-propionic acid methyl ester (example 17 d]) was reacted with 4-chloromethyl-2-(4-trifluoromethyl-phenyl)-thiazole (prepared from 4-trifluoromethyl-thiobenzamide and 1,3-dichloroacetone in analogy to the procedure described in example 4 a]) in the presence of cesium carbonate and potassium iodide to yield (2S)-2-ethoxy-3-{2-methyl-4-[2-(4-trifluoromethyl-phenyl)-thiazol-4-ylmethoxy]-phenyl}-propionic acid methyl ester as colorless liquid.

MS: 502.2 (M+Na)+, 480.3 (M+H)+, 434.2, 420.2, 392.0, 283.1, 242.1, 181.2.

b] (2S)-2-Ethoxy-3-{2-methyl-4-[2-(4-trifluoromethyl-phenyl)-thiazol-4-ylmethoxy]-phenyl}-propionic acid In analogy to the procedure described in example 10 d], (2S)-2-ethoxy-3-{2-methyl-4-[2-(4-trifluoromethyl-phenyl)-thiazol-4-ylmethoxy]-phenyl}-propionic acid methyl ester was treated with LiOH to obtain (2S)-2-ethoxy-3-{2-methyl-4-[2-(4-trifluoromethyl-phenyl)-thiazol-4-ylmethoxy]-phenyl}-propionic acid as colorless solid.

MS: 488.2 (M+Na)+, 466.1 (M+H)+, 420.1, 371.3, 307.2, 269.2, 217.2, 187.2.

Example 19 a] (S)-4-Benzyl-3-[(2S)-3-(4-benzyloxy-2-methyl-phenyl)-2-ethoxy-propionyl]-oxazolidin-2-one In analogy to the procedure described in example 17 c], (S)-4-benzyl-3-[(2S,3R)-3-(4-benzyloxy-2-methyl-phenyl)-2-ethoxy-3-hydroxy-propionyl]-oxazolidin-2-one (example 17 a]) was treated with triethylsilane in trifluoroacetic acid to yield the title compound as colorless liquid.

MS: 496.2 (M+Na)+, 491.3 (M+NH$_4$)+, 474.2 (M+H)+, 428.3, 352.3, 251.2, 175.2.

b] (S)-4-Benzyl-3-[(2S)-2-ethoxy-3-(4-hydroxy-2-methyl-phenyl)-propionyl]-oxazolidin-2-one In analogy to the procedure described in example 17 d], (S)-4-benzyl-3-[(2S)-3-(4-benzyloxy-2-methyl-phenyl)-2-ethoxy-propionyl]-oxazolidin-2-one was hydrogenated over 10% palladium on charcoal to give the title compound as yellow liquid.

MS: 382.1 (M–H)–, 324.9, 305.1, 282.9, 261.8, 255.2, 221.4, 175.6.

c] (S)-4-Benzyl-3-[(2S)-3-{4-[2-(3-chloro-phenyl)-thiazol-4-ylmethoxy]-2-methyl-phenyl}-2-ethoxy-propionyl}-oxazolidin-2-one In analogy to the procedure described in example 10 c], (S)-4-benzyl-3-[(2S)-2-ethoxy-3-(4-hydroxy-2-methyl-phenyl)-propionyl]-oxazolidin-2-one was reacted with [2-(3-chloro-phenyl)-thiazol-4-yl]-methanol (for the preparation of [2-(3-chloro-phenyl)-thiazol-4-yl]-methanol see: C. Lambert, R. Pepis, International Patent Appl., Publication No. WO 8900568 (A1), 1989) in the presence of triphenylphosphine and diethyl azodicarboxylate to yield (S)-4-benzyl-3-[(2S)-3-{4-[2-(3-chloro-phenyl)-thiazol-4-ylmethoxy]-2-methyl-phenyl}-2-ethoxy-propionyl}-oxazolidin-2-one as colorless solid.

MS: 613.3 (M+Na)+, 591.2 (M+H)+, 561.4, 487.2, 465.2, 419.2, 368.1, 299.3, 211.3, 167.2.

d] (2S)-3-{4-[2-(3-Chloro-phenyl)-thiazol-4-ylmethoxy]-2-methyl-phenyl}-2-ethoxy-propionic acid (S)-4-Benzyl-3-[(2S)-3-{4-[2-(3-chloro-phenyl)-thiazol-4-ylmethoxy]-2-methyl-phenyl}-2-ethoxy-propionyl}-oxazolidin-2-one (80 mg, 140 μmol) was dissolved in ice-cooled THF (0.8 ml) and treated with 1 N NaOH (0.34 ml, 350 μmol) at 0° C. for 2 h. The reaction mixture was poured onto ice water/HCl and extracted two times with diethyl ether. The combined organic layers were washed with water and brine and dried over sodium sulfate. Evaporation of the solvent gave 52 mg (120 μmol, 89%) of the title compound as colorless solid.

MS: 454.2 (M+Na)+, 432.1 (M+H)+, 345.1, 269.2, 241.2, 187.2.

Example 20 a] (2S)-3-{4-[2-(4-Chloro-phenyl)-thiazol-4-ylmethoxy]-2-methyl-phenyl}-2-ethoxy-propionic acid methyl ester In analogy to the procedure described in example 14 b], (2S)-2-ethoxy-3-(4-hydroxy-2-methyl-phenyl)-propionic acid methyl ester (example 17 d]) was reacted with 4-chloromethyl-2-(4-chloro-phenyl)-thiazole (example 14 a]) in the presence of cesium carbonate and potassium iodide to yield (2S)-3-{4-[2-(4-chloro-phenyl)-thiazol-4-ylmethoxy]-2-methyl-phenyl}-2-ethoxy-propionic acid methyl ester as light yellow liquid.

MS: 446.1 (M+H)+, 342.2, 279.1, 242.2, 219.3.

b] (2S)-3-{4-[2-(4-Chloro-phenyl)-thiazol-4-ylmethoxy]-2-methyl-phenyl}-2-ethoxy-propionic acid In analogy to the procedure described in example 10 d], (2S)-3-{4-[2-(4-chloro-phenyl)-thiazol-4-ylmethoxy]-2-methyl-phenyl}-2-ethoxy-propionic acid methyl ester was treated with LiOH to obtain (2S)-3-{4-[2-(4-chloro-phenyl)-thiazol-4-ylmethoxy]-2-methyl-phenyl}-2-ethoxy-propionic acid as colorless solid, which was crystalized from hexane/AcOEt to afford colorless crystals. According to chiral HPLC of the corresponding methyl ester (Chiralcel-OJ), the enantiomeric excess amounts to 98.9%.

MS: 430.2 (M–H)–, 384.1, 293.1, 255.2.

Example 20A a] 3-(4-Benzyloxy-2-methyl-phenyl)-2-ethoxy-3-hydroxy-propionic acid ethyl ester (mixture of stereoisomers)

To a –78° C. cold 2 M solution of lithium diisopropylamide (305 mmol) in THF/n-heptane (152.4 ml) was added a solution of ethoxy-acetic acid ethyl ester (45.2 ml, 331 mmol) in tetrahydrofuran (240 ml) within 1.5 h under an argon atmosphere. The mixture was stirred for 30 min. A solution of 4-benzyloxy-2-methyl-benzaldehyde (30 g, 132.6 mmol) in tetrahydrofuran (420 ml) was added dropwise over a period of 50 min. The reaction mixture was stirred 2 h at −78° C., poured onto ice water/aqueous ammonium chloride solution 1/1 and extracted two times with ethyl acetate. The combined extracts were washed three times with ice water/brine 1/1 and dried over sodium sulfate. The solvent was removed under reduced pressure and the residue purified by column chromatography (silica gel, n-heptane/AcOEt) to give 48.8 g (136.2 mmol) of the title compound as a mixture of stereoisomers as yellow oil.

MS: 376.4 (M+NH$_4$)$^+$, 341.4, 186.5.

b] (Z)-3-(4-Benzyloxy-2-methyl-phenyl)-2-ethoxy-acrylic acid ethyl ester

To a solution of 3-(4-benzyloxy-2-methyl-phenyl)-2-ethoxy-3-hydroxy-propionic acid ethyl ester (mixture of stereoisomers; 48.8 g, 136.2 mmol) in N,N-dimethylformarrd (500 ml) was added sulfuric acid (19.6 ml, 96%). The reaction mixture was heated to 100° C. for 2.5 h, cooled to ambient temperature, poured onto ice water/saturated aqueous NaHCO$_3$ solution 1/1 and extracted two times with ethyl acetate. The combined extracts were washed with ice water/brine 1/1 and dried over sodium sulfate. The solvent was removed under reduced pressure to give 46.1 g (135.4 mmol) of crude (Z)-3-(4-benzyloxy-2-methyl-phenyl)-2-ethoxy-acrylic acid ethyl ester which was used in the next step without further purification.

MS: 358.3 (M+NH$_4$)$^+$, 341.4 (M+H)$^+$, 292.4, 222.4, 187.4.

c] (Z)-2-Ethoxy-3-(4-hydroxy-2-methyl-phenyl)-acrylic acid ethyl ester

To a solution of (Z)-3-(4-benzyloxy-2-methyl-phenyl)-2-ethoxy-acrylic acid ethyl ester (46.1 g, 135.4 mmol) in dichloromethane (500 ml) was added BF3.OEt$_2$ (186 ml, 677 mmol, 46%) and dimethyl sulfide (149 ml, 2.03 mol). The reaction mixture was stirred at ambient temperature for 14 h, poured onto ice water and extracted two times with dichloromethane. The combined extracts were washed with ice water/brine 1/1 and dried over sodium sulfate. The solvent was removed under reduced pressure and the residue purified by column chromatography (silica gel, n-heptane/AcOEt) to give 23.1 g (92.3 mmol, 68% over three steps) of the tide compound as yellow crystals.

MS: 248.9 (M+H)$^+$, 219.9.

d] (Z)-2-Ethoxy-3-{4-[2-(4-chloro-phenyl)-thiazol-4-ylmethoxy]-2-methyl-phenyl}-acrylic acid ethyl ester In analogy to the procedure described in example 14 b], (Z)-2-ethoxy-3-(4-hydroxy-2-methyl-phenyl)-acrylic acid ethyl ester was reacted with 4-chloromethyl-2-(4-chloro-phenyl)-thiazole (example 14 a]) in the presence of cesium carbonate and potassium iodide to yield (Z)-2-ethoxy-3-{4-[2-(4-chloro-phenyl)-thiazol-4-ylmethoxy]-2-methyl-phenyl}-acrylic acid ethyl ester as colorless crystals.

MS: 458.4 (M+H)$^+$, 293.6, 252.3.

e] (Z)-2-Ethoxy-3-{4-[2-(4-chloro-phenyl)-thiazol-4-ylmethoxy]-2-methyl-phenyl}-acrylic acid To a solution of (Z)-2-ethoxy-3-{4-[2-(4-chloro-phenyl)-thiazol-4-ylmethoxy]-2-methyl-phenyl)-acrylic acid ethyl ester (15.8 g, 34.5 mmol) in THF/methanol 2/1 (235 ml) was added a 3 M aqueous NaOH solution (57.5 ml, 172.5 mmol). The reaction mixture was stirred for 2.5 h at ambient temperature, concentrated under reduced pressure, diluted with ice water and acidified with 1 M aqueous HCl solution. Twofold extraction with ethyl acetate was followed by washing of the combined extracts with ice water/brine 1/1 (three times) and drying of the organic layer over sodium sulfate. The solvent was removed under reduced pressure and the crude product crystallized from dichloro-methane/methanol/n-heptane to give the title compound (13.8 g, 32.1 mmol, 93%) as colorless crystals.

MS: 428.2 (M−H)$^-$, 255.3.

f] (S)-3-{4-[2-(4-Chloro-phenyl)-thiazol-4-ylmethoxy]-2-methyl-phenyl}-2-ethoxy-propionic acid In a glove box (O$_2$ content ≧2 ppm ), a 35 ml stainless steel autoclave was charged with 0.43 g of (Z)-3-{4-[2-(4-chloro-phenyl)-thiazol-4-ylmethoxy]-2-methyl-phenyl}-2-ethoxy-acrylic acid (0.99 mmol), 2.6 ml of dichloromethane, 2.6 ml of methanol, 0.09 ml of a 30% aqueous NaOH solution (0.49 mmol) and 40.0 mg (0.049 mmol ) of [Ru(OAc)$_2$((+)-TMBTP)]. TMBTP is 4,4'-bis (diphenylphosphino)-2,2',5,5'-tetramethyl-3,3'-dithiophene, its synthesis as (R) or (S) enantiomer is described in WO 96/01831 appl to Italfarmaco Sud and in T. Benincori et al, *J. Org. Chem.* 2000, 65, 2043. The complex [Ru(OAc)$_2$((+)-TMBTP)] has been synthesized in analogy to a general procedure reported in N. Feiken et al, *Organometallics* 1997, 16, 537, $^{31}$P-NMR (CDCl$_3$): 61.4 ppm (s). The autoclave was sealed and the hydrogenation was run under stirring at 60° C. under 60 bar of hydrogen. After 16 h the autoclave was opened and the yellow-brown solution was rotary evaporated to dryness (50° C./5 mbar). The residue was dissolved in 15 ml of ethyl acetate, 15 ml of water and 0.5 ml of aqueous hydrochloric acid (25%). The organic layer was separated and evaporated to dryness (50° C./5 mbar) to afford 0.45 g of crude product as a solid with an enantiomeric purity of 91% and a chemical purity of >99% according to HPLC. The black crude product was dissolved in hot ethyl acetate, charcoal (200 mg) was added and the mixture was heated under reflux conditions for 10 min. The charcoal was filtered off and the filtrate evaporated to dryness under reduced pressure. The residue was purified by column chromatography (silica gel, n-heptanelethyl acetate, two times) to give brown crystals which were recrystallized from ethyl acetate to afford the tide compound (248 mg, 573 mmol, 55%) as off-white crystals. According to chiral HPLC (Chiralcel-OJ column, 25 cm×4.5 mm, 80% heptane/20% ethanol with 1.5% trifluoroacetic acid, flow at 1 ml/min, 25° C., 298 nm. Retention times: R-acid 16.3 min, S-acid 18.9 min, α,β-unsaturated Z-acid 26.3 min), the enantiomeric excess amounts to 99.6%.

MS: 430.2 (M−H)$^-$, 384.1, 293.1.

Example 21 a] (S)-4-Benzyl-3-[(2S,3R)-3-(4-benzyloxy-2-methoxy-phenyl)-2-ethoxy-3-hydroxy-propionyl]-oxazolidin-2-one In analogy to the procedure described in example 17 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353–1367) was reacted with 4-benzyloxy-2-methoxy-benzaldehyde in the presence of triethylamine and di-n-butylboron triflate to give (S)-4-benzyl-3-[(2S,3R)-3-(4-benzyloxy-2-methoxy-phenyl)-2-ethoxy-3-hydroxy-propionyl]-oxazolidin-2-one as light yellow solid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 528.3 (M+Na)$^+$, 523.3 (M+NH$_4$)$^+$, 488.3, 442.4, 311.2, 239.3.

b] (2S,3R)-3-(4-Benzyloxy-2-methoxy-phenyl)-2-ethoxy-3-hydroxy-propionic acid methyl ester In analogy to the procedure described in example 17 b], (S)-4-benzyl-3-[(2S,3R)-3-(4-benzyloxy-2-methoxy-phenyl)-2-ethoxy-3-hydroxy-propionyl]-oxazolidin-2-one was treated with sodium methoxide in methanol to give (2S,3R)-3-(4-benzyloxy-2-methoxy-phenyl)-2-ethoxy-3-hydroxy-propionic acid methyl ester as colorless liquid. According to $^1$H-NMR spectroscopy, one single diastereomer was obtained.

MS: 383.2 (M+Na)$^+$, 378.2 (M+NH$_4$)$^+$, 343.2, 311.2, 283.2, 239.3, 163.2.

c] (2S)-2-Ethoxy-3-(4-hydroxy-2-methoxy-phenyl)-propionic acid methyl ester

A solution of (2S,3R)-3-(4-benzyloxy-2-methoxy-phenyl)-2-ethoxy-3-hydroxy-propionic acid methyl ester (100 mg, 200 μmol) and oxalic acid dihydrate (150 mg, 1.2 mmol) in isopropanol (2 ml) was hydrogenated at a pressure of 50 atmospheres over 10% palladium on charcoal (20 mg) at ambient temperature for 6.5 h. The catalyst was filtered off and the solvent evaporated under reduced pressure. The residue was dissolved in ice water/aqueous sodium bicarbonate solution 1/1 and extracted two times with ethyl acetate. The combined extracts were washed two times with ice water/brine 1/1 and dried over sodium sulfate. The solvent was removed under reduced pressure to give a yellow liquid which was purified by column chromatography (silica gel, cyclohexane/AcOEt) to yield 43 mg (170 μmol, 85%) of the title compound as light yellow liquid.

MS: 277.1 (M+Na)$^+$, 209.2, 195.3, 181.2, 177.2, 167.2.

d] (2S )-3-{4-[2-(4-Chloro-phenyl)-thiazol-4-ylmethoxy]-2-methoxy-phenyl}-2-ethoxy-propionic acid methyl ester In analogy to the procedure described in example 14 b], (2S)-2-ethoxy-3-(4-hydroxy-2-methoxy-phenyl)-propionic acid methyl ester was reacted with 4-chloromethyl-2-(4-chloro-phenyl)-thiazole (example 14 a]) in the presence of cesium carbonate and potassium iodide to yield (2S)-3-{4-[2-(4-chloro-phenyl)-thiazol-4-ylmethoxy]-2-methoxy-phenyl}-2-ethoxy-propionic acid methyl ester as light yellow liquid.

MS: 462.1 (M+H)$^+$, 416.1, 305.4, 251.2, 174.3.

e] (2S)-3-{4-[2-(4-Chloro-phenyl)-thiazol-4-ylmethoxy]-2-methoxy-phenyl}-2-ethoxy-propionic acid In analogy to the procedure described in example 10 d], (2S)-3-{4-[2-(4-chloro-phenyl)-thiazol-4-ylmethoxy]-2-methoxy-phenyl}-2-ethoxy-propionic acid methyl ester was treated with LiOH to obtain (2S)-3-{4-[2-(4-chloro-phenyl)-thiazol-4-ylmethoxy]-2-methoxy-phenyl}-2-ethoxy-propionic acid as colorless solid.

MS: 446.1 (M−H)$^−$, 400.1, 356.0, 329.8, 281.0, 255.5, 227.0, 192.1.

Example 22 a] (S)-4-Benzyl-3-[(2S,3R)-3-(4-benzyloxy-2-chloro-phenyl)-2-ethoxy-3-hydroxy-propionyl]-oxazolidin-2-one In analogy to the procedure described in example 17 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353–1367) was reacted with 4-benzyloxy-2-chloro-benzaldehyde (for the preparation of 4-benzyloxy-2-chloro-benzaldehyde see: T. Kimachi, M. Kawase, S. Matsuki, K. Tanaka, F. Yoneda, *J. Chem. Soc., Perkin Trans.* 1 1990, 253–256) in the presence of triethylamine and di-n-butylboron triflate to give (S)-4-benzyl-3-[(2S,3R)-3-(4-benzyloxy-2-chloro-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 532.3 (M+Na)$^+$, 527.2 (M+NH$_4$)$^+$, 446.1, 381.2, 315.1, 287.2, 243.2, 178.2.

b] (2S,3R)-3-(4-Benzyloxy-2-chloro-phenyl)-2-ethoxy-3-hydroxy-propionic acid methyl ester In analogy to the procedure described in example 17 b], (S)-4-benzyl-3-1(2S,3R)-3-(4-benzyloxy-2-chloro-phenyl)-2-ethoxy-3-hydroxy-propionyl]-oxazolidin-2-one was treated with sodium methoxide in methanol to give (2S,3R)-3-(4-benzyloxy-2-chloro-phenyl)-2-ethoxy-3-hydroxy-propionic acid methyl ester as colorless liquid. According to $^1$H-NMR spectroscopy, one single diastereomer was obtained.

MS: 387.1 (M+Na)$^+$, 382.2 (M+NH$_4$)$^+$, 328.2, 319.2, 279.2, 203.2.

c] (2S)-3-(4-Benzyloxy-2-chloro-phenyl)-2-ethoxy-propionic acid methyl ester

In analogy to the procedure described in example 17 c], (2S,3R)-3-(4-benzyloxy-2-chloro-phenyl)-2-ethoxy-3-hydroxy-propionic acid methyl ester was treated with tri-ethylsilane in trifluoroacetic acid to yield (2S)-3-(4-benzyloxy-2-chloro-phenyl)-2-ethoxy-propionic acid methyl ester as colorless liquid.

MS: 371.4 (M+Na)$^+$, 366.2 (M+NH$_4$)$^+$, 303.2, 269.2, 222.2, 187.2.

d] (2S)-3-(2-Chloro-4-hydroxy-phenyl)-2-ethoxy-propionic acid methyl ester

Dimethyl sulfide (5.8 ml, 79 mmol) and boron trifluoride diethyl etherate (46% purity, 4.3 ml, 16 mmol) were added to a ice cold solution of (2S)-3-(4-benzyloxy-2-chloro-phenyl)-2-ethoxy-propionic acid methyl ester (1.1 g, 3.2 mmol) in dichloromethane (34 ml) under an argon atmosphere. The mixture was stirred for 5 h at ambient temperature, poured into ice water/brine 1/1 and extracted two times with dichloromethane. The combined extracts were washed with ice water/brine 1/1 and dried over sodium sulfate. Removal of the solvent under reduced pressure gave a colorless oil which was purified by column chromatography (silica gel, cyclohexane/AcOEt) to yield 0.6 g (2.3 mmol, 74%) of the title compound as colorless oil.

MS: 281.0 (M+Na)$^+$, 276.1 (M+NH$_4$)$^+$, 251.3, 213.3, 187.2.

e] (2S)-3-{2-Chloro-4-[2-(4-chloro-phenyl)-thiazol-4-ylmethoxy]-phenyl}-2-ethoxy-propionic acid methyl ester In analogy to the procedure described in example 14 b], (2S)-3-(2-chloro-4-hydroxy-phenyl)-2-ethoxy-propionic acid methyl ester was reacted with 4-chloromethyl-2-(4-chloro-phenyl)-thiazole (example 14 a]) in the presence of cesium carbonate and potassium iodide to yield (2S)-3-{2-chloro-4-[2-(4-chloro-phenyl)-thiazol-4-ylmethoxy]-phenyl}-2-ethoxy-propionic acid methyl ester as light yellow solid.

MS: 466.1 (M+H)$^+$, 407.2, 371.4, 344.1, 300.2, 269.2, 187.2.

f] (2S)-3-{2-Chloro-4-[2-(4-chloro-phenyl)-thiazol-4-ylmethoxy]-phenyl}-2-ethoxy-propionic acid In analogy to the procedure described in example 10 d], (2S)-3-{2-chloro-4-[2-(4-chloro-phenyl)-thiazol-4-ylmethoxy]-phenyl}-2-ethoxy-propionic acid methyl ester was treated with LiOH to obtain (2S)-3-{2-chloro-4-[2-(4-chloro-phenyl)-thiazol-4-ylmethoxy]-phenyl}-2-ethoxy-propionic acid as colorless solid.

MS: 452.1 (M+H)$^+$, 420.9, 399.4, 371.4, 299.7, 265.3, 237.0, 190.2.

Example 23 a] 1-Ethyl-3-(phenylmethoxy)-benzene

To a suspension of potassium carbonate (17 g, 123 mmol) in N,N-dimethylformamide (40 ml) was added a solution of 3-ethyl-phenol (14.8 ml, 123 mmol) in N,N-dimethylformamide (40 ml) at 2° C. under an argon atmosphere. After stirring for 50 min at 2° C., benzyl bromide (14.6 ml, 123 mmol) was added over a period of 15 min at 2° C. The suspension was stirred for additional 30 min at 2° C. and for 12 h at ambient temperature. After adding ice water (250 ml), the solution was extracted two times with diethyl ether. The combined extracts were washed two times with brine and dried over sodium sulfate. Evaporation of the solvent gave a yellow oil which was purified by column chromatography (silica gel, cyclohexane) to yield 24.3 g (114 mmol, 93%) of the title compound as yellow liquid.

MS: 212.2 (M+H)$^+$, 183.1, 91.2, 65.1.

b] 1-Bromo-2-ethyl-4-(phenylmethoxy)-benzene

To a solution of 1-ethyl-3-(phenylmethoxy)-benzene (15 g, 71 mmol) in THF (200 ml) were added N-bromosuccinimide (16.3 g, 92 mmol) and concentrated sulfuric acid (2.4 ml). The solution was stirred for 5 h at ambient temperature. Sodium bicarbonate (3.6 g) and 10% aqueous NaHSO$_3$ solution (400 ml) were added under ice cooling. The resulting mixture was stirred for 10 min and then poured into ethyl acetate. The phases were separated and the aqueous phase was extracted with ethyl acetate. The combined extracts were washed with ice water and brine and dried over sodium sulfate. Removal of the solvent under reduced pressure gave a yellow oil which was purified by column chromatography (silica gel, cyclohexane) to yield 17.1 g (58.7 mmol, 83%) of the title compound as colorless liquid.

MS: 292.0 (M)$^+$, 290.0 (M)$^+$, 212.2, 91.1, 65.2.

c] 4-Benzyloxy-2-ethyl-benzaldehyde

A 1.6 M solution of n-BuLi in hexane (44.4 ml, 69.9 mmol) was added within 10 min to a stirred cooled (−85° C.) solution of 1-bromo-2-ethyl-4-(phenylmethoxy)-benzene (18.5 g, 63.5 mmol) in dry THF (22 ml). The mixture was stirred for 1 h at −5° C. under an argon atmosphere. N,N-Dimethylformamide (25.5 ml, 330.4 mmol) was added and the temperature was allowed to rise slowly to room temperature. An aqueous saturated NH$_4$Cl solution (70 ml) was added under ice cooling. The mixture was extracted two times with dichloromethane, the combined extracts were washed with brine and dried over sodium sulfate. Removal of the solvent under reduced pressure gave a yellow oil which was purified by column chromatography (silica gel, cyclohexane/AcOEt) to yield 11.9 g (49.5 mmol, 78%) of the title compound as yellow oil.

MS: 240.1 (M+H)$^+$, 91.1, 77.1, 65.2.

d] (S)-4-Benzyl-3-[(2S,3R)-3-(4-benzyloxy-2-ethyl-phenyl)-2-ethoxy-3-hydroxy-propionyl]-oxazolidin-2-one

In analogy to the procedure described in example 17 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R M. Hindley, A. Ramaswamy, N. C. Stevens, *Tetrahedron: Asymmetry* 1999, 10, 1353–1367) was reacted with 4-benzyloxy-2-ethyl-benzaldehyde in the presence of triethylamine and di-n-butylboron triflate to give (S)-4-benzyl-3-[(2S,3R)-3-(4-benzyloxy-2-ethyl-phenyl)-2-ethoxy-3-hydroxy-propionyl]-oxazolidin-2-one as yellow foam. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 526.3 (M+Na)$^+$, 521.3 (M+NH$_4$)$^+$, 486.2, 381.2, 309.2, 281.2, 253.3, 178.1.

e] (2S,3R)-3-(4-Benzyloxy-2-ethyl-phenyl)-2-ethoxy-3-hydroxy-propionic acid methyl ester

In analogy to the procedure described in example 17 b], (S)-4-benzyl-3-1(2S,3R)-3-(4-benzyloxy-2-ethyl-phenyl)-2-ethoxy-3-hydroxy-propionyl]-oxazolidin-2-one was treated with sodium methoxide in methanol to give (2S,3R)-3-(4-benzyloxy-2-ethyl-phenyl)-2-ethoxy-3-hydroxy-propionic acid methyl ester as colorless liquid. According to $^1$H-NMR spectroscopy, one single diastereomer was obtained.

MS: 381.2 (M+Na)$^+$, 376.3 (M+NH$_4$)$^+$, 341.3, 295.3, 253.2, 225.3.

f] (2S)-3-(4-Benzyloxy-2-ethyl-phenyl)-2-ethoxy-propionic acid methyl ester

In analogy to the procedure described in example 17 c], (2S,3R)-3-(4-benzyloxy-2-ethyl-phenyl)-2-ethoxy-3-hydroxy-propionic acid methyl ester was treated with triethylsilane in trifluoroacetic acid to yield (2S)-3-(4-benzyloxy-2-ethyl-phenyl)-2-ethoxy-propionic acid methyl ester as colorless liquid.

MS: 365.2 (M+Na)$^+$, 360.2 (M+NH$_4$)$^+$, 297.3, 283.2, 237.2, 209.3, 181.2.

g] (2S)-2-Ethoxy-3-(2-ethyl-4-hydroxy-phenyl)-propionic acid methyl ester

In analogy to the procedure described in example 17 d], (2S)-3-(4-benzyloxy-2-ethyl-phenyl)-2-ethoxy-propionic acid methyl ester was hydrogenated over 10% palladium on charcoal to give (2S)-2-ethoxy-3-(2-ethyl-4-hydroxy-phenyl)-propionic acid methyl ester as colorless liquid.

MS: 275.2 (M+Na)$^+$, 270.3 (M+NH$_4$)$^+$, 253.3 (M+H)$^+$, 207.2, 175.2, 165.3, 147.2.

h] (2S)-3-{4-[2-(4-Chloro-phenyl)-thiazol-4-ylmethoxy]-2-ethyl-phenyl}-2-ethoxy-propionic acid methyl ester

In analogy to the procedure described in example 14 b], (2S)-2-ethoxy-3-(2-ethyl-4-hydroxy-phenyl)-propionic acid methyl ester was reacted with 4-chloromethyl-2-(4-chloro-phenyl)-thiazole (example 14 a]) in the presence of cesium carbonate and potassium iodide to yield (2S)-3-{4-[2-(4-chloro-phenyl)-thiazol-4-ylmethoxy]-2-ethyl-phenyl}-2-ethoxy-propionic acid methyl ester as colorless liquid.

MS: 482.2 (M+Na)$^+$, 460.2 (M+H)$^+$, 414.1, 383.1, 354.1, 293.3, 249.2, 208.1.

i] (2S)-3-{4-[2-(4-Chloro-phenyl)-thiazol-4-ylmethoxy]-2-ethyl-phenyl}-2-ethoxy-propionic acid

In analogy to the procedure described in example 10 d], (2S)-3-{4-[2-(4-chloro-phenyl)-thiazol-4-ylmethoxy]-2-ethyl-phenyl}-2-ethoxy-propionic acid methyl ester was treated with LiOH to obtain (2S)-3-{4-[2-(4-chloro-phenyl)-thiazol-4-ylmethoxy]-2-ethyl-phenyl}-2-ethoxy-propionic acid as light yellow solid.

MS: 444.1 (M−H)$^-$, 397.9, 353.7, 328.3, 232.7, 189.9.

Example 24

[rac]-2-Ethoxy-3-{3-fluoro-4-[2-(5-methyl-2-phenyl-thiazol-4-yl)-ethoxy]-phenyl}-propionic acid

In analogy to the procedure described in example 1 d], [rac]-2-ethoxy-3-(3-fluoro-4-hydroxy-phenyl)-propionic acid ethyl ester (example 7 a]) was reacted with 2-(5-methyl-2-phenyl-thiazol-4-yl)-ethanol [PCT Int. Appl. (2002), WO 02/18355 A1] in tetrahydrofuran in the presence of triphenylphosphine and DEAD (diethyl azodicarboxylate) to yield [rac]-2-ethoxy-3-{3-fluoro-4-[2-(5-methyl-2-phenyl-thiazol-4-yl)-ethoxy]-phenyl}-propionic acid ethyl ester, which was further saponified in analogy to the procedure described in example 4 e], to yield [rac]-2-ethoxy-3-3-fluoro-4-[2-(5-methyl-2-phenyl-thiazol-4-yl)-ethoxy]-phenyl}-propionic acid as an off-white solid.

MS: 428.2 (M−H)$^-$.

Example 25
[rac]-2-Ethoxy-3-(3-fluoro-4-{2-[2-(4-trifluoromethyl-phenyl)-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-[2-(4-trifluoromethyl-phenyl)-thiazol-4-yl]-ethanol (prepared from 4-chloromethyl-2-(4-trifluoromethyl-phenyl)-thiazole (example 18 a] and 4 a]) in analogy to the sequence described in examples 13 a] to 13 d]) in tetrahydrofuran in the presence of triphenylphosphine and DEAD (diethyl azodicarboxylate) to yield [rac]-2-ethoxy-3-(3-fluoro-4-{2-[2-(4-trifluoromethyl-phenyl)-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[2-(4-trifluoromethyl-phenyl)-thiazol-4-yl]-ethoxy}-phenyl)-propionic acid as a colorless gum.

MS: 482.2 (M–H)−.

Example 26
[rac]-2-Ethoxy-3-{3-fluoro-4-[2-(2-phenyl-thiazol-4-yl)-ethoxy]-phenyl}-propionic acid In analogy to the procedure described in example 1 d], [rac]-2-ethoxy-3-(3-fluoro-4-hydroxy-phenyl)-propionic acid ethyl ester (example 7 a]) was reacted with 2-(2-phenyl-thiazol-4-yl)-ethanol (prepared from thiobenzamide and 1,3-dichloroacetone in analogy to the procedure described in example 4 a] to give 4-chloromethyl-2-phenyl-thiazole followed by side chain elongation in analogy to the sequence described in examples 13 a] to 13 d]) in tetrahydrofuran in the presence of triphenylphosphine and DEAD (diethyl azodicarboxylate) to yield [rac]2-ethoxy-3-{3-fluoro-4-[2-(2-phenyl-thiazol-4-yl)-ethoxy]-phenyl}-propionic acid ethyl ester, which was further saponified in analogy to the procedure described in example 4 e], to yield [rac]2-ethoxy-3-{3-fluoro-4-[2-(2-phenyl-thiazol-4-yl)-ethoxy]-phenyl}-propionic acid as a light yellow gum.

MS: 414.2 (M–H)−.

Example 27
a] (4-Methyl-2-phenyl-thiazol-5-yl)-methanol

A solution of 5.9 g (23.85 mmol) of 4-methyl-2-phenyl-thiazole-5-carboxylic acid ethyl ester in 30 ml of absolute THF was added to a suspension of 1.1 g (29 mmol) of lithium aluminium hydride in 20 ml of THF, under an argon atmosphere at 0–5° C. Afterwards, the mixture was stirred at ambient temperature for 1 hour. Then, a small amount of water was added cautiously, followed by 50 ml of ethyl acetate and 20 g of anhydrous sodium sulfate and stirring was continued for 0.5 hours. Then, the reaction mixture was filtered, the filtrate was evaporated, leaving 3.85 g (78.6% of theory) of (4-methyl-2-phenyl-thiazol-5-yl)-methanol as yellow solid.

MS: 206.1 (M+H)+.

b] [rac]-2-Ethoxy-3-[3-fluoro-4-(4-methyl-2-phenyl-thiazol-5-ylmethoxy)-phenyl]-propionic acid In analogy to the procedure described in example 1 d], [rac]-2-ethoxy-3-(3-fluoro-4-hydroxy-phenyl)-propionic acid ethyl ester (example 7 a]) was reacted with (4-methyl-2-phenyl-thiazol-5-yl)-methanol in tetrahydrofuran in the presence of triphenylphosphine and DEAD (diethyl azodicarboxylate) to yield [rac]-2-ethoxy-3-[3-fluoro-4-(4-methyl-2-phenyl-thiazol-5-ylmethoxy)-phenyl]-propionic acid ethyl ester, which was further saponified in analogy to the procedure described in example 4 e], to yield [rac]-2-ethoxy-3-[3-fluoro-4-(4-methyl-2-phenyl-thiazol-5-ylmethoxy)-phenyl]-propionic acid as a light yellow solid.

MS: 414.1 (M–H)−.

Example 28
a] 4-Iodomethyl-2-phenyl-thiazole 2 g (13.35 mmol) of sodium iodide were added to a solution of 0.56 g (2.67 mmol) of 4-chloromethyl-2-phenyl-thiazole (prepared from thiobenzamide and 1,3-dichloroacetone in analogy to the procedure described in example 4 a]) in 10 ml of acetone and the suspension was stirred at reflux for 2 hours. After cooling to ambient temperature, 30 ml of tert-butyl methyl ether and 10 ml of water were added and the mixture was transferred to a separatory funnel. The organic phase was washed with water and brine, dried with anhydrous sodium sulfate and finally evaporated, leaving 0.8 g of 4-iodomethyl-2-phenyl-thiazole as light yellow solid (99% of theory).

MS: 300.9 (M)+.

b] 3-(2-Phenyl-thiazol-4-yl)-propionic acid ethyl ester

LDA was prepared by adding 4.7 ml of n-BuLi (1.6 M, hexane) to a solution of 0.76 g (7.5 mmol) of diisopropylamine in 3 ml of abs. THF at −5° C. Then, the mixture was cooled to −78° C., 0.77 g (8.74 mmol) of ethyl acetate were added and the mixture was kept for 15 minutes at that temperature to ensure complete deprotonation. Afterwards, 0.79 g (2.5 mmol) of 4-iodomethyl-2-phenyl-thiazole dissolved in 5 ml of abs. THF and 3 ml of 1,3-dimethyl-3,4,5,6-tetrahydro-2(1H)-pyrimidinon (DMPU) were added and stirring was continued for 0.5 hours at −78° C. Then, the reaction mixture was quenched with ammonium chloride solution, extracted twice with AcOEt, washed with water, dried over anhydrous sodium sulfate, and evaporated to dryness. The residue was chromatographed on silicagel with dichloromethane as eluent. 0.46 g of 3-(2-phenyl-thiazol-4-yl)-propionic acid ethyl ester were obtained as light yellow liquid (70% of theory).

MS: 262.1 (M+H)+.

c] 3-(2-Phenyl-thiazol-4-yl)-propan-1-ol

In analogy of the procedure described in example 12 b], 0.44 g (1.68 mmol) of 3-(2-phenyl-thiazol-4-yl)-propionic acid ethyl ester was reacted with lithium aluminium hydride, yielding 0.28 g of 3-(2-phenyl-thiazol-4-yl)-propan-1-ol as colorless liquid (75.8% of theory).

MS: 220.2 (M+H)+.

d] [rac]-2-Ethoxy-3-{3-fluoro-4-{3-(2-phenyl-thiazol-4-yl)-propoxy]-phenyl}-propionic acid In analogy to the procedure described in example 1 d], [rac]-2-ethoxy-3-(3-fluoro-4-hydroxy-phenyl)-propionic acid ethyl ester (example 7 a]) was reacted with 3-(2-phenyl-thiazol-4-yl)-propan-1-ol in tetrahydrofuran in the presence of triphenylphosphine and DEAD (diethyl azodicarboxylate) to yield [rac]-2-ethoxy-3-{3-fluoro-4-[3-(2-phenyl-thiazol-4-yl)-propoxy]-phenyl}-propionic acid ethyl ester, which was further saponified in analogy to the procedure described in example 4 e], to yield [rac]-2-ethoxy-3-{3-fluoro-4-[3-(2-phenyl-thiazol-4-yl)-propoxy]-phenyl}-propionic acid as a colorless gum.

MS: 428.3 (M–H)−.

Example 29
[rac]-2-Ethoxy-3-(3-fluoro-4-{2-[5-methyl-2-(4-trifluoromethyl-phenyl)-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-[5-methyl-2-(4-trifluoromethyl-phenyl)-thiazol-4-yl]-ethanol

[PCT Int. Appl. (2001), WO 01/00603 A1] in tetrahydrofuran in the presence of triphenylphosphine and DEAD (diethyl azodicarboxylate) to yield [rac]-2-ethoxy-3-(3-fluoro-4-{2-[5-methyl-2-(4-trifluoromethyl-phenyl)-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[5-methyl-2-(4-trifluoromethyl-phenyl)-thiazol-4-yl]-ethoxy}-phenyl)-propionic acid as a light yellow solid.

MS: 496.1 (M−H)⁻.

Example 30

[rac]-3-(4-{2-[2-(4-tert-Butyl-phenyl)-thiazol-4-yl]-ethoxy}-3-fluoro-phenyl)-2-ethoxy-propionic acid In analogy to the procedure described in example 1 d], [rac]-2-ethoxy-3-(3-fluoro-4-hydroxy-phenyl)-propionic acid ethyl ester (example 7 a]) was reacted with 2-[2-(4-tert-butyl-phenyl)-thiazol-4-yl]-ethanol (prepared from 2-(4-tert-butyl-phenyl)-4-chloromethyl-thiazole (example 4 a]) in analogy to the sequence described in examples 13 a] to 13 d]) in tetrahydrofuran in the presence of triphenylphosphine and DEAD (diethyl azodicarboxylate) to yield [rac]-3-(4-{2-[2-(4-tert-butyl-phenyl)-thiazol-4-yl]-ethoxy}-3-fluoro-phenyl)-2-ethoxy-propionic acid ethyl ester, which was further saponified in analogy to the procedure described in example 4 e], to yield [rac]-3-(4-{2-[2-(4-tert-butyl-phenyl)-thiazol-4-yl]-ethoxy}-3-fluoro-phenyl)-2-ethoxy-propionic acid as a light yellow solid.

MS: 470.2 (M−H)⁻.

Example 31 a] [rac]-2-Ethoxy-3-[2-methyl-4-(2-phenyl-thiazol-4-ylmethoxy)-phenyl]-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 4-chloromethyl-2-phenyl-thiazole (prepared from thiobenzamide and 1,3-dichloroacetone in analogy to the procedure described in example 4 a]) in the presence of cesium carbonate and potassium iodide to yield [rac]-2-ethoxy-3-[2-methyl-4-(2-phenyl-thiazol-4-ylmethoxy)-phenyl]-propionic acid ethyl ester as colorless liquid.

MS: 448.2 (M+Na)⁺, 426.3 (M+H)⁺, 380.2, 347.4, 291.3, 248.3, 215.3, 174.2.

b] [rac]-2-Ethoxy-3-[2-methyl-4-(2-phenyl-thiazol-4-ylmethoxy)-phenyl]-propionic acid In analogy to the procedure described in example 10 d], [rac]-2-ethoxy-3-[2-methyl-4-(2-phenyl-thiazol-4-ylmethoxy)-phenyl]-propionic acid ethyl ester was treated with LiOH to obtain [rac]-2-ethoxy-3-[2-methyl-4-(2-phenyl-thiazol-4-ylmethoxy)-phenyl]-propionic acid as colorless crystals.

MS: 396.2 (M−H)⁻, 350.2, 306.1, 255.0.

Example 32 a] [rac]-3-{4-[2-(2-Chloro-phenyl)-thiazol-4-ylmethoxy]-2-methyl-phenyl}-2-ethoxy-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 4-chloromethyl-2-(2-chloro-phenyl)-thiazole (prepared from 2-chloro-thiobenzamide and 1,3-dichloroacetone in analogy to the procedure described in example 4 a]) in the presence of cesium carbonate and potassium iodide to yield [rac]-3-{4-[2-(2-chloro-phenyl)-thiazol-4-ylmethoxy]-2-methyl-phenyl}-2-ethoxy-propionic acid ethyl ester as colorless liquid.

MS: 482.2 (M+Na)⁺, 460.2 (M+H)⁺, 426.2, 386.1, 347.4, 291.4, 248.3, 208.1.

b] [rac]-3-{4-[2-(2-Chloro-phenyl)-thiazol-4-ylmethoxy]-2-methyl-phenyl}-2-ethoxy-propionic acid In analogy to the procedure described in example 10 d], [rac]-3-{4-[2-(2-chloro-phenyl)-thiazol-4-ylmethoxy]-2-methyl-phenyl}-2-ethoxy-propionic acid ethyl ester was treated with LiOH to obtain [rac]-3-{4-[2-(2-chloro-phenyl)-thiazol-4-ylmethoxy]-2-methyl-phenyl}-2-ethoxy-propionic acid as colorless solid.

MS: 430.2 (M−H)⁻, 384.0, 313.0, 255.2.

Example 33 a] 2-(4tert-Butyl-phenyl)-4-methyl-thiazole-5-carboxylic acid ethyl ester

The solution of 3.87 g (20 mmol) of 4-tert-butyl-thiobenzamide and 3.45 g (21 mmol) of ethyl 2-chloro-acetoacetate in 15 ml of ethanol was heated at reflux for 3 hours. Afterwards, the reaction mixture was cooled to ambient temperature and a solution of 3 g of potassium bicarbonate in 15 ml of water was added and the mixture was stirred until the gas evolution ($CO_2$) had ceased. The compound was then extracted with 3 portions of 50 ml of tert-butyl methyl ether, the combined organic phases were washed with water, then with brine, dried over anhydrous sodium sulfate and finally evaporated. 5.3 g of 2-(4-tert-butyl-phenyl)-4-methyl-thiazole-5-carboxylic acid ethyl ester (87.4% of theory) were obtained as pale yellow viscous oil.

MS: 304.2 (M+H)⁺.

b] [2-(4-tert-Butyl-phenyl)-4-methyl-thiazol-5-yl]-methanol

In analogy to the procedure described for example 12 b], 5.3 g (17.4 mmol) of 2-(4-tert-butyl-phenyl)-4-methyl-thiazole-5-carboxylic acid ethyl ester were reduced to [2-(4-tert-butyl-phenyl)-4-methyl-thiazol-5-yl]-methanol with lithium aluminium hydride to give 4.3 g (94.1% of theory) of [2-(4-tert-butyl-phenyl)-4-methyl-thiazol-5-yl]-methanol as a pale yellow solid.

MS: 262.1 (M+H)⁺.

c] [rac]-3-{4-[2-(4-tert-Butyl-phenyl)-4-methyl-thiazol-5-ylmethoxy]-3-fluoro-phenyl}-2-ethoxy-propionic acid In analogy to the procedure described in example 1 d], [rac]-2-ethoxy-3-(3-fluoro-4-hydroxy-phenyl)-propionic acid ethyl ester (example 7 a]) was reacted with [2-(4-tert-butyl-phenyl)-4-methyl-thiazol-5-yl]-methanol in tetrahydrofuran in the presence of triphenylphosphine and DEAD (diethyl azodicarboxylate) to yield [rac]-3-{4-[2-(4-tert-butyl-phenyl)-4-methyl-thiazol-5-ylmethoxy]-3-fluoro-phenyl}-2-ethoxy-propionic acid ethyl ester, which was further saponified in analogy to the procedure described in example 4 e], to yield [rac]-3-{4-[2-(4-tert-butyl-phenyl)-4-methyl-thiazol-5-ylmethoxy]-3-fluoro-phenyl}-2-ethoxy-propionic acid as a light yellow solid.

MS: 470.2 (M−H)⁻.

Example 34

[rac]-3-(4-{2-[2-(4-tert-Butyl-phenyl)-5-methyl-thiazol-4-yl]-ethoxy}-3-methyl-phenyl)-2-ethoxy-propionic acid In analogy to the procedure described in example 1 d], [rac]-2-ethoxy-3-(4-hydroxy-3-methyl-phenyl)-propionic acid ethyl ester (example 4 c]) was reacted with 2-[2-(4-tert-butyl-phenyl)-5-methyl-thiazol-4-yl]-ethanol (example 12 b]) in tetrahydrofuran in the presence of triphenylphosphine and DEAD (diethyl azodicarboxylate) to yield [rac]-3-(4-{2-[2-(4-tert-butyl-phenyl)-5-methyl-thiazol-4-yl]-ethoxy}-3-methyl-phenyl)-2-ethoxy-propionic acid ethyl ester, which was further saponified in analogy to the procedure described in example 4 e], to yield [rac]-3-(4-{2-[2-

(4-tert-butyl-phenyl)-5-methyl-thiazol-4-yl]-ethoxy}-3-methyl-phenyl)-2-ethoxy-propionic acid as colorless solid.

MS: 480.4 (M–H)⁻.

Example 35

[rac]-2-Ethoxy-3-(3-fluoro-4-{2-[2-(4-methoxy-phenyl)-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-[2-(4-methoxy-phenyl)-thiazol-4-yl]-ethanol (prepared from 4-methoxy-thiobenzamide and 1,3-dichloroacetone in analogy to the procedure described in example 4 a] to yield 4-chloromethyl-2-(4-methoxy-phenyl)-thiazole, followed by side chain elongation in analogy to the sequence described in examples 13 a] to 13 d]) in tetrahydrofuran in the presence of triphenylphosphine and DEAD (diethyl azodicarboxylate) to yield [rac]-2-ethoxy-3-(3-fluoro-4-{2-[2-(4-methoxy-phenyl)-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[2-(4-methoxy-phenyl)-thiazol-4-yl]-ethoxy}-phenyl)-propionic acid as a light yellow solid.

MS: 444.2 (M–H)⁻.

Example 36 a] [rac]-3-{4-[2-(4-Chloro-phenyl)-4-methyl-thiazol-5-ylmethoxy]-2-methyl-phenyl}-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with [2-(4-chloro-phenyl)-4-methyl-thiazol-5-yl]-methanol (prepared from 4-chloro-thiobenzamide and ethyl 2-chloro-acetoacetate in analogy to the procedures described in examples 33 a] and 33 b]) in the presence of triphenylphosphine and diethyl azodicarboxylate to yield [rac]-3-{4-[2-(4-chloro-phenyl)-4-methyl-thiazol-5-ylmethoxy]-2-methyl-phenyl}-2-ethoxy-propionic acid ethyl ester as colorless oil.

MS: 474.2 (M+H)⁺, 402.5, 350.1, 321.2, 257.2, 243.3, 222.1.

b] [rac]-3-{4-[2-(4-Chloro-phenyl)-4-methyl-thiazol-5-ylmethoxy]-2-methyl-phenyl}-2-ethoxy propionic acid In analogy to the procedure described in example 10 d], [rac]-3-{4-[2-(4-chloro-phenyl)-4-methyl-thiazol-5-ylmethoxy]-2-methyl-phenyl}-2-ethoxy-propionic acid ethyl ester was treated with LiOH to obtain [rac]-3-{4-[2-(4-chloro-phenyl)-4-methyl-thiazol-5-ylmethoxy]-2-methyl-phenyl}-2-ethoxy-propionic acid as colorless liquid.

MS: 444.1 (M–H)⁻, 398.0, 354.0, 285.9, 242.1.

Example 37 a] [rac]-2-Ethoxy-3-{2-methyl-4-[4-methyl-2-(3-trifluoromethyl-phenyl)-thiazol-5-ylmethoxy]-phenyl}-propionic acid ethyl ester In analogy to the procedure described in example 10 c], [rac]-2-ethoxy-3-(4-hydroxy-2-methyl-phenyl)-propionic acid ethyl ester (example 10 b]) was reacted with [4-methyl-2-(3-trifluoromethyl-phenyl)-thiazol-5-yl]-methanol (prepared from 3-trifluoromethyl-thiobenzamide and ethyl 2-chloro-acetoacetate in analogy to the procedures described in examples 33 a] and 33 b]) in the presence of triphenylphosphine and diethyl azodicarboxylate to yield [rac]-2-ethoxy-3-{2-methyl-4-[4-methyl-2-(3-trifluoromethyl-phenyl)-thiazol-5-ylmethoxy]-phenyl})-propionic acid ethyl ester as colorless liquid.

MS: 530.3 (M+Na)⁺, 508.3 (M+H)⁺, 464.2, 391.2, 256.0, 207.2, 162.3.

b] [rac]-2-Ethoxy-3-{2-methyl-4-[4-methyl-2-(3-trifluoromethyl-phenyl)-thiazol-5-ylmethoxy]-phenyl}-propionic acid In analogy to the procedure described in example 10 d], [rac]-2-ethoxy-3-{2-methyl-4-[4-methyl-2-(3-trifluoromethyl-phenyl)-thiazol-5-ylmethoxy]-phenyl}-propionic acid ethyl ester was treated with LiOH to obtain [rac]-2-ethoxy-3-(2-methyl-4-[4-methyl-2-(3-trifluoromethyl-phenyl)-thiazol-5-ylmethoxy]-phenyl}-propionic acid as colorless oil.

MS: 502.2 (M+Na)⁺, 480.3 (M+H)⁺, 391.2, 279.2, 256.1.

Example 38 a] [rac]-3-{4-[2-(3-Chloro-4-fluoro-phenyl)-4-methyl-thiazol-5-ylmethoxy]-2-methyl-phenyl}-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with [2-(3-chloro-4-fluoro-phenyl)-4-methyl-thiazol-5-yl)-methanol (prepared from 3-chloro-4-fluoro-thiobenzamide and ethyl 2-chloro-acetoacetate in analogy to the procedures described in examples 33 a] and 33 b]) in the presence of triphenylphosphine and diethyl azodicarboxylate to yield [rac]-3-{4-[2-(3-chloro-4-fluoro-phenyl)-4-methyl-thiazol-5-ylmethoxy]-2-methyl-phenyl}-2-ethoxy-propionic acid ethyl ester as light yellow liquid.

MS: 493.2 (M+H)⁺, 454.4, 391.3, 279.2, 240.2.

b] [rac]-3-{4-[2-(3-Chloro-4-fluoro-phenyl)-4-methyl-thiazol-5-ylmethoxy]-2-methyl-phenyl}-2-ethoxy-propionic acid In analogy to the procedure described in example 10 d], [rac]-3-{4-[2-(3-chloro-4-fluoro-phenyl)-4-methyl-thiazol-5-ylmethoxy]-2-methyl-phenyl}-2-ethoxy-propionic acid ethyl ester was treated with LiOH to obtain [rac]-3-{4-[2-(3-chloro-4-fluoro-phenyl)-4-methyl-thiazol-5-ylmethoxy]-2-methyl-phenyl}-2-ethoxy-propionic acid as light yellow foam.

MS: 464.1 (M+H)⁺, 342.2, 310.1, 279.2, 274.1, 240.2.

Example 39

[rac]-2-Ethoxy-3-(4-{2-[2-(4-methoxy-phenyl)-5-methyl-thiazol-4-yl]-ethoxy}-3-methyl-phenyl)-propionic acid In analogy to the procedure described in example 1 d], [rac]-2-ethoxy-3-(4-hydroxy-3-methyl-phenyl)-propionic acid ethyl ester (example 4 c]) was reacted with 2-[2-(4-methoxy-phenyl)-5-methyl-thiazol-4-yl]-ethanol (prepared from [rac]-4-bromo-3-oxo-pentanoic acid methyl ester [PCT Int. Appl. (2001), WO 01/79202] and 4-methoxy-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(4-{2-[2-(4-methoxy-phenyl)-5-methyl-thiazol-4-yl]-ethoxy}-3-methyl-phenyl)-propionic acid ethyl ester, which was further saponified in analogy to the procedure described in example 4 e], to yield [rac]-2-ethoxy-3-(4-{2-[2-(4-methoxy-phenyl)-5-methyl-thiazol-4-yl]-ethoxy}-3-methyl-phenyl)-propionic acid as light yellow gum.

MS: 454.3 (M–H)⁻.

Example 40

[rac]-2-Ethoxy-3-(3-fluoro-4-{2-[2-(4-methoxy-phenyl)-5-methyl-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-[2-(4-methoxy-phenyl)-5-methyl-thiazol-4-yl]-ethanol (prepared from [rac]-4-bromo-3-oxo-pentanoic acid methyl ester [PCT Int. Appl. (2001), WO 01/79202] and 4-methoxy-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(3-fluoro-4-{2-[2-(4-methoxy-phenyl)-5-methyl-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[2-(4-methoxy-phenyl)-5-methyl-thiazol-4-yl]-ethoxy}-phenyl)-propionic acid as light yellow solid.

MS: 460.4 (M+H)$^+$.

Example 41

[rac]-2-Ethoxy-3-(3-fluoro-4-{2-[2-(4-isopropyl-phenyl)-5-methyl-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-[2-(4-isopropyl-phenyl)-5-methyl-thiazol-4-yl]-ethanol (prepared from [rac]-4-bromo-3-oxo-pentanoic acid methyl ester [PCT Int. Appl. (2001), WO 01/79202] and 4-isopropyl-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(3-fluoro-4-{2-[2-(4-isopropyl-phenyl)-5-methyl-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[2-(4-isopropyl-phenyl)-5-methyl-thiazol-4-yl]-ethoxy}-phenyl)-propionic acid as colorless gum.

MS: 470.2 (M–H)$^-$.

Example 42

[rac]-3-(4-{2-[2-(4-tert-Butyl-phenyl)-5-methyl-thiazol-4-yl]-ethoxy}-3-fluoro-phenyl)-2-ethoxy-propionic acid In analogy to the procedure described in example 1 d], [rac]-2-ethoxy-3-(3-fluoro-4-hydroxy-phenyl)-propionic acid ethyl ester (example 7 a]) was reacted with 2-[2-(4-tert-butyl-phenyl)-5-methyl-thiazol-4-yl]-ethanol (example 12 b]) in tetrahydrofuran in the presence of triphenylphosphine and DEAD (diethyl azodicarboxylate) to yield [rac]-3-(4-{2-[2-(4-tert-butyl-phenyl)-5-methyl-thiazol-4-yl]-ethoxy}-3-fluoro-phenyl)-2-ethoxy-propionic acid ethyl ester, which was further saponified in analogy to the procedure described in example 4 e], to yield [rac]-3-(4-{2-[2-(4-tert-butyl-phenyl)-5-methyl-thiazol-4-yl]-ethoxy}-3-fluoro-phenyl)-2-ethoxy-propionic acid as colorless solid.

MS: 484.3 (M–H)$^-$.

Example 43

[rac]-2-Ethoxy-3-(3-fluoro-4-{3-[2-(4-isopropyl-phenyl)-thiazol-4-yl]-propoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 3-[2-(4-isopropyl-phenyl)-thiazol-4-yl]-propan-1-ol (prepared from 4-chloromethyl-2-(4-isopropyl-phenyl)-thiazole (obtained from 4-isopropyl-thiobenzamide and 1,3-dichloroacetone in analogy to the procedure described in example 4 a]) according to the sequence described in examples 28 a] to c]) in tetrahydrofuran in the presence of triphenylphosphine and DEAD (diethyl azodicarboxylate) to yield [rac]-2-ethoxy-3-(3-fluoro-4-{3-[2-(4-isopropyl-phenyl)-thiazol-4-yl]-propoxy)-phenyl)-propionic acid ethyl ester, which was further saponified in analogy to the procedure described in example 4 e], to yield [rac]-2-ethoxy-3-(3-fluoro-4-{3-[2-(4-isopropyl-phenyl)-thiazol-4-yl]-propoxy}-phenyl)-propionic acid as light yellow gum.

MS: 470.2 (M–H)$^-$.

Example 44

[rac]-3-(4-{3-[2-(4-tert-Butyl-phenyl)-5-methyl-thiazol-4-yl]-propoxy}-3-fluoro-phenyl)-2-ethoxy-propionic acid In analogy to the procedure described in example 1 d], [rac]-2-ethoxy-3-(3-fluoro-4-hydroxy-phenyl)-propionic acid ethyl ester (example 7 a]) was reacted with 3-[2-(4-tert-butyl-phenyl)-5-methyl-thiazol-4-yl]-propan-1-ol (prepared from methanesulfonic acid 2-[2-(4-tert-butyl-phenyl)-5-methyl-thiazol-4-yl]-ethyl ester [obtained from 2-[2-(4-tert-butyl-phenyl)-5-methyl-thiazol-4-yl]-ethanol (example 12 b]) and methanesulfonyl chloride in pyridine at 0° C.] according to the sequence described in examples 13 a] to d]) in tetrahydrofuran in the presence of triphenylphosphine and DEAD (diethyl azodicarboxylate) to yield [rac]-3-(4-{3-[2-(4-tert-butyl-phenyl)-5-methyl-thiazol-4-yl]-propoxy}-3-fluoro-phenyl)-2-ethoxy-propionic acid ethyl ester, which was further saponified in analogy to the procedure described in example 4 e], to yield [rac]-3-(4-{3-[2-(4-tert-butyl-phenyl)-5-methyl-thiazol-4-yl]-propoxy}-3-fluoro-phenyl)-2-ethoxy-propionic acid as colorless solid.

MS: 500.3 (M+H)$^+$.

Example 45 a] [rac]-2-Ethoxy-3-(4-hydroxy-3,5-dimethyl-phenyl)-propionic acid ethyl ester

In analogy to the procedure described in example 1 a], 4-benzyloxy-3,5-dimethyl-benzaldehyde was reacted with (1,2-diethoxy-2-oxoethyl)triphenyl phosphonium chloride [Tetrahedron 50 (25), 7543–56 (1994)] to yield 3-(4-benzyloxy-3,5-dimethyl-phenyl)-2(Z,E)-ethoxy-acrylic acid ethyl ester. Hydrogenation of 3-(4-benzyloxy-3,5-dimethyl-phenyl)-2(Z,E)-ethoxy-acrylic acid ethyl ester as described in example 4 c] yielded [rac]-2-ethoxy-3-(4-hydroxy-3,5-dimethyl-phenyl)-propionic acid ethyl ester as light yellow viscous oil.

MS: 265.2 (M–H)$^-$.

b] [rac]-3-(4-{2-[2-(4-tert-Butyl-phenyl)-5-methyl-thiazol-4-yl]-ethoxy}-3,5-dimethyl-phenyl)-2-ethoxy-propionic acid In analogy to the procedure described in example 1 d], [rac]-2-ethoxy-3-(4-hydroxy-3,5-dimethyl-phenyl)-propionic acid ethyl ester was reacted with 2-[2-(4-tert-butyl-phenyl)-5-methyl-thiazol-4-yl]-ethanol (example 12 b]) in tetrahydrofuran in the presence of triphenylphosphine and DEAD (diethyl azodicarboxylate) to yield [rac]-3-(4-{2-[2-(4-tert-butyl-phenyl)-5-methyl-thiazol-4-yl]-ethoxy}-3,5-dimethyl-phenyl)-2-ethoxy-propionic acid ethyl ester, which was further saponified in analogy to the procedure described in example 4 e], to yield [rac]-3-(4-{2-[2-(4-tert-butyl-phenyl)-5-methyl-thiazol-4-yl]-ethoxy}-3,5-dimethyl-phenyl)-2-ethoxy-propionic acid as colorless solid.

MS: 494.4 (M–H)$^-$.

Example 46

[rac]-2-Ethoxy-3-(4-{2-[2-(4-isopropyl-phenyl)-5-methyl-thiazol-4-yl]-ethoxy}-3,5-dimethyl-phenyl)-propionic acid In analogy to the procedure described in example 1 d], [rac]-2-ethoxy-3-(4-hydroxy-3,5-dimethyl-phenyl)-propionic acid ethyl ester (example 45 a]) was reacted with 2-[2-(4-isopropyl-phenyl)-5-methyl-thiazol-4-yl]-ethanol (prepared from [rac]-4-bromo-3-oxo-pentanoic acid methyl ester [PCT Int. Appl. (2001), WO 01/79202] and 4-isopropyl-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(4-{2-[2-(4-isopropyl-phenyl)-5-methyl-thiazol-4-yl]-ethoxy}-3,5-dimethyl-phenyl)-propionic acid ethyl ester, which was further saponified in analogy to the procedure described in example 4 e], to yield [rac]-2-ethoxy-3-(4-{2-[2-(4-isopropyl-phenyl)-5-methyl-thiazol-4-yl]-ethoxy}-3,5-dimethyl-phenyl)-propionic acid as yellow amorphous solid.

MS: 480.3 (M−H)−.

Example 47

[rac]-2-Ethoxy-3-(4-{2-[2-(4-isopropyl-phenyl)-5-methyl-thiazol-4-yl]-ethoxy}-3-methyl-phenyl)-propionic acid In analogy to the procedure described in example 1 d], [rac]-2-ethoxy-3-(4-hydroxy-3-methyl-phenyl)-propionic acid ethyl ester (example 4 c]) was reacted with 2-[2-(4-isopropyl-phenyl)-5-methyl-thiazol-4-yl]-ethanol (prepared from [rac]-4-bromo-3-oxo-pentanoic acid methyl ester [PCT Int. Appl. (2001), WO 01/79202] and 4-isopropyl-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(4-{2-[2-(4-isopropyl-phenyl)-5-methyl-thiazol-4-yl]-ethoxy}-3-methyl-phenyl)-propionic acid ethyl ester, which was further saponified in analogy to the procedure described in example 4 e], to yield [rac]-2-ethoxy-3-(4-{2-[2-(4-isopropyl-phenyl)-5-methyl-thiazol-4-yl]-ethoxy}-3-methyl-phenyl)-propionic acid as light yellow solid.

MS: 466.3 (M−H)−.

Example 48 a] [rac]-2-Ethoxy-3-(4-hydroxy-3-methoxy-phenyl)-propionic acid ethyl ester

In analogy to the procedure described in example 1 a], 4-benzyloxy-3-methoxy-benzaldehyde was reacted with (1,2-diethoxy-2-oxoethyl)triphenyl phosphonium chloride [Tetrahedron 50 (25), 7543–56 (1994)] to yield 3-(4-benzyloxy-3-methoxy-phenyl)-2(Z,E)-ethoxy-acrylic acid ethyl ester. Hydrogenation of 3-(4-benzyloxy-3-methoxy-phenyl)-2(Z,E)-ethoxy-acrylic acid ethyl ester as described in example 4 c] yielded [rac]-2-ethoxy-3-(4-hydroxy-3-methoxy-phenyl)-propionic acid ethyl ester as colorless solid.

MS: 268.1 (M)+.

b] [rac]-3-(4-{2-[2-(4-tert-Butyl-phenyl)-5-methyl-thiazol-4-yl]-ethoxy}-3-methoxy-phenyl)-2-ethoxy-propionic acid In analogy to the procedure described in example 1 d], [rac]-2-ethoxy-3-(4-hydroxy-3-methoxy-phenyl)-propionic acid ethyl ester was reacted with 2-[2-(4-tert-butyl-phenyl)-5-methyl-thiazol-4-yl]-ethanol (example 12 b]) in tetrahydrofuran in the presence of triphenylphosphine and DEAD (diethyl azodicarboxylate) to yield [rac]-3-(4-{2-[2-(4-tert-butyl-phenyl)-5-methyl-thiazol-4-yl]-ethoxy}-3-methoxy-phenyl)-2-ethoxy-propionic acid ethyl ester, which was further saponified in analogy to the procedure described in example 4 e], to yield [rac]-3-(4-{2-[2-(4-tert-butyl-phenyl)-5-methyl-thiazol-4-yl]-ethoxy}-3-methoxy-phenyl)-2-ethoxy-propionic acid as light yellow amorphous solid.

MS: 496.4 (M−H)−.

Example 49

[rac]-2-Ethoxy-3-(3-fluoro-4-{2-[2-(4-isopropyl-phenyl)-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-2-(4-isopropyl-phenyl)-thiazol-4-yl]-ethanol (prepared from 4-chloromethyl-2-(4-isopropyl-phenyl)-thiazole (example 5) according to the sequence described in examples 13 a]to d]) in tetrahydrofuran in the presence of triphenylphosphine and DEAD (diethyl azodicarboxylate) to yield [rac]-2-ethoxy-3-(3-fluoro-4-{2-[2-(4-isopropyl-phenyl)-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[2-(4-isopropyl-phenyl)-thiazol-4-yl]-ethoxy}-phenyl)-propionic acid as light yellow solid.

MS: 456.3 (M+H)+.

Example 50

[rac]-2-Ethoxy-3-3-fluoro-4-[2-(2-p-tolyl-thiazol-4-yl)-ethoxy]-phenyl}-propionic acid In analogy to the procedure described in example 1 d], [rac]-2-ethoxy-3-(3-fluoro-4-hydroxy-phenyl)-propionic acid ethyl ester (example 7 a]) was reacted with 2-(2-p-tolyl-thiazol-4-yl)-ethanol (prepared from (2-p-tolyl-thiazol-4-yl)-acetic acid ethyl ester [Collection of Czechoslovak Chemical Communications (2001), 66(12), 1809–1830] with lithium aluminium hydride in analogy to the procedure described in example 12 b]) in tetrahydrofuran in the presence of triphenylphosphine and DEAD (diethyl azodicarboxylate) to yield [rac]-2-ethoxy-3-{3-fluoro-4-[2-(2-p-tolyl-thiazol-4-yl)-ethoxy]-phenyl}-propionic acid ethyl ester, which was further saponified in analogy to the procedure described in example 4 e], to yield [rac]-2-ethoxy-{3-fluoro-4-[2-(2-p-tolyl-thiazol-4-yl)-ethoxy)-phenyl}-propionic acid as light yellow solid.

MS: 428.3 (M+H)+.

Example 51 a] [rac]-2-Ethoxy-3-(4-hydroxy-naphthalen-1-yl)-propionic acid ethyl ester

In analogy to the procedure described in example 1 a], 4-benzyloxy-naphthalene-1-carbaldehyde (prepared from 4-hydroxy-naphthalene-1-carbaldehyde, benzylchloride, potassium carbonate in N,N-dimethylformamide at room temperature) was reacted with (1,2-diethoxy-2-oxoethyl) triphenyl phosphonium chloride [Tetrahedron 50(25), 7543–56(1994)] to yield 3-(4-benzyloxy-naphthalen-1-yl)-2-ethoxy-(Z,E)-acrylic acid ethyl ester. Hydrogenation of 3-(4-benzyloxy-naphthalen-1-yl)-2-ethoxy-(Z,E)-acrylic acid ethyl ester as described in example 2 c] yielded [rac]-2-ethoxy-3-(4-hydroxy-naphthalen-1-yl)-propionic acid ethyl ester as light brown oil.

MS: 288.3 (M)+, 242.2, 215.3, 157.2.

b] [rac]-2-Ethoxy-3-{4-[2-(5-methyl-2-phenyl-thiazol-4-yl)-ethoxy]-naphthalen-1-yl}-propionic acid In analogy to the procedure described in example 1 d], [rac]-2-ethoxy-3-(4-hydroxy-naphthalen-1-yl)-propionic acid ethyl ester was reacted with 2-(5-methyl-2-phenyl-thiazol-4-yl)-ethanol [PCT Int. Appl. (2002), WO 02/18355 A1] in tetrahydrofuran in the presence of triphenylphosphine and DIAD (diisopropyl azodicarboxylate) to yield [rac]-2-ethoxy-3-{4-[2-(5-methyl-2-phenyl-thiazol-4-yl)-ethoxy]-naphthalen-1-yl}-propionic acid ethyl ester, which was further saponified in analogy to the procedure described in example 1 e], to yield [rac]-2-ethoxy-3-{4-[2-(5-methyl-2-phenyl-thiazol-4-yl)-ethoxy]-naphthalen-1-yl}-propionic acid as colorless amorphous solid.

MS: 462.3 (M+H)+.

Example 52
[rac]-3-{4-[2-(2-Benzo[1.3]dioxol-5-yl-5-methyl-thiazol-4-yl)-ethoxy]-3-fluoro-phenyl}-2-ethoxy-propionic acid In analogy to the procedure described in example 1 d], [rac]-2-ethoxy-3-(3-fluoro-4-hydroxy-phenyl)-propionic acid ethyl ester (example 7 a]) was reacted with 2-(2-benzo[1,3]dioxol-5-yl-5-methyl-thiazol-4-yl)-ethanol (prepared from [rac]-4-bromo-3-oxo-pentanoic acid methyl ester [PCT Int. Appl. (2001), WO 01/792023 and benzo[1,3]dioxole-5-carbothioic acid amide in analogy to the procedures described in examples 12 a] and 12 b]) in tetrahydrofuran in the presence of triphenylphosphine and DEAD (diethyl azodicarboxylate) to yield [rac]-3-{4-[2-(2-benzo[1,3]dioxol-5-yl-5-methyl-thiazol-4-yl)-ethoxy]-3-fluoro-phenyl)-2-ethoxy-propionic acid ethyl ester, which was further saponified in analogy to the procedure described in example 4 e], to yield [rac]-3-{4-[2-(2-benzo[1,3]dioxol-5-yl-5-methyl-thiazol-4-yl)-ethoxy]-3-fluoro-phenyl}-2-ethoxy-propionic acid as colorless solid.

MS: 472.3 (M−H)⁻.

Example 53
[rac]-2-Ethoxy-3-{3-fluoro-4-[4-methyl-2-(4-trifluoromethyl-phenyl)-thiazol-5-ylmethoxy]-phenyl}-propionic acid In analogy to the procedure described in example 1 d], [rac]-2-ethoxy-3-(3-fluoro-4-hydroxy-phenyl)-propionic acid ethyl ester (example 7 a]) was reacted with [4-methyl-2-(4-trifluoromethyl-phenyl)-thiazol-5-yl]-methanol in tetrahydrofuran in the presence of triphenylphosphine and DEAD (diethyl azodicarboxylate) to yield [rac]-2-ethoxy-3-{3-fluoro-4-[4-methyl-2-(4-trifluoromethyl-phenyl)-thiazol-5-ylmethoxy]-phenyl}-propionic acid ethyl ester, which was further saponified in analogy to the procedure described in example 4 e], to yield [rac]-2-ethoxy-3-{3-fluoro-4-[4-methyl-2-(4-trifluoromethyl-phenyl)-thiazol-5-ylmethoxy]-phenyl}-propionic acid as light yellow solid,

MS: 482.2 (M−H)⁻.

Example 54
a] 3-(4-Benzyloxy-3-fluoro-phenyl)-3-hydroxy-2-isopropoxy-propionic acid ethyl ester (mixture of diastereomers)

LDA was prepared under an Ar atmosphere by adding 18.75 ml (30 mmol) of n-butyllithium solution (1.6 M in hexane) to a stirred solution of 3.13 g (31 mmol) of diisopropylamine in 20 ml of dry THF, at −5° C. After cooling to −78° C., 4.38 g of isopropoxy-acetic acid ethyl ester (Tetrahedron (1982), 38(17), 2733–9) (30 mmol) in 10 ml of THF was added and stirring was continued for 15 min. Then, 3.6 g of 4-benzyloxy-3-fluoro-benzaldehyde (prepared from 3-fluoro-4-hydroxy-benzaldehyde, benzyl bromide and cesium carbonate in acetonitrile) (15.6 mmol) dissolved in a mixture of 15 ml of THF and 20 ml of 1,3-dimethyl-3,4,5,6-tetrahydro-2(1H)-pyrimidinone (DMPU) were added and the reaction mixture was stirred at −78° C. for 30 min, and then at 0° C. for 30 min. Afterwards, it was quenched by addition of aqueous saturated ammonium chloride solution and the compound was extracted twice with ethyl acetate. The combined organic phases were washed with water, then brine, dried over anhydrous sodium sulfate and evaporated to dryness. The residue was chromatographed on silicagel (dichloromethane-diethyl ether 1/1 (v/v) as eluent). 4.9 g of 3-(4-benzyloxy-3-fluoro-phenyl)-3-hydroxy-2-isproxy-propionic acid ethyl ester (mixture of diastereomers) were obtained as colorless oil (83.3% of theory).

MS: 376.0 (M)⁺.

b] [rac]-3-(4-Benzyloxy-3-fluoro-phenyl)-2-isopropoxy-propionic acid ethyl ester To a cooled solution (ice bath) of 4.9 g of 3-(4-benzyloxy-3-fluoro-phenyl)-3-hydroxy-2-isproxy-propionic acid ethyl ester (mixture of diastereomers) (13 mmol) in 25 ml of trifluoroacetic acid, 23.8 ml of triethylsilane (26.5 mmol) and 15 ml of dichloromethane were added. The solution was stirred at 0° C. for 1 hour and at ambient temperature for 2 hours. Then, the reaction mixture was poured onto a mixture of water, sodium bicarbonate and ice. The compound was extracted with tert-butyl methyl ether and after evaporation to dryness, the residue was chromatographed on silicagel with dichloromethane as eluent. 3.27 g of [rac]-3-(4-benzyloxy-3-fluoro-phenyl)-2-isopropoxy-propionic acid ethyl ester were obtained as colorless oil (69.7% of theory).

MS: 360.2 (M)⁺.

c] [rac]-3-(3-Fluoro-4-hydroxy-phenyl)-2-isopropoxy-propionic acid ethyl ester 0.5 g of 10% palladium on charcoal were added to a solution of 3.7 g of [rac]-3-(4-benzyloxy-3-fluoro-phenyl)-2-isopropoxy-propionic acid ethyl ester (10.26 mmol) in 30 ml of THF and the compound was stirred under an atmosphere of $H_2$, at normal pressure and ambient temperature, until the absorption of gas stopped. After filtration of the catalyst and evaporation of the filtrate, 2.7 g of [rac]-3-(3-fluoro-4-hydroxy-phenyl)-2-isopropoxy-propionic acid ethyl ester were obtained as colorless viscous oil (97.3% of theory).

MS: 269.2 (M−H)⁻.

d] [rac]-3-{3-Fluoro-4-[4-methyl-2-(4-trifluoromethyl-phenyl)-thiazol-5-ylmethoxy]-phenyl}-2-isopropoxy-propionic acid In analogy to the procedure described in example 1 d], [rac]-3-(3-fluoro-4-hydroxy-phenyl)-2-isopropoxy-propionic acid ethyl ester was reacted with 14-methyl-2-(4-trifluoromethyl-phenyl)-thiazol-5-yl]-methanol in tetrahydrofuran in the presence of triphenylphosphine and DEAD (diethyl azodicarboxylate) to yield [rac]-3-{3-fluoro-4-[4-methyl-2-(4-trifluoromethyl-phenyl)-thiazol-5-ylmethoxy]-phenyl}-2-isopropoxy-propionic acid ethyl ester, which was further saponified in analogy to the procedure described in example 4 e], to yield [rac]-3-{3-fluoro-4-[4-methyl-2-(4-trifluoromethyl-phenyl)-thiazol-5-ylmethoxy]-phenyl}-2-isopropoxy-propionic acid as light yellow solid.

MS: 496.2 (M−H)⁻.

Example 55
[rac]-3-{4-[2-(3,5-Dimethoxy-phenyl)-thiazol-4-ylmethoxy]-3-fluoro-phenyl}-2-ethoxy-propionic acid In analogy to the procedure described in example 14 b], [rac]-2-ethoxy-3-(3-fluoro-4-hydroxy-phenyl)-propionic acid ethyl ester (example 7 a]) was reacted with 4-chloromethyl-2-(3,5-dimethoxy-phenyl)-thiazole (prepared from 3,5-dimethoxy-thiobenzamide and 1,3-dichloroacetone in analogy to the procedure described in example 4 a]) in the presence of cesium carbonate and potassium iodide to yield [rac]-3-{4-[2-(3,5-dimethoxy-phenyl)-thiazol-4-ylmethoxy]-3-fluoro-phenyl}-2-ethoxy-propionic acid ethyl ester, which was further saponified in analogy to the procedure described in example 4 e], to yield [rac]-3-{4-[2-(3,5-dimethoxy-phenyl)-thiazol-4-ylmethoxy]-3-fluoro-phenyl}-2-ethoxy-propionic acid as light yellow solid.

MS: 460.1 (M−H)⁻.

Example 56
[rac]-2-Ethoxy-3-[3-fluoro-4-(2-phenyl-thiazol-4-ylmethoxy)-phenyl]-propionic acid In analogy to the procedure described in example 14 b], [rac]-2-ethoxy-3-(3-fluoro-4-hydroxy-phenyl)-propionic acid ethyl ester (example 7 a]) was reacted with 4-chloromethyl-2-phenyl-thiazole (prepared from thiobenzamide and 1,3-dichloroacetone in analogy to the procedure described in example 4 a]) in the presence of cesium carbonate and potassium iodide to yield [rac]-2-ethoxy-3-[3-fluoro-4-(2-phenyl-thiazol-4-ylmethoxy)-phenyl]-propionic acid ethyl ester, which was further saponified in analogy to the procedure described in example 4 e], to yield [rac]-2-ethoxy-3-[3-fluoro-4-(2-phenyl-thiazol-4-ylmethoxy)-phenyl]-propionic acid as light yellow solid.

MS: 400.1 (M–H)$^-$.

Example 57
[rac]-2-Ethoxy-3-[3-fluoro-4-(2-p-tolyl-thiazol-4-ylmethoxy)-phenyl]-propionic acid In analogy to the procedure described in example 14 b], [rac]-2-ethoxy-3-(3-fluoro-4-hydroxy-phenyl)-propionic acid ethyl ester (example 7 a]) was reacted with 4-chloromethyl-2-p-tolyl-thiazole (prepared from 4 methyl-thiobenzamide and 1,3-dichloroacetone in analogy to the procedure described in example 4 a]) in the presence of cesium carbonate and potassium iodide to yield [rac]-2-ethoxy-3-[3-fluoro-4-(2-p-tolyl-thiazol-4-ylmethoxy)-phenyl]-propionic acid ethyl ester, which was further saponified in analogy to the procedure described in example 4 e], to yield [rac]-2-ethoxy-3-[3-fluoro-4-(2-p-tolyl-thiazol-4-ylmethoxy)-phenyl]-propionic acid as light yellow solid.

MS: 414.2 (M–H)$^-$.

Example 58
a] [rac]-3-(4-Benzyloxy-2-ethoxy-phenyl)-2-ethoxy-3-hydroxy-propionic acid ethyl ester [mixture of diastereomers]

LDA was prepared by adding 13.3 ml n-BuLi (1.5 M, hexane) to a solution of 2.85 ml (20.0 mmol) of diisopropylamine in 90 ml of abs. THF at –5° C. After cooling to –78° C., 2.81 ml (20.0 mmol) of ethyl ethoxyacetate, dissolved in 10 ml of abs. THF, was added and the mixture kept for 15 minutes at that temperature to ensure complete deprotonation. 2.05 g (8.0 mmol) of 4-benzyloxy-2-ethoxy-benzaldehyde [prepared from 2-hydroxy-4-benzyloxy-benzaldehyde and ethyl iodide in analogy to the procedure described for 4-benzyloxy-2-isopropoxy-benzaldehyde in Chemical & Pharmaceutical Bulletin (1998), 46(2), 222–230: 2-hydroxy-4-benzyloxy-benzaldehyde, isopropyl bromide, potassium iodide, potassium carbonate, N,N-dimethylformamide, 100° C.], dissolved in 20 ml of abs. THF, were then added. After stirring for 30 minutes at dry ice temperature, the reaction mixture was quenched with ammonium chloride solution, warmed up to 0° C., then extracted twice with AcOEt, washed with water, dried over sodium sulfate, and evaporated to dryness. Flash chromatography (SiO$_2$, hexane/AcOEt=9:1 to 1:1) yielded 3.09 g (99% of theory) of [rac]-3-(4-benzyloxy-2-ethoxy-phenyl)-2-ethoxy-3-hydroxy-propionic acid ethyl ester [mixture of diastereomers] as light yellow oil.

MS: 371.4 [(M+H)$^+$-H$_2$O].

b] 3-(4-Benzyloxy-2-ethoxy-phenyl)-2(Z,E)-ethoxy-acrylic add ethyl ester 3.26 g (8.39 mmol) of [rac]-3-(4-benzyloxy-2-ethoxy-phenyl)-2-ethoxy-3-hydroxy-propionic acid ethyl ester [mixture of diastereomers] and 0.15 g (0.84 mmol) 4-toluene sulfonic acid were stirred in 200 mol benzene at reflux for 30 minutes. Evaporation to dryness followed by flash chromatography (SiO$_2$, hexane/AcOEt=95:5 to 4:1) yielded 2.12 g (68% of theory) of 3-(4-benzyloxy-2-ethoxy-phenyl)-2(Z,E)-ethoxy-acrylic acid ethyl ester as light yellow oil.

MS: 370.1 (M)$^+$.

c] [rac]-2-Ethoxy-3-(2-ethoxy-4-hydroxy-phenyl)-propionic acid ethyl ester 0.90 g of Pd/C (10%) were added under argon to 4.49 g (12.1 mmol) of 3-(4-benzyloxy-2-ethoxy-phenyl)-2(Z,E)-ethoxy-acrylic acid ethyl ester dissolved in 80 ml of ethanol. The atmosphere was then replaced with H$_2$, and the suspension was rapidly stirred at room temperature for two hours. Filtration over dicalite and evaporation of the solvents left 4.23 g of a light brown oil. Flash chromatography (SiO$_2$, hexane/AcOEt=95:5 to 1:1) yielded 3.41 g (99% of theory) of [rac]-2-ethoxy-3-(2-ethoxy-4-hydroxy-phenyl)-propionic acid ethyl ester as light yellow oil.

MS: 281.0 (M–H)$^-$.

d] [rac]-2-Ethoxy-3-{2-ethoxy-4-[2-(5-methyl-2-phenyl-thiazol-4-yl)-ethoxy]-phenyl}-propionic acid In analogy to the procedure described in example 1 d], [rac]-2-ethoxy-3-(2-ethoxy-4-hydroxy-phenyl)-propionic acid ethyl ester was reacted with 2-(5-methyl-2-phenyl-thiazol-4-yl)-ethanol [PCT Int. Appl. (2002), WO 02/18355 A1] in tetrahydrofuran in the presence of triphenylphosphine and DBAD (di-tert-butyl azodicarboxylate) to yield [rac]-2-ethoxy-3-{2-ethoxy-4-[2-(5-methyl-2-phenyl-thiazol-4-yl)-ethoxy]-phenyl}-propionic acid ethyl ester, which was further saponified in analogy to the procedure described in example 1 e], to yield [rac]-2-ethoxy-3-{2-ethoxy-4-[2-(5-methyl-2-phenyl-thiazol-4-yl)-ethoxy]-phenyl}-propionic acid as colorless oil.

MS: 454.3 (M–H)$^-$.

Example 59
[rac]-2-Ethoxy-3-(2-ethoxy-4-{2-[5-methyl-2-(4-trifluoromethyl-phenyl)-thiazol-4-yl]-ethoxy}-phenyl)-propionic acid In analogy to the procedure described in example 1 d], [rac]-2-ethoxy-3-(2-ethoxy-4-hydroxy-phenyl)-propionic acid ethyl ester (example 58 c]) was reacted with 2-[5-methyl-2-(4-trifluoromethyl-phenyl)-thiazol-4-yl]-ethanol [PCT Int. Appl. (2001), WO 01/00603 A1] in tetrahydrofuran in the presence of triphenylphosphine and DBAD (di-tert-butyl azodicarboxylate) to yield [rac]-2-ethoxy-3-(2-ethoxy-4-{2-[5-methyl-2-(4-trifluoromethyl-phenyl)-thiazol-4-yl]-ethoxy}-phenyl)-propionic acid ethyl ester, which was further saponified in analogy to the procedure described in example 1 e], to yield [rac]-2-ethoxy-3-(2-ethoxy-4-{2-[5-methyl-2-(4-trifluoromethyl-phenyl)-thiazol-4-yl]-ethoxy}-phenyl)-propionic acid as colorless oil.

MS: 522.3 (M–H)$^-$.

Example 60
[rac]-2-Ethoxy-3-(3-methyl-4-{2-[-5-methyl-2-(4-trifluoromethoxy-phenyl)-thiazol-4-yl]-ethoxy}-phenyl-propionic acid In analogy to the procedure described in example 1 d], [rac]-2-ethoxy-3-(4-hydroxy-3-methyl-phenyl)-propionic acid ethyl ester (example 4 c]) was reacted with 2-[5-methyl-2-(4-trifluoromethoxy-phenyl)-thiazol-4-yl]-ethanol (prepared from [rac]-4-bromo-3-oxo-pentanoic acid methyl ester [PCT Int. Appl. (2001), WO 01/79202] and 4-trifluoromethoxy-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(3-methyl-4-{2-[5-methyl-2-(4-trifluoromethoxy-phenyl)-thiazol-4-yl]-ethoxy}-phenyl)-propionic acid ethyl ester, which was further saponified in analogy to the procedure described in example 4 e], to yield [rac]-2-ethoxy-3-(3-methyl-4-{2-[5-methyl-2-(4-trifluoromethoxy-phenyl)-thiazol-4-yl]-ethoxy}-phenyl)-propionic acid as light yellow solid.

MS: 508.3 (M–H)⁻.

Example 61

[rac]-2-Ethoxy-3-(3-fluoro-4-{2-[5-methyl-2-(4-trifluoromethoxy-phenyl)-thiazol-4-yl]-ethoxy}-phenyl)-propionic acid In analogy to the procedure described in example 1 d], [rac]-2-ethoxy-3-(3-fluoro-4-hydroxy-phenyl)-propionic acid ethyl ester (example 7 a]) was reacted with 2-[5-methyl-2-(4-trifluoromethoxy-phenyl)-thiazol-4-yl]-ethanol (prepared from [rac]-4-bromo-3-oxo-pentanoic acid methyl ester [PCT Int. Appl. (2001), WO 01/79202] and 4-trifluoromethoxy-thiobenzamide in analogy to the procedures described in examples 12 a] and 12 b]) in tetrahydrofuran in the presence of triphenylphosphine and DEAD (diethyl azodicarboxylate) to yield [rac]-2-ethoxy-3-(3-fluoro-4-{2-[5-methyl-2-(4-trifluoromethoxy-phenyl)-thiazol-4-yl]-ethoxy}-phenyl)-propionic acid ethyl ester, which was further saponified in analogy to the procedure described in example 4 e], to yield [rac]-2-ethoxy-3-(3-fluoro-4-{2-[5-methyl-2-(4-trifluoromethoxy-phenyl)-thiazol-4-yl]-ethoxy}-phenyl)-propionic acid as colorless solid.

MS: 514.2 (M+H)⁺.

Example 62

[rac]-2-Isopropoxy-3-3-methoxy-4-[2-(5-methyl-2-p-tolyl-thiazol-4-yl)-ethoxy]-phenyl}-propionic acid In analogy to the procedure described in example 1 d], [rac]-3-(4-hydroxy-3-methoxy-phenyl)-2-isopropoxy-propionic acid ethyl ester [prepared from isopropoxy-acetic acid ethyl ester (Tetrahedron (1982), 38(17), 2733–9) and 4-benzyloxy-3-methoxy-benzaldehyde in analogy to the procedures described in examples 54 a]to c)] was reacted with 2-(5-methyl-2-p-tolyl-thiazol-4-yl)-ethanol (prepared from [rac]4-bromo-3-oxo-pentanoic acid methyl ester [PCT Int. Appl. (2001), WO 01/79202] and 4-methyl-thiobenzamide in analogy to the procedures described in examples 12 a] and 12 b]) in tetrahydrofuran in the presence of triphenylphosphine and DEAD (diethyl azodicarboxylate) to yield [rac]-2-isopropoxy-3-{3-methoxy-4-[2-(5-methyl-2-p-tolyl-thiazol-4-yl)-ethoxy]-phenyl)-propionic acid ethyl ester, which was further saponified in analogy to the procedure described in example 4 e], to yield [rac]-2-isopropoxy-3-{3-methoxy-4-[2-(5-methyl-2-p-tolyl-thiazol-4-yl)-ethoxy]-phenyl}-propionic acid as colorless amorphous solid.

MS: 470.2 (M+H)⁺.

Example 63

[rac]-3-(3-Fluoro-4-{2-[2-(4-trifluoromethyl-phenyl)-thiazol-4-yl]-ethoxy}-phenyl)-2-isopropoxy-propionic acid In analogy to the procedure described in example 1 d], [rac]-3-(3-fluoro-4-hydroxy-phenyl)-2-isopropoxy-propionic acid ethyl ester [example 54 c]) was reacted with 2-[2-(4-trifluoromethyl-phenyl)-thiazol-4-yl]-ethanol (prepared from 4-chloromethyl-2-(4-trifluoromethyl-phenyl)-thiazole (example 18 a]and 4 a]) in analogy to the sequence described in examples 13 a] to 13 d]) in tetrahydrofuran in the presence of triphenylphosphine and DEAD (diethyl azodicarboxylate) to yield [rac]-3-(3-fluoro-4-{2-[2-(4-trifluoromethyl-phenyl)-thiazol-4-yl]-ethoxy}-phenyl)-2-isopropoxy-propionic acid ethyl ester, which was further saponified in analogy to the procedure described in example 4 e], to yield [rac]-3-(3-fluoro-4-{2-[2-(4-trifluoromethyl-phenyl)-thiazol-4-yl]-ethoxy}-phenyl)-2-isopropoxy-propionic acid as colorless solid.

MS: 498.2 (M+H)⁺.

Example 64

[rac]-3-(4-{2-[2-(3,4-Dimethoxy-phenyl)-5-methyl-thiazol-4-yl]-ethoxy}-3-methoxy-phenyl)-2-ethoxy-propionic acid In analogy to the procedure described in example 1 d], [rac]-2-ethoxy-3-(4-hydroxy-3-methoxy-phenyl)-propionic acid ethyl ester [example 48 a]) was reacted with 2-[2-(3,5-dimethoxy-phenyl)-5-methyl-thiazol-4-yl)-ethanol (prepared from [rac]-4-bromo-3-oxo-pentanoic acid methyl ester [PCT Int. Appl. (2001), WO 01/79202] and 3,5-dimethoxy-thiobenzamide [PCT Int. Appl. (1992), WO 92/09586 A1] in analogy to the procedures described in examples 12 a] and 12 b]) in tetrahydrofuran in the presence of triphenylphosphine and DEAD (diethyl azodicarboxylate) to yield [rac]-3-(4-{2-[2-(3,4-dimethoxy-phenyl)-5-methyl-thiazol-4-yl]-ethoxy}-3-methoxy-phenyl)-2-ethoxy-propionic acid ethyl ester, which was further saponified in analogy to the procedure described in example 4 e], to yield [rac]-3-(4-{2-[2-(3,4-dimethoxy-phenyl)-5-methyl-thiazol-4-yl]-ethoxy}-3-methoxy-phenyl)-2-ethoxy-propionic acid as light yellow solid.

MS: 500.3 (M–H)⁻.

Example 65

[rac]-3-(4-{2-[2-(3,5-Dimethoxy-phenyl)-5-methyl-thiazol-4-yl]-ethoxy}-3-methoxy-phenyl)-2-isopropoxy-propionic acid In analogy to the procedure described in example 1 d], [rac]-3-(4-hydroxy-3-methoxy-phenyl)-2-isopropoxy-propionic acid ethyl ester [prepared from isopropoxy-acetic acid ethyl ester (Tetrahedron (1982), 38(17), 2733–9) and 4-benzyloxy-3-methoxy-benzaldehyde in analogy to the procedures described in examples 54 a]to c)] was reacted with 2-[2-(3,5-dimethoxy-phenyl)-5-methyl-thiazol-4-yl]-ethanol (prepared from [rac]-4-bromo-3-oxo-pentanoic acid methyl ester [PCT Int. Appl. (2001), WO 01/79202] and 3,5-dimethoxy-thiobenzamide [PCT Int. Appl. (1992), WO 92/09586 A1] in analogy to the procedures described in examples 12 a] and 12 b]) in tetrahydrofuran in the presence of triphenylphosphine and DEAD (diethyl azodicarboxylate) to yield [rac]-3-(4-{2-[2-(3,5-dimethoxy-phenyl)-5-methyl-thiazol-4-yl]-ethoxy}-3-methoxy-phenyl)-2-isopropoxy-propionic acid ethyl ester, which was further saponified in analogy to the procedure described in example 4 e], to yield [rac]-3-(4-{2-[2-(3,5-dimethoxy-phenyl)-5-methyl-thiazol-4-yl]-ethoxy}-3-methoxy-phenyl)-2-isopropoxy-propionic acid as colorless solid.

MS: 514.3 (M–H)⁻.

Example 66

[rac]-3-(4-{2-[2-(3,5-Dimethyl-phenyl)-5-methyl-thiazol-4-yl]-ethoxy}-3-methoxy-phenyl)-2-isopropoxy-propionic acid In analogy to the procedure described in example 1 d], [rac]-3-(4-hydroxy-3-methoxy-phenyl)-2-isopropoxy-propionic acid ethyl ester [prepared from isopropoxy-acetic acid ethyl ester (Tetrahedron (1982), 38(17), 2733–9) and 4-benzyloxy-3-methoxy-benzaldehyde in analogy to the procedures described in examples 54 a]to c)] was reacted with 2-[2-(3,5-dimethyl-phenyl)-5-methyl-thiazol-4-yl]- ethanol (prepared from [rac]-4-bromo-3-oxo-pentanoic acid methyl ester [PCT Int. Appl. (2001), WO 01/79202] and 3,5-dimethyl-thiobenzamide (from 3,5-dimethyl-benzonitrile and NaSH, NH$_4$Cl in N,N-dimethylformamide) in analogy to the procedures described in examples 12 a] and 12 b]) in tetrahydrofuran in the presence of triphenylphosphine and DEAD (diethyl azodicarboxylate) to yield [rac]-3-(4-{2-[2-(3,5-dimethyl-phenyl)-5-methyl-thiazol-4-yl]-ethoxy}-3-methoxy-phenyl)-2-isopropoxy-propionic acid ethyl ester, which was farther saponified in analogy to the procedure described in example 4 e], to yield [rac]-3-(4-{2-[2-(3,5-dimethyl-phenyl)-5-methyl-thiazol-4-yl]-ethoxy}-3-methoxy-phenyl)-2-isopropoxy-propionic acid as light yellow solid.

MS: 482.3 (M−H)$^-$.

Example 67

[rac]-3-(4-{2-[2-(3,5-Dimethyl-phenyl)-5-methyl-thiazol-4-yl]-ethoxy}-3-methoxy-phenyl)-2-ethoxy-propionic acid In analogy to the procedure described in example 1 d], [rac]-2-ethoxy-3-(4-hydroxy-3-methoxy-phenyl)-propionic acid ethyl ester [example 48 a)] was reacted with 2-[2-(3,5-dimethyl-phenyl)-5-methyl-thiazol-4-yl]-ethanol (prepared from [rac]-4-bromo-3-oxo-pentanoic acid methyl ester [PCT Int. Appl. (2001), WO 01/79202] and 3,5-dimethyl-thiobenzamide (from 3,5-dimethyl-benzonitrile and NaSH, NH$_4$Cl in N,N-dimethylformamide) in analogy to the procedures described in examples 12 a] and 12 b]) in tetrahydrofuran in the presence of triphenylphosphine and DEAD (diethyl azodicarboxylate) to yield [rac]-3-(4-{2-[2-(3,5-dimethyl-phenyl)-5-methyl-thiazol-4-yl]-ethoxy}-3-methoxy-phenyl)-2-ethoxy-propionic acid ethyl ester, which was further saponified in analogy to the procedure described in example 4 e], to yield [rac]-3-(4-{2-[2-(3,5-dimethyl-phenyl)-5-methyl-thiazol-4-yl]-ethoxy}-3-methoxy-phenyl)-2-ethoxy-propionic acid as colorless solid.

MS: 468.3 (M−H)$^-$.

Example 68 a] [rac]2-Ethoxy-3-(5-ethoxy-2-fluoro-4-hydroxy-phenyl)-propionic acid ethyl ester In analogy to the procedure described in example 1 a], 4-benzyloxy-5-ethoxy-2-fluoro-benzaldehyde [prepared from 5-ethoxy-2-fluoro-4-hydroxy-benzaldehyde [PCT Int. Appl. (2001), WO 01/90051 A1] and benzyl bromide, cesium carbonate in acetonitrile was reacted with (1,2-diethoxy-2-oxoethyl)triphenyl phosphonium chloride [Tetrahedron 50 (25), 7543–56 (1994)] to yield 3-(4-benzyloxy-5-ethoxy-2-fluoro-phenyl)-2(Z,E)-ethoxy-acrylic acid ethyl ester. Hydrogenation of 3-(4-benzyloxy-5-ethoxy-acrylic acid ethyl ester as described in example 4 c] yielded [rac]-2-ethoxy-3-(5-ethoxy-2-fluoro-4-hydroxy-phenyl)-propionic acid ethyl ester as colorless viscous oil.

MS: 299.2 (M−H)$^-$.

b] [rac]-2-Ethoxy-3-{5-ethoxy-2-fluoro-4-[2-(4-isopropyl-phenyl)-thiazol-4-ylmethoxy]-phenyl}-propionic acid In analogy to the procedure described in example 4 d], [rac]-2-ethoxy-3-(5-ethoxy-2-fluoro-4-hydroxy-phenyl)-propionic acid ethyl ester was reacted with 4-chloromethyl-2-(4-isopropyl-phenyl)-thiazole (prepared from 4-isopropyl-thiobenzamide and 1,3-dichloroacetone in analogy to the procedure described in example 4 a]) in acetonitrile in the presence of cesium carbonate to yield [rac]-2-ethoxy-3-{5-ethoxy-2-fluoro-4-[2-(4-isopropyl-phenyl)-thiazol-4-ylmethoxy]-phenyl}-propionic acid ethyl ester, which was further saponified in analogy to the procedure described in example 4 e], to yield [rac]-2-ethoxy-3-{5-ethoxy-2-fluoro-4-[2-(4-isopropyl-phenyl)-thiazol-4-ylmethoxy]-phenyl}-propionic acid as light yellow solid.

MS: 486.3 (M−H)$^-$.

Example 69

[rac]-3-(4-{2-[2-(4-Chloro-phenyl)-5-methyl-thiazol-4-yl]-ethoxy}-5-ethoxy-2-fluoro-phenyl)-2-ethoxy-propionic acid In analogy to the procedure described in example 4 d], [rac]-2-ethoxy-3-(5-ethoxy-2-fluoro-4-hydroxy-phenyl)-propionic acid ethyl ester [example 68 a]] was reacted with 2-[2-(4-chloro-phenyl)-5-methyl-thiazol-4-yl]-ethanol (prepared from [rac]-4-bromo-3-oxo-pentanoic acid methyl ester [PCT Int. Appl. (2001), WO 01/79202] and 4-chloro-thiobenzamide in analogy to the procedures described in examples 12 a] and 12 b]) in tetrahydrofuran in the presence of triphenylphosphine and DEAD (diethyl azodicarboxylate) to yield [rac]-3-(4-{2-[2-(4-chloro-phenyl)-5-methyl-thiazol-4-yl]-ethoxy}-5-ethoxy-2-fluoro-phenyl)-2-ethoxy-propionic acid ethyl ester, which was further saponified in analogy to the procedure described in example 4 e], to yield [rac]-3-(4-{2-[2-(4-chloro-phenyl)-5-methyl-thiazol-4-yl]-ethoxy}-5-ethoxy-2-fluoro-phenyl)-2-ethoxy-propionic acid as light yellow solid.

MS: 508.1 (M+H)$^+$.

Example 70 a] [rac]-3-(3,5-Difluoro-4-hydroxy-phenyl)-2-ethoxy-propionic acid ethyl ester

In analogy to the procedure described in example 1 a], 4-benzyloxy-3,5-difluoro-benzaldehyde [prepared from 3,5-difluoro-4-hydroxy-benzaldehyde [Journal of Medicinal Chemistry (1989), 32(2), 450–5] and benzyl bromide, cesium carbonate in acetonitrile] was reacted with (1,2-diethoxy-2-oxoethyl)triphenyl phosphonium chloride [Tetrahedron 50 (25), 7543–56 (1994)] to yield 3-(4-benzyloxy-3,5-difluoro-phenyl)-2(Z,E)-ethoxy-acrylic acid ethyl ester. Hydrogenation of 3-(4-benzyloxy-3,5-difluoro-phenyl)-2(Z,E)-ethoxy-acrylic acid ethyl ester as described in example 4 c] yielded 3-(3,5-difluoro-4-hydroxy-phenyl)-2(Z,E)-ethoxy-acrylic acid ethyl ester. In order to hydrogenate the double bond in the acrylic acid part, 3-(3,5-difluoro-4-hydroxy-phenyl)-2(Z,E)-ethoxy-acrylic acid ethyl ester has been saponified to 3-(3,5-difluoro-4-hydroxy-phenyl)-2 (Z,E)-ethoxy-acrylic acid. 3-(3,5-Difluoro-4-hydroxy-phenyl)-2(Z,E)-ethoxy-acrylic acid was hydrogenated with palladium on charcoal in acetic acid giving [rac]-3-(3,5-difluoro-4-hydroxy-phenyl)-2-ethoxy-propionic acid which was subsequently re-esterified in ethanol in the presence of p-toluenesulfonic acid to give [rac]-3-(3,5-difluoro-4-hydroxy-phenyl)-2-ethoxy-propionic acid ethyl ester as light yellow viscous oil.

MS: 274 (M)$^+$.

b] [rac]-3-(4-{2-[2-(3,5-Dimethoxy-phenyl)-5-methyl-thiazol-4-yl]-ethoxy}-3,5-difluoro-phenyl)-2-ethoxy-propionic acid In analogy to the procedure described in example 1 d], [rac]-3-(3,5-difluoro-4-hydroxy-phenyl)-2-ethoxy-propionic acid ethyl ester was reacted with 2-[2-(3,5-dimethoxy-phenyl)-5-methyl-thiazol-4-yl]-ethanol (prepared from [rac]-4-bromo-3-oxo-pentanoic acid methyl ester [PCT Int. Appl. (2001), WO 01/79202] and 3,5-dimethoxy-thiobenzamide [PCT Int. Appl. (1992), WO 92/09586 A1] in analogy to the procedures described in examples 12 a] and 12 b]) in tetrahydrofuran in the presence of triphenylphosphine and DEAD (diethyl azodicarboxylate) to yield [rac]-3-(4-{2-[2-(3,5-dimethoxy-phenyl)-5-methyl-thiazol-4-yl]-ethoxy}-3,5-difluoro-phenyl)-2-ethoxy-propionic acid ethyl ester, which was further saponified in analogy to the procedure described in example 4 e], to yield [rac]-3-(4-{2-[2-(3,5-dimethoxyphenyl)-5-methyl-thiazol-4-yl]-ethoxy}-3,5-difluoro-phenyl)-2-ethoxy-propionic acid as colorless solid.
MS: 506.1 (M–H)⁻.

Example 71
[rac]-3-(4-{2-[2-(4-Chloro-phenyl)-5-methyl-thiazol-4-yl]-ethoxy}-3,5-difluoro-phenyl)-2-ethoxy-propionic acid In analogy to the procedure described in example 4 d], [rac]-3-(3,5-difluoro-4-hydroxy-phenyl)-2-ethoxy-propionic acid ethyl ester [example 70 a]] was reacted with 2-[2-(4-chloro-phenyl)-5-methyl-thiazol-4-yl]-ethanol (prepared from [rac]-4-bromo-3-oxo-pentanoic acid methyl ester [PCT Int. Appl. (2001), WO 01/79202] and 4-chloro-thiobenzamide in analogy to the procedures described in examples 12 a] and 12 b]) in tetrahydrofuran in the presence of triphenylphosphine and DEAD (diethyl azodicarboxylate) to yield [rac]-3-(4-{2-[2-(4-chloro-phenyl)-5-methyl-thiazol-4-yl]-ethoxy}-3,5-difluoro-phenyl)-2-ethoxy-propionic acid ethyl ester, which was further saponified in analogy to the procedure described in example 4 e], to yield [rac]-3-(4-{2-[2-(4-chloro-phenyl)-5-methyl-thiazol-4-yl]-ethoxy}-3,5-difluoro-phenyl)-2-ethoxy-propionic acid as light yellow amorphous solid.
MS: 480.1 (M–H)⁻.

Example 72
a] [rac]-4-[2-(5-Methyl-2-p-tolyl-thiazol-4-yl)-ethoxy]-benzo[b]thiophene-7-carbaldehyde 0.275 g of the above prepared (example 62) 2-(5-methyl-2-p-tolyl-thiazol-4-yl)-ethanol (1.18 mmol) was dissolved in 6 ml of toluene and treated successively at 0° C. with 0.210 g of 4-hydroxy-benzo[b]thiophene-7-carbaldehyde (1.18 mmol), 0.309 g of triphenylphosphine (1.18 mmol), and 0.238 g (1.18 mmol) of DIAD. The cooling bath was then removed and stirring continued for 6 h. Pouring onto crashed ice, twofold extraction with AcOEt, washing with dil. NaOH, water and NH₄Cl-solution, drying over magnesium sulfate, and evaporation of the solvents, followed by flash chromatography (SiO₂, hexane/AcOEt=8/2), produced finally 0.201 g of the title compound as colorless oil.
MS: 394.1 (M+H)⁺.

b] [rac]-2-Ethoxy-3-hydroxy-3-{4-[2-(5-methyl-2-p-tolyl-thiazol-4-yl)-ethoxy]-benzo[b]thiophen-7-yl}-propionic acid ethyl ester LDA-solution in THF was prepared according to standard procedure from 0.102 g of diisopropylamine (1.0 mmol) and 0.61 ml of 1.5 M nBuLi (hexane) in 2 ml of abs. THF at –10° C. After cooling to –75° C., 0.121 g of ethyl ethoxyacetate (0.92 mmol), dissolved in 1 ml of THF, was added and stirring continued for 30 min. to complete enolate formation. 0.120 g of the above prepared [rac]-4-[2-(5-methyl-2-p-tolyl-thiazol-4-yl)-ethoxy]-benzo[b]thiophene-7-carbaldehyde (0.305 mmol), dissolved in 2 ml of THF, was then added at –75° C. and the mixture kept for another 30 min. at this temperature. Pouring onto crashed ice/NH₄Cl, twofold extraction with AcOEt, washing with water, drying over magnesium sulfate, and evaporation of the solvents, followed by flash chromatography (SiO₂, hexane/AcOEt=7/3) delivered 0.139 g of the title compound (syn/anti-isomers) as yellowish oil.
MS: 526.3 (M+H)⁺.

c] [rac]-2-Ethoxy-3-[4-2-(5-methyl-2-p-tolyl-thiazol-4-yl)-ethoxy]-benzo[b]thiophen-7-yl}-propionic acid ethyl ester 0.138 g of the above prepared [rac]-2-ethoxy-3-hydroxy-3-{4-[2-(5-methyl-2-p-tolyl-thiazol-4-yl)-ethoxy]-benzo[b]thiophen-7-yl}-propionic acid ethyl ester (0.263 mmol) was dissolved in 1.3 ml of trifluoroacetic acid, treated at 0° C. with 0.417 ml of triethylsilane (10 eq.) and then kept for 4 h at 0° C. under vigorous stirring, when TLC indicated the disappearance of starting material. The reaction mixture was then poured onto crashed ice/AcOEt/NaHCO₃, the organic layer washed with water (pH of aq. phase-8) and brine, dried over magnesium sulfate, and evaporated to dryness. Flash chromatography (SiO₂, hexane/AcOEt=82/18) yielded 0.090 g of the title compound as colorless oil.
MS: 510.4 (M+H)⁺.

d] [rac]-2-Ethoxy-3-{4-[2-(5-methyl-2-p-tolyl-thiazol-4-yl)-ethoxy]-benzo[b]thiophen-7-yl}-propionic acid 0.089 g of the above prepared [rac]-2-ethoxy-3-{4-[2-(5-methyl-2-p-tolyl-thiazol-4-yl)-ethoxy]-benzo[b]thiophen-7-yl}-propionic acid ethyl ester (0.175 mmol) was dissolved in 1.1 ml of THF/EtOH=1/1, treated with 0.53 ml of 1N NaOH (3 eq.), and kept at ambient temperature for 1 h. The reaction mixture was then poured onto crashed ice/AcOEt/HCl dil., the organic layer washed with water, dried over magnesium sulfate, and evaporated to dryness. Crystallization from hexane/AcOEt afforded finally 0.074 g of the title compound as white crystals of mp. 126–27° C.
MS: 480.3 (M–H)⁻.

Example 73
[rac]-3-(4-{2-[2-(4-tert-Butyl-phenyl)-5-methyl-thiazol-4-yl]-ethoxy}-naphthalen-1-yl)-2-ethoxy-propionic acid Was prepared in analogy to example 72, but using in step a] 4-hydroxy-naphthalene-1-carbaldehyde instead of 4-hydroxy-benzo[b]thiophene-7-carbaldehyde and 2-[2-(4-tert-butyl-phenyl)-5-methyl-thiazol-4-yl]-ethanol (example 12 b]) instead of 2-(5-methyl-2-p-tolyl-thiazol-4-yl)-ethanol, respectively, as white solid of mp. 90–93° C.
MS: 516.4 (M–H)⁻.

Example 74
[rac]-3-(4-{2-[-2-(4-tert-Butyl-phenyl)-5-methyl-ethoxy]-benzo[b]thiophen-7-yl)-2-ethoxy-propionic acid Was prepared in analogy to example 72, but using in step a] 2-[2-(4-tert-butyl-phenyl)-5-methyl-thiazol-4-yl]-ethanol (example 12 b]) instead of 2-(5-methyl-2-p-tolyl-thiazol-4-yl)-ethanol, as white solid of mp. 152–54° C.
MS: 522.4 (M–H)⁻.

Example 75
[rac]-2-Ethoxy-3-(4-{2-[2-(4-isopropyl-phenyl)-5-methyl-thiazol-4-yl]-ethoxy}-benzo[b]thiophen-7-yl)-propionic acid Was prepared in analogy to example 72, but using in step a] 2-[2-(4-isopropyl-phenyl)-5-methyl-thiazol-4-yl]-ethanol (see example 41) instead of 2-(5-methyl-2-p-tolyl-thiazol-4-yl)-ethanol, and in step as white crystals of mp. 120–22" C.
MS: 508.3 (M–H)⁻.

Example 76
[rac]-2-Isopropoxy-3-(4-{2-[2-(4-isopropyl-phenyl)-5-methyl-thiazol-4-yl]-ethoxy}-naphthalen-1-yl)-propionic acid Was prepared in analogy to example 73, but using in step a] 2-[2-(4-isopropyl-phenyl)-5-methyl-thiazol-4-yl]-ethanol (see example 41) instead of 2-[2-(4-tert-butyl-phenyl)-5-methyl-thiazol-4-yl]-ethanol, and in step b] ethyl isopropoxyacetate instead of ethyl ethoxyacetate, as white foam.
MS: 516.4 (M–H)⁻.

Example 77
[rac]-2-Ethoxy-3-(4-{2-[2-(4-isopropyl-phenyl)-5-methyl-thiazol-4-yl]-ethoxy}-naphthalen-1-yl)-propionic acid Was prepared in analogy to example 76, but using in step b] ethyl ethoxyacetate instead of ethyl isopropoxyacetate, as white crystals of mp. 111–13° C.
MS: 504.2 (M+H)⁺.

Example 78
[rac]-2-Ethoxy-3-{4-[2-(5-methyl-2-p-tolyl-thiazol-4-yl)-ethoxy]-naphthalen-1-yl}-propionic acid Was prepared in analogy to example 72, but using in step a] 4-hydroxy-naphthalene-1-carbaldehyde instead of 4-hydroxy-benzo[b]thiophene-7-carbaldehyde, as white crystals of mp. 140–41° C.

MS: 474.3 (M−H)⁻.

Example 79
[rac]-2-Isopropoxy-3-[4-2-(5-methyl-2-phenyl-thiazol-4-yl)-ethoxy]-benzo[b]thiophen-7-yl}-propionic acid Was prepared in analogy to example 72, but using in step a] 2-(5-methyl-2-phenyl-thiazol-4-yl)-ethanol (see example 1) instead of 2-(5-methyl-2-p-tolyl-thiazol-4-yl)-ethanol, and in step b] ethyl isopropoxyacetate instead of ethyl ethoxyacetate, as off-white solid of mp. 73° C.

MS: 482.2 (M+H)⁺.

Example 80
[rac]-3-{4-[2-(5-Methyl-2-phenyl-thiazol-4-yl)-ethoxy]-naphthalen-1-yl}-2-propoxy-propionic acid Was prepared in analogy to example 76, but using in step a] 2-(5-methyl-2-phenyl-thiazol-4-yl)-ethanol (see example 1) instead of 2-[2-(4-isopropyl-phenyl)-5-methyl-thiazol-4-yl]-ethanol, and in step b] ethyl propoxyacetate instead of ethyl isopropoxyacetate, as white solid of mp. 95–99° C.

MS: 474.3 (M−H)⁻.

Example 81
[rac]-2-Methoxy-3-{4-[2-(5-methyl-2-p-tolyl-thiazol-4-yl)-ethoxy]-naphthalen-1-yl}-propionic acid Was prepared in analogy to example 78, but using in step b] ethyl methoxyacetate instead of ethyl ethoxyacetate, as white crystals of mp. 155–56° C.

MS: 462.2 (M+H)⁺.

Example 82
[rac]-3-{4-[2-(5-Methyl-2-p-tolyl-thiazol-4-yl)-ethoxy]-naphthalen-1-yl}-2-propoxy-propionic acid Was prepared in analogy to example 81, but using in step b] ethyl propoxyacetate instead of ethyl methoxyacetate, as white crystals of mp. 123–24° C.

MS: 488.3 (M−H)⁻.

Example 83
[rac]-3-(4-{2-[2-(3,5-Dimethoxy-phenyl)-5-methyl-thiazol-4-yl]-ethoxy}-benzo[b]thiophen-7-yl}-2-ethoxy-propionic acid Was prepared in analogy to example 72, but using in step a] 2-{2-[3,5-dimethoxy-phenyl)-5-methyl-thiazol-4-yl]-ethanol (see example 70 b]) instead of 2-(5-methyl-2-p-tolyl-thiazol-4-yl)-ethanol, as white crystals of mp. 148–50° C.

MS: 526.3 (M−H)⁻.

Example 84
[rac]-3-(4-{2-[2-(3,5-Dimethoxy-phenyl)-5-methyl-thiazol-4-yl]-ethoxy}-benzo[b]thiophen-7-yl)-2-methoxy-propionic acid Was prepared in analogy to example 83, but using in step b] ethyl methoxyacetate instead of ethyl ethoxyacetate, as white crystals of mp. 156–57° C.

MS: 512.3 (M−H)⁻.

Example 85
[rac]-3-(4-{2-[2-(3,5-Dimethoxy-phenyl)-5-methyl-thiazol-4-yl]-ethoxy}-benzo[b]thiophen-7-yl)-2-isopropoxy-propionic acid Was prepared in analogy to example 83, but using in step b] ethyl isopropoxyacetate instead of ethyl ethoxyacetate, as white crystals of mp. 150–52° C.

MS: 540.3 (M−H)⁻.

Example 86
[rac]-3-(4-{2-[2-(4-tert-Butyl-phenyl)-5-methyl-thiazol-4-yl]-ethoxy}-naphthalen-1-yl)-2-isopropoxy-propionic acid Was prepared in analogy to example 73, but using in step b] ethyl isopropoxyacetate instead of ethyl ethoxyacetate, as white solid of mp. 75–85° C.

MS: 530.3 (M−H)⁻.

Example 87
[rac]-3-(4-{2-[2-(4-tert-Butyl-phenyl)-5-methyl-thiazol-4-yl]-ethoxy}-benzo[b]thiophen-7-yl)-2-propoxy-propionic acid Was prepared in analogy to example 74, but using in step b] ethyl propoxyacetate instead of ethyl ethoxyacetate, as white solid of mp. 76° C.

MS: 536.3 (M−H)⁻.

Example 88
[rac]-3-(4-{2-[2-(3,5-Dimethoxy-phenyl)-5-methyl-thiazol-4-yl]-ethoxy}-naphthalen-1-yl)-2-ethoxy-propionic acid Was prepared in analogy to example 83, but using in step a] 4-hydroxy-naphthalene-1-carbaldehyde instead of 4-hydroxy-benzo[b]thiophene-7-carbaldehyde, as white crystals of mp. 133–35° C.

MS: 520.3 (M−H)⁻.

Example 89
[rac]-2-Ethoxy-3-{4-[2-(5-methyl-2-phenyl-thiazol-4-yl)-ethoxy]-naphthalen-1-yl}-propionic acid Was prepared in analogy to example 80, but using in step b] ethyl ethoxyacetate instead of ethyl propoxyacetate, as white solid of mp. 140–43° C.

MS: 460.3 (M−H)⁻.

Example 90
[rac]-2-Ethoxy-3-{4-[2-(5-methyl-2-phenyl-thiazol-4-yl)-ethoxy]-benzo[b]thiophen-7-yl}-propionic acid Was prepared in analogy to example 89, but using in step a] 4-hydroxy-benzo[b]thiophene-7-carbaldehyde instead of 4-hydroxy-naphthalene-1-carbaldehyde, as white solid of mp. 146–48° C.

MS: 466.2 (M−H)⁻.

Example 91
a] [rac]-2-Ethoxy-3-[2-methyl-4-(4-methyl-2-phenyl-thiazol-5-ylmethoxy)-phenyl]-propionic acid ethyl ester In analogy to the procedure described in example 10 c], [rac]-2-ethoxy-3-(4-hydroxy-2-methyl-phenyl)-propionic acid ethyl ester (example 10 b]) was reacted with (4-methyl-2-phenyl-thiazol-5-yl)-methanol [PCT Int. Appl. (2002), WO 02/80899 A1] in the presence of triphenylphosphine and diethyl azodicarboxylate to yield [rac]-2-ethoxy-3-[2-methyl-4-(4-methyl-2-phenyl-thiazol-5-ylmethoxy)-phenyl]-propionic acid ethyl ester as colorless oil.

MS: 440.2 (M+H)⁺, 396.3, 227.3.

b] [rac]-2-Ethoxy-3-[2-methyl-4-(4-methyl-2-phenyl-thiazol-5-ylmethoxy)-phenyl]-propionic acid In analogy to the procedure described in example 10 d], [rac]-2-ethoxy-3-[2-methyl-4-(4-methyl-2-phenyl-thiazol- 5-ylmethoxy)-phenyl]-propionic acid ethyl ester was treated with LiOH to obtain [rac]-2-ethoxy-3-[2-methyl-4-(4-methyl-2-phenyl-thiazol-5-ylmethoxy)-phenyl]-propionic acid as colorless oil.

MS: 434.4 (M+Na)$^+$, 412.2 (M+H)$^+$, 315.1, 228.3.

Example 92 a] [rac]-3-{4-[2-(2-Chloro-phenyl)-4-methyl-thiazol-5-ylmethoxy]-2-methyl-phenyl}-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with (2-(2-chloro-phenyl)-4-methyl-thiazol-5-yl]-methanol (prepared from 2-chloro-thiobenzamide and ethyl 2-chloro-acetoacetate in analogy to the procedures described in examples 33 a] and 33 b]) in the presence of triphenylphosphine and diethyl azodicarboxylate to yield [rac]-3-{4-[2-(2-chloro-phenyl)-4-methyl-thiazol-5-ylmethoxy]-2-methyl-phenyl}-2-ethoxy-propionic acid ethyl ester as colorless oil.

MS: 496.2 (M+Na)$^+$, 474.1 (M+H)$^+$.

b] [rac]-3-{4-[2-(2-Chloro-phenyl)-4-methyl-thiazol-5-ylmethoxy]-2-methyl-phenyl}-2-ethoxy-propionic acid In analogy to the procedure described in example 10 d], [rac]-3-{4-[2-(2-chloro-phenyl)-4-methyl-thiazol-5-ylmethoxy]-2-methyl-phenyl}-2-ethoxy-propionic acid ethyl ester was treated with LiOH to obtain [rac]-3-{4-[2-(2-chloro-phenyl)-4-methyl-thiazol-5-ylmethoxy]-2-methyl-phenyl}-2-ethoxy-propionic acid as colorless oil.

MS: 468.1 (M+Na)$^+$, 446.2 (M+H)$^+$, 371.3.

Example 93 a] 1-Bromo-2-fluoro-4-(phenylmethoxy)-benzene

In analogy to the procedure described in example 23 b], 1-fluoro-3-(phenylmethoxy)-benzene (for the preparation of 1-fluoro-3-(phenylmethoxy)-benzene see: A. A. Durrani, J. H. P. Tyrnan, J. Chem. Soc., Perkin Trans. 1 1979, 8, 2079–2087) was treated with N-bromosuccinimide in the presence of concentrated sulfuric acid to give 1-bromo-2-fluoro-4-(phenylmethoxy)-benzene as colorless oil.

b] 4-Benzyloxy-2-fluoro-benzaldehyde

In analogy to the procedure described in example 23 c], 1-bromo-2-fluoro-4-(phenylmethoxy)-benzene was treated with n-BuLi and N,N-dimethylformamide in dry tetrahydrofuran to yield 4-benzyloxy-2-fluoro-benzaldehyde as off-white crystals.

MS: 230.1 (M)$^+$.

c] (S)-4-Benzyl-3-[(2S,3R)-3-(4-benzyloxy-2-fluoro-phenyl)-2-ethoxy-3-hydroxy-propionyl]-oxazolidin-2-one In analogy to the procedure described in example 17 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Canteilo, D. S. Eggleston, R. C. Haltiwanger, R. M. Hindley, A. Ramaswamy, N. C. Stevens, Tetrahedron: Asymmetry 1999, 10, 1353–1367) was reacted with 4-benzyloxy-2-fluoro-benzaldehyde in the presence of triethylamine and di-n-butylboron triflate to give (S)-4-benzyl-3-[(2S,3R)-3-(4-benzyloxy-2-fluoro-phenyl)-2-ethoxy-3-hydroxy-propionyl]-oxazolidin-2-one as colorless foam. According to $^1$H-NMR spectroscopy, one of the four isomers is strongly predominating. The configuration was tentatively assigned as 2S,3R according to D. Haigh et al., Tetrahedron: Asymmetry 1999, 10, 1353–1367.

MS: 516.2 (M+Na)$^+$, 476.2, 435.3, 419.3, 387.1, 330.2, 203.1.

d] (2S,3R)-3-(4-Benzyloxy-2-fluoro-phenyl)-2-ethoxy-3-hydroxy-propionic acid methyl ester In analogy to the procedure described in example 17 b], (S)-4-benzyl-3-[(2S,3R)-3-(4-benzyloxy-2-fluoro-phenyl)-2-ethoxy-3-hydroxy-propionyl]-oxazolidin-2-one was treated with sodium methoxide in methanol to give (2S,3R)-3-(4-benzyloxy-2-fluoro-phenyl)-2-ethoxy-3-hydroxy-propionic acid methyl ester as colorless liquid. According to $^1$H-NMR spectroscopy, one single diastereomer was obtained.

MS: 371.3 (M+Na)$^+$, 331.3, 303.2, 279.2, 242.2.

e] (2S)-3-(4-Benzyloxy-2-fluoro-phenyl)-2-ethoxy-propionic acid methyl ester

In analogy to the procedure described in example 17 c], (2S,3R)-3-(4-benzyloxy-2-fluoro-phenyl)-2-ethoxy-3-hydroxy-propionic acid methyl ester was treated with triethylsilane in trifluoroacetic acid to yield (2S)-3-(4-benzyloxy-2-fluoro-phenyl)-2-ethoxy-propionic acid methyl ester as colorless liquid.

MS: 355.2 (M+Na)$^+$, 350.3 (M+NH$_4$)$^+$, 333.3 (M+H)$^+$, 245.3.

f] (2S)-2-Ethoxy-3-(2-fluoro-4-hydroxy-phenyl)-propionic acid methyl ester

In analogy to the procedure described in example 17 d], (2S)-3-(4-benzyloxy-2-fluoro-phenyl)-2-ethoxy-propionic acid methyl ester was hydrogenated over 10% palladium on charcoal to give (2S)-2-ethoxy-3-(2-fluoro-4-hydroxy-phenyl)-propionic acid methyl ester as colorless liquid.

MS: 265.2 (M+Na)$^+$, 260.2 (M+NH$_4$)$^+$, 243.3 (M+H)$^+$, 197.1, 155.3.

g] (S)-3-{4-[2-(4-Chloro-phenyl)-thiazol-4-ylmethoxy-2-fluoro-phenyl}-2-ethoxy-propionic acid methyl ester In analogy to the procedure described in example 14 b], (2S)-2-ethoxy-3-(2-fluoro-4-hydroxy-phenyl)-propionic acid methyl ester was reacted with 4-chloromethyl-2-(4-chloro-phenyl)-thiazole (example 14 a]) in the presence of cesium carbonate and potassium iodide to yield (S)-3-{4-[2-(4-chloro-phenyl)-thiazol-4-ylmethoxy]-2-fluoro-phenyl}-2-ethoxy-propionic acid methyl ester as light yellow oil.

MS: 472.0 (M+Na)$^+$, 450.2 (M+H)$^+$.

h] (S)-3-{4-[2-(4-Chloro-phenyl)-thiazol-4-ylmethoxy]-2-fluoro-phenyl}-2-ethoxy-propionic acid In analogy to the procedure described in example 10 d], (S)-3-{4-[2-(4-chloro-phenyl)-thiazol-4-ylmethoxy]-2-fluoro-phenyl}-2-ethoxy-propionic acid methyl ester was treated with LiOH to obtain (S)-3-{4-[2-(4-chloro-phenyl)-thiazol-4-ylmethoxy]-2-fluoro-phenyl}-2-ethoxy-propionic acid as light yellow solid.

MS: 436.1 (M+H)$^+$, 390.9, 304.2, 261.7, 241.3.

Example 94 a] 4-Benzyloxy-benzofuran

To a suspension of potassium carbonate (2.68 g, 19.4 mmol) in N,N-dimethylformamide (8 ml) was added a solution of 4-hydroxy-benzofuran (2.6 g, 19.4 mmol) in N,N-dimethylformamide (8 ml) at 2° C. under an argon atmosphere (for the preparation of 4-hydroxy-benzofuran see: G. Kneen, P. J. Maddocks, Syn. Commun. 1986, 16, 1635–1640). After stirring for 50 min at 2° C., benzyl bromide (3.3 ml, 19.4 mmol) was added over a period of 15 min at 2° C. The suspension was stirred for additional 30 min at 2° C. and for 1.5 h at ambient temperature. After adding ice water (20 ml), the solution was extracted two times with diethyl ether. The combined extracts were washed three times with brine and dried over sodium sulfate. Evaporation of the solvent gave a yellow oil which was purified by column chromatography (silica gel, hexane) to give 4.3 g (19.2 mmol, 99%) of the title compound as colorless oil.

MS: 224.1 (M)$^+$.

b] 4-Benzyloxy-benzofuran-7-carbaldehyde

Dry N,N-dimethylformamide (12.1 g, 166 mmol) was added dropwise with stirring and cooling under an argon atmosphere to phosphorous oxychloride (11.4 g, 75 mmol) at such a rate that the temperature did not exceed 10° C. After 30 min at 10° C., a solution of 4-benzyloxy-benzofuran (9.3 g, 41 mmol) in N,N-dimethylformamide (9 ml) was added dropwise within 30 min. The reaction mixture was stirred 30 min at ambient temperature and then continuously heated to 100° C. After 10 min at 100° C. the mixture was heated at 85° C. for 3 h, cooled to 10° C., neutralized with 25% aqueous sodium acetate, with cooling, and extracted with diethyl ether. The extract was washed with saturated aqueous sodium bicarbonate and water and dried over sodium sulfate. Removal of the solvent under reduced pressure gave a brown oil which was purified by column chromatography (silica gel, hexane/AcOEt=19/1) to give 1.8 g (7 mmol, 17%) of the title compound as yellow oil.

MS: 252.1 (M)$^+$.

c] 3-(4-Benzyloxy-benzofuran-7-yl)-2Z-ethoxy-acrylic acid ethyl ester

A suspension of (1,2-diethoxy-2-oxoethyl)triphenyl phosphonium chloride (2.04 g, 4.8 mmol) and DBU (0.8 g, 5.2 mmol) in THF (40 ml) was stirred for 10 min at ambient temperature under an argon atmosphere [for the preparation of (1,2-diethoxy-2-oxoethyl)triphenyl phosphonium chloride see: K. K. Bach, H. R. El-Seedi, H. M. Jensen, H. B. Nielsen, I. Thomson, K. B. G. Torssell, *Tetrahedron* 1994, 50, 7543–7556]. 4-Benzyloxy-benzofuran-7-carbaldehyde (0.8 g, 3.2 mmol) was added and the mixture was heated under reflux for 12 h. The solvent was concentrated at reduced pressure, the residue taken up with ethyl acetate, washed with saturated aqueous NH$_4$Cl solution and two times with brine. The organic layer was dried over sodium sulfate, the solvent removed under reduced pressure and the residue purified by column chromatography (silica gel, hexane/AcOEt=9/1) to give 0.8 g (2.2 mmol, 69%) of the title compound as colorless oil.

MS: 366.1 (M)$^+$, 275.1, 173.0.

d] [rac]-2-Ethoxy-3-(4-hydroxy-2,3-dihydro-benzofuran-7-yl)-propionic acid ethyl ester A solution of 3-(4-benzyloxy-benzofuran-7-yl)-2Z-ethoxy-acrylic acid ethyl ester (420 mg, 1.15 mmol) in methanol (17 ml) was hydrogenated over 10% palladium on charcoal (100 mg) at ambient temperature for 20 h. The catalyst was filtered off, the solvent evaporated under reduced pressure and the residue chromatographed (silica gel, hexane/AcOEt=4/1) to give 240 mg (0.86 mmol, 75%) of the title compound as colorless liquid.

MS: 279.1 (M–H)$^-$, 265.2, 141.0.

e] [rac]-3-{7-[2-(4-Chloro-phenyl)-thiazol-4-ylmethoxy]-2,3-dihydro-benzofuran-4-yl}-2-ethoxy-propionic acid ethyl ester In analogy to the procedure described in example 14 b], [rac]-2-ethoxy-3-(4-hydroxy-2,3-dihydro-benzofuran-7-yl)-propionic acid ethyl ester was reacted with 4-chloromethyl-2-(4-chloro-phenyl)-thiazole (example 14 a]) in the presence of cesium carbonate and potassium iodide to yield [rac]-3-{7-[2-(4-chloro-phenyl)-thiazol-4-ylmethoxy]-2,3-dihydro-benzofuran-4-yl}-2-ethoxy-propionic acid ethyl ester as colorless oil.

MS: 490,2 (M+H)$^+$, 488.3 (M+H)$^+$, 442.2, 414.2, 249.2.

f] [rac]-3-{7-[2-(4-Chloro-phenyl)-thiazol-4-ylmethoxy]-2,3-dihydro-benzofuran-4-yl}-2-ethoxy-propionic acid In analogy to the procedure described in example 10 d], [rac]-3-{7-[2-(4-chloro-phenyl)-thiazol-4-ylmethoxy]-2,3-dihydro-benzofuran-4-yl}-2-ethoxy-propionic acid ethyl ester was treated with LiOH to obtain [rac]-3-{7-[2-(4-chloro-phenyl)-thiazol-4-ylmethoxy]-2,3-dihydro-benzofuran-4-yl}-2-ethoxy-propionic acid as colorless oil.

MS: 458.3 (M–H)$^-$, 340.2, 283.2, 255.4.

Example 95 a] [rac]-3-(4-Benzyloxy-benzofuran-7-yl)-2-ethoxy-propionic acid methyl ester

Magnesium turnings (0.5 g, 20.6 mmol) were added to a stirred solution of 3-(4-benzyloxy-benzofuran-7-yl)-2Z-ethoxy-acrylic acid ethyl ester (0.8 g, 2.18 mmol; example 94 c]) in methanol (26 ml) and THF (13 ml) at ambient temperature. The suspension was warmed to 40° C. until evolution of hydrogen commenced. Then, the heating bath was replaced by a water bath, additional magnesium turnings (1 g, 41.2 mmol) were added and stirring of the reaction mixture was continued for 12 h. The suspension was cooled to 0° C., then 25% aqueous hydrochloric acid was added till all the solid had dissolved. The mixture was extracted twice with ethyl acetate and the combined ethyl acetate solutions were washed three times with water and dried over sodium sulfate. The solvent was evaporated to afford the title compound (0.77 g, 2.16 mmol, 99%) which was used in the next step without further purification.

MS: 354.2 (M)$^+$, 237.2.

b] [rac]-2-Ethoxy-3-(4-hydroxy-benzofuran-7-yl)-propionic acid methyl ester

Dimethyl sulfide (4.4 ml, 60 mmol) and boron trifluoride diethyl etherate (46% purity, 3.3 ml, 12 mmol) were added to an ice cold solution of [rac]-3-(4-benzyloxy-benzofuran-7-yl)-2-ethoxy-propionic acid methyl ester (0.85 g, 2.4 mmol) in dichloromethane (25 ml) under an argon atmosphere. The mixture was stirred for 6 h at ambient temperature, poured into ice water and extracted three times with dichloromethane. The combined extract was washed with brine and dried over sodium sulfate. Removal of the solvent under reduced pressure gave a brown oil which was purified by column chromatography (silica gel, hexane/AcOEt=4/1) to give 0.45 g (1.7 mmol, 71%) of the title compound as light yellow oil.

MS: 263.0 (M–H)$^-$.

c] [rac]-3-{7-[2-(4-Chloro-phenyl)-thiazol-4-ylmethoxy]-benzofuran-4-yl}-2-ethoxy-propionic acid methyl ester In analogy to the procedure described in example 14 b], [rac]-2-ethoxy-3-(4-hydroxy-benzofuran-7-yl)-propionic acid methyl ester was reacted with 4-chloromethyl-2-(4-chloro-phenyl)-thiazole (example 14 a]) in the presence of cesium carbonate and potassium iodide to yield [rac]-3-{7-[2-(4-chloro-phenyl)-thiazol-4-ylmethoxy]-benzofuran-4-yl}-2-ethoxy-propionic acid methyl ester as colorless oil.

MS: 489.3 (M+NH$_4$)$^+$, 472.2 (M+H)$^+$, 426.3, 325.3, 225.3.

d] [rac]-3-{7-[2-(4-Chloro-phenyl)-thiazol-4-ylmethoxy]-benzofuran-4-yl}-2-ethoxy-propionic acid In analogy to the procedure described in example 10 d], [rac]-3-{7-[2-(4-chloro-phenyl)-thiazol-4-ylmethoxy]-benzofuran-4-yl}-2-ethoxy-propionic acid methyl ester was treated with LiOH to obtain [rac]-3-{7-[2-(4-chloro-phenyl)-thiazol-4-ylmethoxy]-benzofuran-4-yl}-2-ethoxy-propionic acid as colorless solid.

MS: 456.2 (M–H)$^-$, 410.2, 340.1.

Example 96 a] [rac]-2-Ethoxy-3-[2-methyl-4-(5-methyl-2-phenyl-thiazol-4-ylmethoxy)-phenyl]-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 4-bromomethyl-5-methyl-2-phenyl-thiazole [PCT Int. Appl. (2001), WO 01/9805 A1] in the presence of cesium carbonate and potassium iodide to yield [rac]-2-ethoxy-3-[2-methyl-4-(5-methyl-2-phenyl-thiazol-4-ylmethoxy)-phenyl]-propionic acid ethyl ester as colorless liquid.

MS: 462.3 (M+Na)$^+$, 440.4 (M+H)$^+$, 394.3, 229.2.

b] [rac]-2-Ethoxy-3-[2-methyl-4-(5-methyl-2-phenyl-thiazol-4-ylmethoxy)-phenyl]-propionic acid In analogy to the procedure described in example 10 d], [rac]-2-ethoxy-3-[2-methyl-4-(5-methyl-2-phenyl-thiazol-4-ylmethoxy)-phenyl]-propionic acid ethyl ester was treated with LiOH to obtain [rac]-2-ethoxy-3-[2-methyl-4-(5-methyl-2-phenyl-thiazol-4-ylmethoxy)-phenyl]-propionic acid as colorless liquid.

MS: 434.2 (M+Na)$^+$, 412.3 (M+H)$^+$, 313.2, 229.2.

Example 97 a] [rac]-3-{4-[2-(4-Chloro-phenyl)-5-methyl-thiazol-4-ylmethoxy]-2-methyl-phenyl}-2-ethoxy-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 4-bromomethyl-2-(4-chloro-phenyl)-5-methyl-thiazole (JP 62178590 A2) in the presence of cesium carbonate and potassium iodide to yield [rac]-3-{4-[2-(4-chloro-phenyl)-5-methyl-thiazol-4-ylmethoxy]-2-methyl-phenyl}-2-ethoxy-propionic acid ethyl ester as light yellow crystals.

MS: 496.1 (M+Na)$^+$, 476.3 (M+H)$^+$, 474.2 (M+H)$^+$, 263.2.

b] [rac]-3-{4-[2-(4-Chloro-phenyl)-5-methyl-thiazol-4-ylmethoxy]-2-methyl-phenyl}-2-ethoxy-propionic acid In analogy to the procedure described in example 10 d], [rac]-3-{4-[2-(4-chloro-phenyl)-5-methyl-thiazol-4-ylmethoxy]-2-methyl-phenyl}-2-ethoxy-propionic acid ethyl ester was treated with LiOH to obtain [rac]-3-{4-[2-(4-chloro-phenyl)-5-methyl-thiazol-4-ylmethoxy]-2-methyl-phenyl}-2-ethoxy-propionic acid as colorless solid.

MS: 468.3 (M+Na)$^+$, 446.2 (M+H)$^+$.

Example 98 a] [rac]-2-Ethoxy-3-(4-{2-[2-(4-methoxy-phenyl)-5-methyl-thiazol-4-yl]-ethoxy}-2-methyl-phenyl)-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(4-methoxy-phenyl)-5-methyl-thiazol-4-yl]-ethanol (prepared from [rac]-4-bromo-3-oxo-pentanoic acid methyl ester [PCT Int. Appl. (2001), WO 01/79202] and 4-methoxy-thiobenzamide in analogy to the procedures described in examples 12 a] and 12 b]) in the presence of triphenylphosphine and di-tert-butyl azodicarboxylate to yield [rac]-2-ethoxy-3-(4-{2-[2-(4-methoxy-phenyl)-5-methyl-thiazol-4-yl]-ethoxy}-2-methyl-phenyl)-propionic acid ethyl ester as yellow crystals.

b] [rac]-2-Ethoxy-3-(4-{2-[2-(4-methoxy-phenyl)-5-methyl-thiazol-4-yl]-ethoxy}-2-methyl-phenyl)-propionic acid In analogy to the procedure described in example 10 d], [rac]-2-ethoxy-3-(4-{2-[2-(4-methoxy-phenyl)-5-methyl-thiazol-4-yl]-ethoxy}-2-methyl-phenyl)-propionic acid ethyl ester was treated with LiOH to obtain [rac]-2-ethoxy-3-(4-{2-[2-(4-methoxy-phenyl)-5-methyl-thiazol-4-yl]-ethoxy}-2-methyl-phenyl)-propionic acid as colorless oil.

MS: 478.5 (M+Na)$^+$, 456.5 (M+H)$^+$.

Example 99 a] [rac]-2-Ethoxy-3-(4-{2-[2-(4-methoxy-phenyl)-thiazol-4-yl]-ethoxy}-2-methyl-phenyl)-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(4-methoxy-phenyl)-thiazol-4-yl]-ethanol (prepared from 4-methoxy-thiobenzamide and 1,3-dichloroacetone in analogy to the procedure described in example 4 a] to yield 4-chloromethyl-2-(4-methoxy-phenyl)-thiazole, followed by side chain elongation in analogy to the sequence described in example 13 a] to 13 d]) in the presence of triphenylphosphine and di-tert-butyl azodicarboxylate to yield [rac]-2-ethoxy-3-(4-{2-[2-(4-methoxy-phenyl)-thiazol-4-yl]-ethoxy}-2-methyl-phenyl)-propionic acid ethyl ester as light yellow solid.

MS: 492.3 (M+Na)$^+$, 470.2 (M+H)$^+$, 424.3, 396.3.

b] [rac]-2-Ethoxy-3-(4-{2-[2-(4-methoxy-phenyl)-thiazol-4-yl]-ethoxy}-2-methyl-phenyl)-propionic acid In analogy to the procedure described in example 10 d], [rac]-2-ethoxy-3-(4-{2-[2-(4-methoxy-phenyl)-thiazol-4-yl]-ethoxy}-2-methyl-phenyl)-propionic acid ethyl ester was treated with LiOH to obtain [rac]-2-ethoxy-3-(4-{2-[2-(4-methoxy-phenyl)-thiazol-4-yl]-ethoxy}-2-methyl-phenyl)-propionic acid as colorless liquid.

MS: 440.3 (M−H)$^-$, 394.1.

Example 100 a] [rac]-2-Ethoxy-3-{4-[2-(3-methoxy-phenyl)-4-methyl-thiazol-5-ylmethoxy]-2-methyl-phenyl}-propionic acid ethyl ester In analogy to the procedure described in example 10 c], [rac]-2-ethoxy-3-(4-hydroxy-2-methyl-phenyl)-propionic acid ethyl ester (example 10 b]) was reacted with [2-(3-methoxy-phenyl)-4-methyl-thiazol-5-yl]-methanol (prepared from 3-methoxy-thiobenzamide [PCT Int. Appl. (2002), WO 0100433 A1] and ethyl 2-chloro-acetoacetate in analogy to the procedures described in example 33 a] and 33 b]) in the presence of triphenylphosphine and di-tert-butyl azodicarboxylate to yield [rac]-2-ethoxy-3-{4-[2-(3-methoxy-phenyl)-4-methyl-thiazol-5-ylmethoxy]-2-methyl-phenyl}-propionic acid ethyl ester as light yellow solid.

MS: 492.3 (M+Na)$^+$, 470.2 (M+H)$^+$, 426.4, 339.2, 255.2.

b] [rac]-2-Ethoxy-3-{4-[2-(3-methoxy-phenyl)-4-methyl-thiazol-5-ylmethoxy]-2-methyl-phenyl}-propionic acid In analogy to the procedure described in example 10 d], [rac]-2-ethoxy-3-{4-[2-(3-methoxy-phenyl)-4-methyl-thiazol-5-ylmethoxy]-2-methyl-phenyl}-propionic acid ethyl ester was treated with LiOH to obtain [rac]-2-ethoxy-3-{4-[2-(3-methoxy-phenyl)-4-methyl-thiazol-5-ylmethoxy]-2-methyl-phenyl}-propionic acid as colorless foam.

MS: 440.3 (M−H)$^-$, 394.1, 255.3.

Example 101 a] [rac]-3-{4-[2-(2,4-Dichloro-phenyl)-4-methyl-thiazol-5-ylmethoxy]-2-methyl-phenyl}-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-(2,4-dichloro-phenyl)-5-methoxymethyl-4-methyl-thiazole (prepared from 2,4-dichloro-thiobenzamide and ethyl 2-chloro-acetoacetate in analogy to the procedures described in examples 33 a] and 33 b]) in the presence of tributylphosphine and N,N,N',N'-tetramethyl azodicarboxamide to yield [rac]-3-{4-[2-(2,4-dichloro-phenyl)-4-methyl-thiazol-5-ylmethoxy]-2-methyl-phenyl}-2-ethoxy-propionic acid ethyl ester as colorless liquid.

MS: 510.4 (M+H)$^+$, 509.3 (M+H)$^+$, 508.3 (M+H)$^+$.

b] [rac]-3-{4-[2-(2,4-Dichloro-phenyl)-4-methyl-thiazol-5-ylmethoxy]-2-methyl-phenyl}-2-ethoxy-propionic acid In analogy to the procedure described in example 10 d], [rac]-3-{4-[2-(2,4-dichloro-phenyl)-4-methyl-thiazol-5-ylmethoxy]-2-methyl-phenyl}-2-ethoxy-propionic acid ethyl ester was treated with LiOH to obtain [rac]-3-{4-[2-(2,4-dichloro-phenyl)-4-methyl-thiazol-5-ylmethoxy]-2-methyl-phenyl}-2-ethoxy-propionic acid as colorless solid.

MS: 478.1 (M−H)$^-$, 432.2.

Example 102 a] [rac]-3-(4-{3-[2-(4-tert-Butyl-phenyl)-5-methyl-thiazol-4-yl]-propoxy}-2-methyl-phenyl)-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 3-[2-(4-tert-butyl-phenyl)-5-methyl-thiazol-4-yl]-propan-1-ol (prepared from methanesulfonic acid 2-[2-(4-tert-butyl-phenyl)-5-methyl-thiazol-4-yl]-ethyl ester [obtained from 2-[2-(4-tert-butyl-phenyl)-5-methyl-thiazol-4-yl]-ethanol (example 12 b]) and methanesulfonyl chloride in pyridine at 0° C.] according to the sequence described in examples 13 a] to d]) in the presence of tributylphosphine and N,N,N',N'-tetramethyl azodicarboxamide to yield [rac]-3-(4-{3-[2-(4-tert-butyl-phenyl)-5-methyl-thiazol-4-yl]-propoxy}-2-methyl-phenyl)-2-ethoxy-propionic acid ethyl ester as colorless liquid.

MS: 546.4 (M+Na)$^+$, 524.4 (M+H)$^+$, 425.5.

b] [rac]-3-(4-{3-[2-(4-tert-Butyl-phenyl)-5-methyl-thiazol-4-yl]-propoxy}-2-methyl-phenyl)-2-ethoxy-propionic acid In analogy to the procedure described in example 10 d], [rac]-3-(4-{3-[2-(4-tert-butyl-phenyl)-5-methyl-thiazol-4-yl]-propoxy}-2-methyl-phenyl)-2-ethoxy-propionic acid ethyl ester was treated with LiOH to obtain [rac]-3-(4-{3-[2-(4-tert-butyl-phenyl)-5-methyl-thiazol-4-yl]-propoxy}-2-methyl-phenyl)-2-ethoxy-propionic acid as colorless liquid.

MS: 494.4 (M−H)$^-$, 450.2.

Example 103 a] 4-Benzyloxy-2,6-dimethyl-benzaldehyde

In analogy to the procedure described in example 23 a], 4-hydroxy-2,6-dimethyl-benzaldehyde was reacted with benzyl bromide in the presence of potassium carbonate to yield 4-benzyloxy-2,6-dimethyl-benzaldehyde as orange liquid.

MS: 241.2 (M+H)$^+$, 181.0.

b] (S)-4-Benzyl-3-[(2S,3R)-3-(4-benzyloxy-2,6-dimethyl-phenyl)-2-ethoxy-3-hydroxy-propionyl]-oxazolidin-2-one In analogy to the procedure described in example 17 a], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353–1367) was reacted with 4-benzyloxy-2,6-dimethyl-benzaldehyde in the presence of triethylamine and di-n-butylboron triflate to give (S)-4-benzyl-3-[(2S,3R)-3-(4-benzyloxy-2,6-dimethyl-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 526.3 (M+Na)$^+$, 486.3, 358.2, 309.1, 281.2, 237.2.

c] (2S,3R)-3-(4-Benzyloxy-2,6-dimethyl-phenyl)-2-ethoxy-3-hydroxy-propionic acid methyl ester In analogy to the procedure described in example 17 b], (S)-4-benzyl-3-[(2S,3R)-3-(4-benzyloxy-2,6-dimethyl-phenyl)-2-ethoxy-3-hydroxy-propionyl]-oxazolidin-2-one was treated with sodium methoxide in methanol to give (2S,3R)-3-(4-benzyloxy-2,6-dimethyl-phenyl)-2-ethoxy-3-hydroxy-propionic acid methyl ester as colorless liquid. According to $^1$H-NMR spectroscopy, one single diastereomer was obtained.

MS: 381.2 (M+Na)$^+$, 376.3 (M+NH$_4$)$^+$, 341.2, 313.2, 213.3.

d] (2S)-3-(4-Benzyloxy-2,6-dimethyl-phenyl)-2-ethoxy-propionic acid methyl ester In analogy to the procedure described in example 17 c], (2S,3R)-3-(4-benzyloxy-2,6-dimethyl-phenyl)-2-ethoxy-3-hydroxy-propionic acid methyl ester was treated with triethylsilane in trifluoroacetic acid to yield (2S)-3-(4-benzyloxy-2,6-dimethyl-phenyl)-2-ethoxy-propionic acid methyl ester as colorless liquid.

MS: 360.3 (M+NH$_4$)$^+$, 284.1, 201.1.

e] (2S)-2-Ethoxy-3-(4-hydroxy-2,6-dimethyl-phenyl)-propionic acid methyl ester

In analogy to the procedure described in example 17 d], (2S)-3-(4-benzyloxy-2,6-dimethyl-phenyl)-2-ethoxy-propionic acid methyl ester was hydrogenated over 10% palladium on charcoal to give (2S)-2-ethoxy-3-(4-hydroxy-2,6-dimethyl-phenyl)-propionic acid methyl ester as colorless liquid.

MS: 275.2 (M+Na)$^+$, 270.3 (M+NH$_4$)$^+$, 253.3 (M+H)$^+$.

f] (S)-3-{4-[2-(4-Chloro-phenyl)-thiazol-4-ylmethoxy]-2,6-dimethyl-phenyl}-2-ethoxy-propionic acid methyl ester In analogy to the procedure described in example 14 b], (2S)-2-ethoxy-3-(4-hydroxy-2,6-dimethyl-phenyl)-propionic acid methyl ester was reacted with 4-chloromethyl-2-(4-chloro-phenyl)-thiazole (example 14 a]) in the presence of cesium carbonate and potassium iodide to yield (S)-3-{4-[2-(4-chloro-phenyl)-thiazol-4-ylmethoxy]-2,6-dimethyl-phenyl}-2-ethoxy-propionic acid methyl ester as off-white solid.

g] (S)-3-{4-[2-(4-Chloro-phenyl)-thiazol-4-ylmethoxy]-2,6-dimethyl-phenyl}-2-ethoxy-propionic acid In analogy to the procedure described in example 10 d], (S)-3-{4-[2-(4-chloro-phenyl)-thiazol-4-ylmethoxy]-2,6-dimethyl-phenyl}-2-ethoxy-propionic acid methyl ester was treated with LiOH to obtain (S)-3-{4-[2-(4-chloro-phenyl)-thiazol-4-ylmethoxy]-2,6-dimethyl-phenyl}-2-ethoxy-propionic acid as light yellow solid.

MS: 444.3 (M−H)$^-$, 381.0, 309.2.

Example 104 a] 5-Chloromethyl-2-(4-chloro-phenyl)-4-methyl-thiazole

To a suspension of [2-(4-chloro-phenyl)-4-methyl-thiazol-5-yl]-methanol (643 mg, 2.7 mmol; obtained from 4-chloro-thiobenzamide and ethyl 2-chloro-acetoacetate in analogy to the procedures described in examples 33 a] and 33 b]) in chloroform (4 ml) was added thionyl chloride (390 µl, 5.4 mmol) at −10° C. under an argon atmosphere. The reaction mixture was stirred for 30 min, saturated aqueous sodium bicarbonate solution/ice water 1/1 were added and the layers were separated. The aqueous layer was extracted two times with dichloromethane. The combined organic layers were washed with ice water/brine 1/1, dried over sodium sulfate and the solvent was evaporated in vacuo to give the title compound (595 mg, 2.3 mmol, 86%) as colorless solid.

MS: 262.3 (M)$^+$, 240.2.

b] [2-(4-Chloro-phenyl)-4-methyl-thiazol-5-yl]-acetonitrile

Tetrabutylammonium cyanide (804 mg, 3 mmol) was added to a solution of 5-chloromethyl-2-(4-chloro-phenyl)-4-methyl-thiazole (595 mg, 2.3 mmol) in acetonitrile (25 ml). The solution was stirred at ambient temperature for 16 h, saturated aqueous sodium bicarbonate solution/ice water 1/1 and diethyl ether were added and the layers were separated. The aqueous layer was extracted one more time with diethyl ether, the combined organic layers were washed with ice water/brine 1/1, dried over sodium sulfate and the solvent was evaporated in vacuo to give orange crystals which were purified by column chromatography (silica gel, cyclohexane/AcOEt) to yield 370 mg (1.5 mmol, 65%) of the title compound as light yellow solid.

MS: 249.4 (M+H)$^+$, 224.5, 217.5.

c] 2-[2-(4-Chloro-phenyl)-4-methyl-thiazol-5-yl]-ethanol

A solution of [2-(4-chloro-phenyl)-4-methyl-thiazol-5-yl]-acetic acid (300 mg, 1.1 mmol; prepared from [2-(4-chloro-phenyl)-4-methyl-thiazol-5-yl]-acetonitrile in analogy to the procedure described in example 13 b]) in tetrahydrofuran (4.5 ml) was treated at 0° C. with borane-tetrahydrofuran complex (1 M solution in tetrahydrofuran; 2.8 ml, 2.8 mmol). The cooling bath was removed and the reaction mixture stirred at ambient temperature for 16 h. Careful quenching with MeOH and ice water, twofold extraction with AcOEt, washing with ice water/brine 1/1, drying over magnesium sulfate, and evaporation of the solvent left a crude product which was refluxed for 30 min in MeOH to liberate quantitatively the free alcohol. The solvent was evaporated in vacuo and the residue was purified by column chromatography (silica gel, heptane/AcOEt) to yield 240 mg (0.95 mmol, 84%) of the title compound as colorless solid.

MS: 254.3 (M+H)$^+$, 228.3.

d] [rac]-3-(4-{2-[2-(4-Chloro-phenyl)-4-methyl-thiazol-5-yl]-ethoxy}-2-methyl-phenyl)-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(4-chloro-phenyl)-4-methyl-thiazol-5-yl]-ethanol in the presence of tributylphosphine and N,N,N',N'-tetramethyl azodicarboxamide to yield [rac]-3-(4-{2-[2-(4-chloro-phenyl)-4-methyl-thiazol-5-yl]-ethoxy}-2-methyl-phenyl)-2-ethoxy-propionic acid ethyl ester as colorless liquid.

MS: 490.2 (M+H)$^+$, 488.3 (M+H)$^+$, 444.2, 356.3.

e] [rac]-3-(4-{2-[2-(4-Chloro-phenyl)-4-methyl-thiazol-5-yl]-ethoxy}-2-methyl-phenyl)-2-ethoxy-propionic acid In analogy to the procedure described in example 10 d], [rac]-3-(4-{2-[2-(4-chloro-phenyl)-4-methyl-thiazol-5-yl]-ethoxy}-2-methyl-phenyl)-2-ethoxy-propionic acid ethyl ester was treated with LiOH to obtain [rac]-3-(4-{2-[2-(4-chloro-phenyl)-4-methyl-thiazol-5-yl]-ethoxy}-2-methyl-phenyl)-2-ethoxy-propionic acid as light yellow solid.

MS: 458.3 (M−H)$^−$, 412.2.

Example 105 a] [rac]-2-Ethoxy-3-{2-methyl-4-[4-methyl-2-(4-trifluoromethyl-phenyl)-thiazol-5-ylmethoxy]-phenyl}-propionic acid ethyl ester In analogy to the procedure described in example 14 b], [rac]-2-ethoxy-3-(4-hydroxy-2-methyl-phenyl)-propionic acid ethyl ester (example 10 b]) was reacted with 5-chloromethyl-4-methyl-2-(4-trifluoromethyl-phenyl)-thiazole [PCT Int. Appl. (2002), WO 0292590 A1] in the presence of cesium carbonate and potassium iodide to yield [rac]-2-ethoxy-3-{2-methyl-4-[4-methyl-2-(4-trifluoromethyl-phenyl)-thiazol-5-ylmethoxy]-phenyl}-propionic acid ethyl ester as colorless liquid.

MS: 530.3 (M+Na)$^+$, 508.3 (M+H)$^+$, 256.1.

b] [rac]-2-Ethoxy-3-{2-methyl-4-[4-methyl-2-(4-trifluoromethyl-phenyl)-thiazol-5-ylmethoxy]-phenyl}-propionic acid In analogy to the procedure described in example 10 d], [rac]-2-ethoxy-3-{2-methyl-4-[4-methyl-2-(4-trifluoromethyl-phenyl)-thiazol-5-ylmethoxy]-phenyl}-propionic acid ethyl ester was treated with LiOH to obtain [rac]-2-ethoxy-3-{2-methyl-4-[4-methyl-2-(4-trifluoromethyl-phenyl)-thiazol-5-ylmethoxy]-phenyl}-propionic acid as light yellow solid.

MS: 478.2 (M−H)$^−$, 434.3.

Example 106 a] [rac]-3-(4-{2-[2-(2-Chloro-phenyl)-4-methyl-thiazol-5-yl]-ethoxy}-2-methyl-phenyl)-2-ethoxy-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(2-chloro-phenyl)-4-methyl-thiazol-5-yl]-ethanol (prepared from [2-(2-chloro-phenyl)-4-methyl-thiazol-5-yl]-methanol (obtained from 2-chloro-thiobenzamide and ethyl 2-chloro-acetoacetate in analogy to the procedures described in examples 33 a] and 33 b]) according to the sequence described in examples 104 a] to c]) in the presence of triphenylphosphine and di-tert-butyl azodicarboxylate to yield [rac]-3-(4-{2-[2-(2-chloro-phenyl)-4-methyl-thiazol-5-yl]-ethoxy}-2-methyl-phenyl)-2-ethoxy-propionic acid ethyl ester as colorless liquid.

MS: 510.3 (M+Na)$^+$, 490.4 (M+H)$^+$, 488.2 (M+H)$^+$, 350.3, 296.4, 250.3.

b] [rac]-3-(4-{2-[2-(2-Chloro-phenyl)-4-methyl-thiazol-5-yl]-ethoxy}-2-methyl-phenyl)-2-ethoxy-propionic acid In analogy to the procedure described in example 10 d], [rac]-3-(4-{2-[2-(2-chloro-phenyl)-4-methyl-thiazol-5-yl]-ethoxy}-2-methyl-phenyl)-2-ethoxy-propionic acid ethyl ester was treated with LiOH to obtain [rac]-3-(4-{2-[2-(2-chloro-phenyl)-4-methyl-thiazol-5-yl]-ethoxy}-2-methyl-phenyl)-2-ethoxy-propionic acid as colorless liquid.

MS: 458.1 (M−H)$^−$, 412.0, 255.2.

Example 107 a] (S)-2-Ethoxy-3-{2-ethyl-4-[4-methyl-2-(4-trifluoromethyl-phenyl)-thiazol-5-ylmethoxy]-phenyl}-propionic acid methyl ester In analogy to the procedure described in example 14 b], (2S)-2-ethoxy-3-(2-ethyl-4-hydroxy-phenyl)-propionic acid methyl ester (example 23 g]) was reacted with 5-chloromethyl-4-methyl-2-(4-trifluoromethyl-phenyl)-thiazole [PCT Int. Appl. (2002), WO 0292590 A1] in the presence of cesium carbonate and potassium iodide to yield (S)-2-ethoxy-3-{2-ethyl-4-[4-methyl-2-(4-trifluoromethyl-phenyl)-thiazol-5-ylmethoxy]-phenyl}-propionic acid methyl ester as colorless oil.

MS: 530.3 (M+Na)$^+$, 508.4 (M+H)$^+$, 343.3, 300.3, 259.3.

b] (S)-2-Ethoxy-3-{2-ethyl-4-[4-methyl-2-(4-trifluoromethyl-phenyl)-thiazol-5-ylmethoxy]-phenyl}-propionic acid In analogy to the procedure described in example 10 d], (S)-2-ethoxy-3-{2-ethyl-4-[4-methyl-2-(4-trifluoromethyl-phenyl)-thiazol-5-ylmethoxy]-phenyl}-propionic acid methyl ester was treated with LiOH to obtain (S)-2-ethoxy-3-{2-ethyl-4-[4-methyl-2-(4-trifluoromethyl-phenyl)-thiazol-5-ylmethoxy]-phenyl}-propionic acid as yellow solid.

MS: 516.2 (M+Na)$^+$, 494.2 (M+H)$^+$, 429.0, 371.3, 256.1.

Example 108 a] (S)-3-{2,6-Dimethyl-4-[4-methyl-2-(4-trifluoromethyl-phenyl)-thiazol-5-methoxy]-phenyl}-2-ethoxy-propionic acid methyl ester In analogy to the procedure described in example 14 b], (2S)-2-ethoxy-3-(4-hydroxy-2,6-dimethyl-phenyl)-propionic acid methyl ester (example 103 e]) was reacted with 5-chloromethyl-4-methyl-2-(4-trifluoromethyl-phenyl)-thiazole [PCT Int. Appl. (2002), WO 0292590 A1] in the presence of cesium carbonate and potassium iodide to yield (S)-3-{2,6-dimethyl-4-[4-methyl-2-(4-trifluoromethyl-phenyl)-thiazol-5-ylmethoxy]-phenyl}-2-ethoxy-propionic acid methyl ester as yellow oil.

MS: 530.3 (M+Na)$^+$, 508.3 (M+H)$^+$, 443.5, 342.1, 269.2.

b] (S)-3-{2,6-Dimethyl-4-[4-methyl-2-(4-trifluoromethyl-phenyl)-thiazol-5-ylmethoxy]-phenyl}-2-ethoxy-propionic acid In analogy to the procedure described in example 10 d], (S)-3-{2,6-dimethyl-4-[4-methyl-2-(4-trifluoromethyl-phenyl)-thiazol-5-ylmethoxy]-phenyl}-2-ethoxy-propionic acid methyl ester was treated with LiOH to obtain (S)-3-{2,6-dimethyl-4-[4-methyl-2-(4-trifluoromethyl-phenyl)-thiazol-5-ylmethoxy]-phenyl}-2-ethoxy-propionic acid as yellow solid.

MS: 494.2 (M+H)$^+$, 388.3.

Example 109 a] [rac]-2-Ethoxy-3-{2-methyl-4-[2-(4-trifluoromethyl-phenyl)-thiazol-5-ylmethoxy]-phenyl}-propionic acid ethyl ester In analogy to the procedure described in example 10 c], [rac]-2-ethoxy-3-(4-hydroxy-2-methyl-phenyl)-propionic acid ethyl ester (example 10 b]) was reacted with [2-(4-trifluoromethyl-phenyl)-thiazol-5-yl]-methanol [PCT Int. Appl. (2002), WO 02/062774 A1] in the presence of tributylphosphine and N,N,N',N'-tetramethyl azodicarboxamide to yield [rac]-2-ethoxy-3-{2-methyl-4-[2-(4-trifluoromethyl-phenyl)-thiazol-5-ylmethoxy]-phenyl}-propionic acid ethyl ester as yellow crystals.

MS: 516.2 (M+Na)$^+$, 494.2 (M+H)$^+$, 356.3, 242.4.

b] [rac]-2-Ethoxy-3-{2-methyl-4-[2-(4-trifluoromethyl-phenyl)-thiazol-5-ylmethoxy]-phenyl}-propionic acid In analogy to the procedure described in example 10 d], [rac]-2-ethoxy-3-{2-methyl-4-[2-(4-trifluoromethyl-phenyl)-thiazol-5-ylmethoxy]-phenyl}-propionic acid ethyl ester was treated with LiOH to obtain [rac]-2-ethoxy-3-{2-methyl-4-[2-(4-trifluoromethyl-phenyl)-thiazol-5-ylmethoxy]-phenyl}-propionic acid as off-white solid.

MS: 488.1 (M+Na)$^+$, 466.1 (M+H)$^+$, 420.0, 300.1, 242.1.

Example 110 a] [rac]-2-Ethoxy-3-(2-methyl-4-{2-[4-methyl-2-(3-trifluoromethyl-phenyl)-thiazol-5-yl]-ethoxy}-phenyl)-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[4-methyl-2-(3-trifluoromethyl-phenyl)-thiazol-5-yl]-ethanol (prepared from [4-methyl-2-(3-trifluoromethyl-phenyl)-thiazol-5-yl]-methanol (obtained from 3-trifluoromethyl-thiobenzamide and ethyl 2-chloro-acetoacetate in analogy to the procedures described in example 33 a] and 33 b]) according to the reaction sequence described in example 104 a] to c]) in the presence of triphenylphosphine and di-tert-butyl azodicarboxylate to yield [rac]-2-ethoxy-3-(2-methyl-4-{2-[4-methyl-2-(3-trifluoromethyl-phenyl)-thiazol-5-yl]-ethoxy}-phenyl)-propionic acid ethyl ester as colorless oil.

MS: 522.3 (M+H)$^+$, 478.4, 448.2.

b] [rac]-2-Ethoxy-3-(2-methyl-4-{2-[4-methyl-2-(3-trifluoromethyl-phenyl)-thiazol-5-yl]-ethoxy}-phenyl)-propionic acid In analogy to the procedure described in example 10 d], [rac]-2-ethoxy-3-(2-methyl-4-{2-[4-methyl-2-(3-trifluoromethyl-phenyl)-thiazol-5-yl]-ethoxy}-phenyl)-propionic acid ethyl ester was treated with LiOH to obtain [rac]-2-ethoxy-3-(2-methyl-4-{2-[4-methyl-2-(3-trifluoromethyl-phenyl)-thiazol-5-yl]-ethoxy}-phenyl)-propionic acid as yellow oil.

MS: 492.2 (M−H)$^−$, 446.1.

Example 111 a] [rac]-2-Ethoxy-3-{2-methyl-4-[2-(4-methyl-2-phenyl-thiazol-5-yl)-ethoxy]-phenyl}-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-(4-methyl-2-phenyl-thiazol-5-yl)-ethanol (prepared from (4-methyl-2-phenyl-thiazol-5-yl)-methanol [PCT Int. Appl. (2002), WO 02/80899 A1] according to the reaction sequence described in example 104 a] to c]) in the presence of triphenylphosphine and di-tert-butyl azodicarboxylate to yield [rac]-2-ethoxy-3-{2-methyl-4-[2-(4-methyl-2-phenyl-thiazol-5-yl)-ethoxy]-phenyl}-propionic acid ethyl ester as colorless liquid.

MS: 476.3 (M+Na)$^+$, 454.4 (M+H)$^+$, 380.3, 202.1.

b] [rac]-2-Ethoxy-3-{2-methyl-4-[2-(4-methyl-2-phenyl-thiazol-5-yl)-ethoxy]-phenyl}-propionic acid In analogy to the procedure described in example 10 d], [rac]-2-ethoxy-3-{2-methyl-4-[2-(4-methyl-2-phenyl-thiazol-5-yl)-ethoxy]-phenyl}-propionic acid ethyl ester was treated with LiOH to obtain [rac]-2-ethoxy-3-{2-methyl-4-[2-(4-methyl-2-phenyl-thiazol-5-yl)-ethoxy]-phenyl}-propionic acid as colorless liquid.

MS: 424.4 (M−H)$^−$, 378.4.

Example 112 a] 2-Ethoxy-3-(2-methyl-4-{1-[4-methyl-2-(4-trifluoromethyl-phenyl)-thiazol-5-yl]-ethoxy}-phenyl)-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-1-[4-methyl-2-(4-trifluoromethyl-phenyl)-thiazol-5-yl]-ethanol [PCT Int. Appl. (2002), WO 02/062774 A1] in the presence of tributylphosphine and N,N,N',N'-tetramethyl azodicarboxamide to yield 2-ethoxy-3-(2-methyl-4-{1-[4-methyl-2-(4-trifluoromethyl-phenyl)-thiazol-5-yl]-ethoxy}-phenyl)-propionic acid ethyl ester as a mixture of two diastereomeric racemates as colorless liquid.

MS: 544.2 (M+Na)$^+$, 522.3 (M+H)$^+$, 478.3, 298.4, 219.4.

b] 2-Ethoxy-3-(2-methyl-4-{1-[4-methyl-2-(4-trifluoromethyl-phenyl)-thiazol-5-yl]-ethoxy}-phenyl)-propionic acid (mixture of two diastereomeric racemates)

In analogy to the procedure described in example 10 d], 2-ethoxy-3-(2-methyl-4-{1-[4-methyl-2-(4-trifluoromethyl-phenyl)-thiazol-5-yl]-ethoxy}-phenyl)-propionic acid ethyl ester (mixture of two diastereomeric racemates) was treated with LiOH to obtain 2-ethoxy-3-(2-methyl-4-{1-[4-methyl-2-(4-trifluoromethyl-phenyl)-thiazol-5-yl]-ethoxy}-phenyl)-propionic acid as a mixture of two diastereomeric racemates as colorless foam.

MS: 516.1 (M+Na)$^+$, 494.2 (M+H)$^+$, 450.1, 371.3.

Example 113 a] [rac]-2-Ethoxy-3-(2-methyl-4-{1-methyl-1-[4-methyl-2-(4-trifluoromethyl-phenyl)-thiazol-5-yl]-ethoxy}-phenyl)-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[4-methyl-2-(4-trifluoromethyl-phenyl)-thiazol-5-yl]-propan-2-ol [PCT Int. Appl. (2002), WO 02/062774 A1] in the presence of tributylphosphine and N,N,N',N'-tetramethyl azodicarboxamide to yield [rac]-2-ethoxy-3-(2-methyl-4-{1-methyl-1-[4-methyl-2-(4-trifluoromethyl-phenyl)-thiazol-5-yl]-ethoxy}-phenyl)-propionic acid ethyl ester as light yellow liquid.

MS: 558.4 (M+Na)$^+$, 536.4 (M+H)$^+$, 492.2, 284.1.

b] [rac]-2-Ethoxy-3-(2-methyl-4-{1-methyl-1-[4-methyl-2-(4-trifluoromethyl-phenyl)-thiazol-5-yl]-ethoxy}-phenyl)-propionic acid In analogy to the procedure described in example 10 d], [rac]-2-ethoxy-3-(2-methyl-4-{1-methyl-1-[4-methyl-2-(4-trifluoromethyl-phenyl)-thiazol-5-yl]-ethoxy}-phenyl)-propionic acid ethyl ester was treated with LiOH to obtain [rac]-2-ethoxy-3-(2-methyl-4-{1-methyl-1-[4-methyl-2-(4-trifluoromethyl-phenyl)-thiazol-5-yl]-ethoxy}-phenyl)-propionic acid as colorless liquid.

MS: 506.2 (M–H)$^-$, 462.1.

Example 114 a] 2-Ethoxy-3-(2-methyl-4-{2-methyl-1-[4-methyl-2-(4-trifluoromethyl-phenyl)-thiazol-5-yl]-propoxy}-phenyl)-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-2-methyl-1-[4-methyl-2-(4-trifluoromethyl-phenyl)-thiazol-5-yl]-propan-1-ol [PCT Int. Appl. (2002), WO 02/062774 A1] in the presence of tributylphosphine and N,N,N',N'-tetramethyl azodicarboxamide to yield 2-ethoxy-3-(2-methyl-4-{2-methyl-1-[4-methyl-2-(4-trifluoromethyl-phenyl)-thiazol-5-yl]-propoxy}-phenyl)-propionic acid ethyl ester as a mixture of two diastereomeric racemates as light yellow liquid.

MS: 572.3 (M+Na)$^+$, 550.3 (M+H)$^+$, 508.4, 298.4.

b] 2-Ethoxy-3-(2-methyl-4-{2-methyl-1-[4-methyl-2-(4-trifluoromethyl-phenyl)-thiazol-5-yl]-propoxy}-phenyl)-propionic acid (mixture of two diastereomeric racemates)

In analogy to the procedure described in example 10 d], 2-ethoxy-3-(2-methyl-4-{2-methyl-1-[4-methyl-2-(4-trifluoromethyl-phenyl)-thiazol-5-yl]-propoxy}-phenyl)-propionic acid ethyl ester (mixture of two diastereomeric racemates) was treated with LiOH to obtain 2-ethoxy-3-{2-methyl-4-(2-methyl-1-[4-methyl-2-(4-trifluoromethyl-phenyl)-thiazol-5-yl]-propoxy}-phenyl)-propionic acid as a mixture of two diastereomeric racemates as colorless foam.

MS: 520.2 (M–H)$^-$, 473.8, 255.2.

Example 115 a] [rac]-2-Ethoxy-3-(2-methyl-4-{1-methyl-1-[2-(4-trifluoromethyl-phenyl)-thiazol-5-yl]-ethoxy}-phenyl)-propionic acid ethyl ester In analogy to the procedure described in example 10 c], [rac]-2-ethoxy-3-(4-hydroxy-2-methyl-phenyl)-propionic acid ethyl ester (example 10 b]) was reacted with 2-[2-(4-trifluoromethyl-phenyl)-thiazol-5-yl]-propan-2-ol [PCT Int. Appl. (2002), WO 02/062774 A1] in the presence of tributylphosphine and N,N,N',N'-tetramethyl azodicarboxamide to yield [rac]-2-ethoxy-3-(2-methyl-4-{1-methyl-1-[2-(4-trifluoromethyl-phenyl)-thiazol-5-yl]-ethoxy}-phenyl)-propionic acid ethyl ester as yellow liquid.

MS: 544.3 (M+Na)$^+$, 522.2 (M+H)$^+$, 478.3.

b] [rac]-2-Ethoxy-3-(2-methyl-4-{1-methyl-1-[2-(4-trifluoromethyl-phenyl)-thiazol-5-yl]-ethoxy}-phenyl)-propionic acid In analogy to the procedure described in example 10 d], [rac]-2-ethoxy-3-(2-methyl-4-{1-methyl-1-[2-(4-trifluoromethyl-phenyl)-thiazol-5-yl]-ethoxy}-phenyl)-propionic acid ethyl ester was treated with LiOH to obtain [rac]-2-ethoxy-3-(2-methyl-4-{1-methyl-1-[2-(4-trifluoromethyl-phenyl)-thiazol-5-yl]-ethoxy}-phenyl)-propionic acid as colorless oil.

MS: 516.2 (M+Na)$^+$, 494.2 (M+H)$^+$, 450.1.

Example 116 a] 2-Ethoxy-3-(2-methyl-4-{1-[2-(4-trifluoromethyl-phenyl)-thiazol-5-yl]-ethoxy}-phenyl)-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-1-[2-(4-trifluoromethyl-phenyl)-thiazol-5-yl]-ethanol [PCT Int. Appl. (2002), WO 02/062774 A1] in the presence of tributylphosphine and N,N,N',N'-tetramethyl azodicarboxamide to yield 2-ethoxy-3-(2-methyl-4-{1-[2-(4-trifluoromethyl-phenyl)-thiazol-5-yl]-ethoxy}-phenyl)-propionic acid ethyl ester as a mixture of two diastereomeric racemates as colorless liquid.

b] 2-Ethoxy-3-(2-methyl-4-{1-[2-(4-trifluoromethyl-phenyl)-thiazol-5-yl]-ethoxy}-phenyl)-propionic acid (mixture of two diastereomeric racemates)

In analogy to the procedure described in example 10 d], 2-ethoxy-3-(2-methyl-4-{1-[2-(4-trifluoromethyl-phenyl)-thiazol-5-yl]-ethoxy}-phenyl)-propionic acid ethyl ester (mixture of two diastereomeric racemates) was treated with LiOH to obtain 2-ethoxy-3-(2-methyl-4-{1-[2-(4-trifluoromethyl-phenyl)-thiazol-5-yl]-ethoxy}-phenyl)-propionic acid as a mixture of two diastereomeric racemates as light yellow liquid.

MS: 478.1 (M–H)$^-$, 432.2, 388.2.

Example 117 a] 2-Ethoxy-3-(2-methyl-4-{1-[4-methyl-2-(4-trifluoromethyl-phenyl)-thiazol-5-yl]-but-3-enyloxy}-phenyl)-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-1-[4-methyl-2-(4-trifluoromethyl-phenyl)-thiazol-5-yl]-but-3-en-1-ol [PCT Int. Appl. (2002), WO 02/062774 A1] in the presence of tributylphosphine and N,N,N',N'-tetramethyl azodicarboxamide to yield 2-ethoxy-3-(2-methyl-4-=1-[4-methyl-2-(4-trifluoromethyl-phenyl)-thiazol-5-yl]-but-3-enyloxy}-phenyl)-propionic acid ethyl ester as a mixture of two diastereomeric racemates as yellow liquid.

MS: 570.3 (M+Na)$^+$, 548.2 (M+H)$^+$, 343.3, 296.3.

b] 2-Ethoxy-3-(2-methyl-4-{1-[4-methyl-2-(4-trifluoromethyl-phenyl)-thiazol-5-yl]-but-3-enyloxy}-phenyl)-propionic acid (mixture of two diastereomeric racemates)

In analogy to the procedure described in example 10 d], 2-ethoxy-3-(2-methyl-4-{1-[4-methyl-2-(4-trifluoromethyl-phenyl)-thiazol-5-yl]-but-3-enyloxy}-phenyl)-propionic acid ethyl ester (mixture of two diastereomeric racemates) was treated with LiOH to obtain 2-ethoxy-3-(2-methyl-4-{1-[4-methyl-2-(4-trifluoromethyl-phenyl)-thiazol-5-yl]- but-3-enyloxy}-phenyl)-propionic acid as a mixture of two diastereomeric racemates as colorless solid.

MS: 518.2 (M–H)⁻, 474.2, 392.2.

Example 118 a] 2-Ethoxy-3-(2-methyl-4-{1-[4-methyl-2-(4-trifluoromethyl-phenyl)-thiazol-5-yl]-butoxy}-phenyl)-propionic acid ethyl ester (mixture of two diastereomeric racemates)

A solution of 2-ethoxy-3-(2-methyl-4-{1-[4-methyl-2-(4-trifluoromethyl-phenyl)-thiazol-5-yl]-but-3-enyloxy}-phenyl)-propionic acid ethyl ester (mixture of two diastereomeric racemates; 100 mg, 180 μmol; example 117 a]) in ethanol (5 ml) was treated with 10% palladium on charcoal (10 mg) under a hydrogen atmosphere at ambient temperature for 2 h. The mixture was filtered through a celite pad and rinsed with ethanol. The filtrate was concentrated to dryness and the residue purified by column chromatography (silica gel, heptane/AcOEt) to give 60 mg (110 μmol, 60%) of the title compound as colorless oil.

MS: 573.3 (M+Na)⁺, 550.3 (M+H)⁺, 298.3, 256.1.

b] 2-Ethoxy-3-(2-methyl-4-{1-[4-methyl-2-(4-trifluoromethyl-phenyl)-thiazol-5-yl]-butoxy}-phenyl)-propionic acid (mixture of two diastereomeric racemates)

In analogy to the procedure described in example 10 d], 2-ethoxy-3-(2-methyl-4-{1-[4-methyl-2-(4-trifluoromethyl-phenyl)-thiazol-5-yl]-butoxy}-phenyl)-propionic acid ethyl ester (mixture of two diastereomeric racemates) was treated with LiOH to obtain 2-ethoxy-3-(2-methyl-4-{1-[4-methyl-2-(4-trifluoromethyl-phenyl)-thiazol-5-yl]-butoxy}-phenyl)-propionic acid as a mixture of two diastereomeric racemates as colorless foam.

MS: 520.3 (M–H)⁻, 476.2.

Example 119 a] (2S)-2-Ethoxy-3-(2-ethyl-4-{(1R/S)-[4-methyl-2-(4-trifluoromethyl-phenyl)-thiazol-5-yl]-ethoxy}-phenyl)-propionic acid methyl ester In analogy to the procedure described in example 10 c], (2S)-2-ethoxy-3-(2-ethyl-4-hydroxy-phenyl)-propionic acid methyl ester (example 23 g]) was reacted with [rac]-1-[4-methyl-2-(4-trifluoromethyl-phenyl)-thiazol-5-yl]-ethanol [PCT Int. Appl. (2002), WO 02/062774 A1] in the presence of tributylphosphine and N,N,N',N'-tetramethyl azodicarboxamide to yield (2S)-2-ethoxy-3-(2-ethyl-4-{(1R/S)-[4-methyl-2-(4-trifluoromethyl-phenyl)-thiazol-5-yl]-ethoxy}-phenyl)-propionic acid methyl ester as colorless oil.

MS: 544.2 (M+Na)⁺, 522.2 (M+H)⁺.

b] (2S)-2-Ethoxy-3-(2-ethyl-4-(1R/S)-[4-methyl-2-(4-trifluoromethyl-phenyl)-thiazol-5-yl]-ethoxy}-phenyl)-propionic acid In analogy to the procedure described in example 10 d], (2S)-2-ethoxy-3-(2-ethyl-4-{(1R/S)-[4-methyl-2-(4-trifluoromethyl-phenyl)-thiazol-5-yl]-ethoxy}-phenyl)-propionic acid methyl ester was treated with LiOH to obtain (2S)-2-ethoxy-3-(2-ethyl-4-{(1R/S)-[4-methyl-2-(4-trifluoromethyl-phenyl)-thiazol-5-yl]-ethoxy}-phenyl)-propionic acid as yellow oil.

MS: 530.3 (M+Na)⁺, 508.4 (M+H)⁺, 367.3.

Example 120 a] (2S)-2-Ethoxy-3-(2-methoxy-4-{(1R/S)-[4-methyl-2-(4-trifluoromethyl-phenyl)-thiazol-5-yl]-ethoxy}-phenyl)-propionic acid methyl ester In analogy to the procedure described in example 10 c], (2S)-2-ethoxy-3-(4-hydroxy-2-methoxy-phenyl)-propionic acid methyl ester (example 21 c]) was reacted with [rac]-1-[4-methyl-2-(4-trifluoromethyl-phenyl)-thiazol-5-yl]-ethanol [PCT Int. Appl. (2002), WO 02/062774 A1] in the presence of tributylphosphine and N,N,N',N'-tetramethyl azodicarboxamide to yield (2S)-2-ethoxy-3-(2-methoxy-4-{(1R/S)-[4-methyl-2-(4-trifluoromethyl-phenyl)-thiazol-5-yl]-ethoxy}-phenyl)-propionic acid methyl ester as colorless oil.

MS: 508.4 (M-15)⁺.

b] (2S)-2-Ethoxy-3-(2-methoxy-4-{(1R/S)-[4-methyl-2-(4-trifluoromethyl-phenyl)-thiazol-5-yl]-ethoxy}-phenyl)-propionic acid In analogy to the procedure described in example 10 d], (2S)-2-ethoxy-3-(2-methoxy-4-{(1R/S)-[4-methyl-2-(4-trifluoromethyl-phenyl)-thiazol-5-yl]-ethoxy}-phenyl)-propionic acid methyl ester was treated with LiOH to obtain (2S)-2-ethoxy-3-(2-methoxy-4-{(1R/S)-[4-methyl-2-(4-trifluoromethyl-phenyl)-thiazol-5-yl]-ethoxy}-phenyl)-propionic acid as colorless oil.

MS: 530.3 (M-15)⁺.

Example 121 a] [rac]-Cyclopropyl-[4-methyl-2-(4-trifluoromethyl-phenyl)-thiazol-5-yl]-methanol To a solution of 4-methyl-2-(4-trifluoromethyl-phenyl)-thiazole-5-carbaldehyde (500 mg, 1.8 mmol; PCT Int. Appl. (2002), WO 02/062774 A1) in tetrahydrofuran (25 ml) was slowly added a 0.5 M solution of cyclopropylmagnesium bromide in tetrahydrofuran (4 ml, 2 mmol) under an argon atmosphere at –10° C. The mixture was naturally warmed to room temperature, stirred for 1.5 h, quenched with saturated NH₄Cl solution (50 ml) and extracted two times with ethyl acetate. The combined organic layers were washed with brine and water and dried over sodium sulfate. The filtrate was concentrated to dryness to give 560 mg (1.79 mmol, 97%) of the title compound as yellow solid.

b] 3-(4-{Cyclopropyl-[4-methyl-2-(4-trifluoromethyl-phenyl)-thiazol-5-yl]-methoxy}-2-methyl-phenyl)-2-ethoxy-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-cyclopropyl-[4-methyl-2-(4-trifluoromethyl-phenyl)-thiazol-5-yl]-methanol in the presence of tributylphosphine and N,N,N',N'-tetramethyl azodicarboxamide to yield 3-(4-{cyclopropyl-[4-methyl-2-(4-trifluoromethyl-phenyl)-thiazol-5-yl]-methoxy}-2-methyl-phenyl)-2-ethoxy-propionic acid ethyl ester as a mixture of two diastereomeric racemates as yellow liquid.

MS: 570.3 (M+Na)⁺, 548.2 (M+H)⁺, 494.2, 416.3, 296.3.

c] 3-(4-{Cyclopropyl-[4-methyl-2-(4-trifluoromethyl-phenyl)-thiazol-5-yl]-methoxy}-2-methyl-phenyl)-2-ethoxy-propionic acid (mixture of two diastereomeric racemates)

In analogy to the procedure described in example 10 d], 3-(4-{cyclopropyl-[4-methyl-2-(4-trifluoromethyl-phenyl)-thiazol-5-yl]-methoxy}-2-methyl-phenyl)-2-ethoxy-propionic acid ethyl ester (mixture of two diastereomeric racemates) was treated with LiOH to obtain 3-(4-{cyclopropyl-[4-methyl-2-(4-trifluoromethyl-phenyl)-thiazol-5-yl]-methoxy}-2-methyl-phenyl)-2-ethoxy-propionic acid as a mixture of two diastereomeric racemates as colorless solid.

MS: 542.2 (M+Na)⁺, 520.2 (M+H)⁺, 480.2, 392.2, 296.1.

Example 122 a] 3-(4-{Cyclopentyl-[4-methyl-2-(4-trifluoromethyl-phenyl)-thiazol-5-yl]-methoxy}-2-methyl-phenyl)-2-ethoxy-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-cyclopentyl-(4-methyl-2-(4-trifluoromethyl-phenyl)-thiazol-5-yl]-methanol [PCT Int. Appl. (2002), WO 02/062774 A1] in the presence of tributylphosphine and N,N,N',N'-tetramethyl azodicarboxamide to yield 3-(4-{cyclopentyl-[4-methyl-2-(4-trifluoromethyl-phenyl)-thiazol-5-yl]-methoxy}-2-methyl-phenyl)-2-ethoxy-propionic acid ethyl ester as a mixture of two diastereomeric racemates as colorless liquid.

MS: 598.3 (M+Na)$^+$, 576.3 (M+H)$^+$, 340.3, 312.2, 247.1.

b] 3-(4-{Cyclopentyl-[4-methyl-2-(4-trifluoromethyl-phenyl)-thiazol-5-yl]-methoxy}-2-methyl-phenyl)-2-ethoxy-propionic acid (mixture of two diastereomeric racemates)

In analogy to the procedure described in example 10 d], 3-(4-{cyclopentyl-[4-methyl-2-(4-trifluoromethyl-phenyl)-thiazol-5-yl]-methoxy}-2-methyl-phenyl)-2-ethoxy-propionic acid ethyl ester (mixture of two diastereomeric racemates) was treated with LiOH to obtain 3-(4-{cyclopentyl-[4-methyl-2-(4-trifluoromethyl-phenyl)-thiazol-5-yl]-methoxy}-2-methyl-phenyl)-2-ethoxy-propionic acid as a mixture of two diastereomeric racemates as colorless liquid.

MS: 546.3 (M–H)$^-$, 424.4.

Example 123 a] 2-Ethoxy-3-(2-methyl-4-{[4-methyl-2-(4-trifluoromethyl-phenyl)-thiazol-5-yl]-phenyl-methoxy}-phenyl)-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-[4-methyl-2-(4-trifluoromethyl-phenyl)-thiazol-5-yl]-phenyl-methanol [PCT Int. Appl. (2002), WO 02/062774 A1] in the presence of tributylphosphine and N,N,N',N'-tetramethyl azodicarboxamide to yield 2-ethoxy-3-(2-methyl-4-{[4-methyl-2-(4-trifluoromethyl-phenyl)-thiazol-5-yl]-phenyl-methoxy}-phenyl)-propionic acid ethyl ester as a mixture of two diastereomeric racemates as colorless liquid.

MS: 606.2 (M+Na)$^+$, 584.4 (M+H)$^+$, 540.3, 508.3, 356.3.

b] 2-Ethoxy-3-(2-methyl-4-{[4-methyl-2-(4-trifluoromethyl-phenyl)-thiazol-5-yl]-phenyl-methoxy}-phenyl)-propionic acid (mixture of two diastereomeric racemates)

In analogy to the procedure described in example 10 d], 2-ethoxy-3-(2-methyl-4-{[4-methyl-2-(4-trifluoromethyl-phenyl)-thiazol-5-yl]-phenyl-methoxy}-phenyl)-propionic acid ethyl ester (mixture of two diastereomeric racemates) was treated with LiOH to obtain 2-ethoxy-3-(2-methyl-4-{[4-methyl-2-(4-trifluoromethyl-phenyl)-thiazol-5-yl]-phenyl-methoxy}-phenyl)-propionic acid as a mixture of two diastereomeric racemates as off-white gum.

MS: 578.2 (M+Na)$^+$, 556.2 (M+H)$^+$, 512.3, 493.2, 441.1, 332.1.

Example 124 a] [rac]-3-[1.3]Dioxan-2-yl-1-[4-methyl-2-(4-trifluoromethyl-phenyl)-thiazol-5-yl]-propan-1-ol To a solution of 4-methyl-2-(4-trifluoromethyl-phenyl)-thiazole-5-carbaldehyde (130 mg, 480 μmol; PCT Int. Appl. (2002), WO 02/062774 A1) in tetrahydrofuran (10 ml) was slowly added a 0.5 M solution of (1,3-dioxan-2-yl) magnesium bromide in tetrahydrofuran (1.3 ml, 679 μmol) under an argon atmosphere at ambient temperature. The mixture was stirred for 5 h at 30° C., quenched with saturated NH$_4$Cl solution (10 ml) and extracted two times with ethyl acetate. The combined organic layers were washed with brine and water and dried over sodium sulfate. The filtrate was concentrated to dryness to give 185 mg (478 μmol, 99%) of the title compound as yellow solid.

MS: 388.2 (M+H)$^+$, 330.5, 275.4, 248.5.

b] 3-(4-{3-[1,3]Dioxan-2-yl-1-[4-methyl-2-(4-trifluoromethyl-phenyl)-thiazol-5-yl]-propoxy}-2-methyl-phenyl)-2-ethoxy-propionic acid ethyl ester (mixture of two diastereomeric racemates)

In analogy to the procedure described in example 10 c], [rac]-2-ethoxy-3-(4-hydroxy-2-methyl-phenyl)-propionic acid ethyl ester (example 10 b]) was reacted with [rac]-3-[1,3]dioxan-2-yl-1-[4-methyl-2-(4-trifluoromethyl-phenyl)-thiazol-5-yl]-propan-1-ol in the presence of tributylphosphine and N,N,N',N'-tetramethyl azodicarboxamide to yield 3-(4-{3-[1,3]dioxan-2-yl-1-[4-methyl-2-(4-trifluoromethyl-phenyl)-thiazol-5-yl]-propoxy}-2-methyl-phenyl)-2-ethoxy-propionic acid ethyl ester as a mixture of two diastereomeric racemates as colorless oil.

MS: 644.4 (M+Na)$^+$, 622.3 (M+H)$^+$, 370.2, 268.4.

c] 3-(4-{3-[1,3]Dioxan-2-yl-1-[4-methyl-2-(4-trifluoromethyl-phenyl)-thiazol-5-yl]-propoxy}-2-methyl-phenyl)-2-ethoxy-propionic acid (mixture of two diastereomeric racemates)

In analogy to the procedure described in example 10 d], 3-(4-{3-[1,3]dioxan-2-yl-1-[4-methyl-2-(4-trifluoromethyl-phenyl)-thiazol-5-yl]-propoxy}-2-methyl-phenyl)-2-ethoxy-propionic acid ethyl ester (mixture of two diastereomeric racemates) was treated with LiOH to obtain 3-(4-{3-[1,3] dioxan-2-yl-1-[4-methyl-2-(4-trifluoromethyl-phenyl)-thiazol-5-yl]-propoxy}-2-methyl-phenyl)-2-ethoxy-propionic acid as a mixture of two diastereomeric racemates as colorless liquid.

MS: 592.4 (M–H)$^-$, 548.3.

Example 125 a] 2-[(4-Benzyloxy-2-methyl-phenyl)-hydroxy-methyl]-butyric acid ethyl ester (mixture of two diastereomeric racemates)

To a solution of butyric acid ethyl ester (2.9 ml, 22.1 mmol) in tetrahydrofuran (125 ml) was added a 2 M solution of lithium diisopropylamide in tetrahydrofuran (11.6 ml, 23.2 mmol) dropwise over 15 minutes at –78° C. under an argon atmosphere. After stirring for 10 minutes a solution of 4-benzyloxy-2-methyl-benzaldehyde (5 g, 22.1 mmol) in tetrahydrofuran (125 ml) was added dropwise over 30 minutes and stirring was continued for 20 h at –78° C. Saturated aqueous ammonium chloride (60 ml) was added dropwise and the mixture was warmed to ambient temperature. Ice water/brine 1/1 was added and the mixture was extracted two times with ethyl acetate. The combined organic layers were washed with ice water/brine 1/1 and dried over sodium sulfate. The filtrate was concentrated to dryness and the residue purified by column chromatography (silica gel, heptane/AcOEt) to give 3.4 g (9.9 mmol, 45%) of the tide compound as a mixture of two diastereomeric racemates as light yellow oil.

MS: 365.3 (M+Na)$^+$, 360.3 (M+NH$_4$)$^+$, 325.4.

b] (E,Z)-3-(4-Benzyloxy-2-methyl-phenyl)-2-ethyl-acrylic acid ethyl ester

To a solution of 2-[(4-benzyloxy-2-methyl-phenyl)-hydroxy-methyl]-butyric acid ethyl ester (3.4 g, 9.9 mmol;

mixture of two diastereomeric racemates) in dimethyl formamide (34 ml) was added concentrated sulfuric acid (1.4 ml) and the mixture was stirred for 1.5 h at 100° C. under an argon atmosphere. The reaction mixture was cooled to ambient temperature, ice water/saturated aqueous hydrogen carbonate 1/1 and ethyl acetate were added and the layers were separated. The aqueous layer was extracted with ethyl acetate, the combined organic layers were washed with ice water/brine 1/1 and dried over sodium sulfate. The filtrate was concentrated to dryness and the residue purified by column chromatography (silica gel, heptane/AcOEt) to give 1.9 g (5.9 mmol, 59%) of (E,Z)-3-(4-benzyloxy-2-methyl-phenyl)-2-ethyl-acrylic acid ethyl ester as colorless oil.

MS: 342.3 $(M+NH_4)^+$, 325.4 $(M+H)^+$, 225.5.

c] [rac]-2-(4-Hydroxy-2-methyl-benzyl)-butyric acid ethyl ester

In analogy to the procedure described in example 118 a], (E,Z)-3-(4-benzyloxy-2-methyl-phenyl)-2-ethyl-acrylic acid ethyl ester was hydrogenated in the presence of palladium on charcoal to obtain [rac]-2-(4-hydroxy-2-methyl-benzyl)-butyric acid ethyl ester as colorless liquid.

MS: 254.4 $(M+NH_4)^+$.

d] [rac]-2-{2-Methyl-4-[4-methyl-2-(4-trifluoromethyl-phenyl)-thiazol-5-ylmethoxy]-benzyl}-butyric acid ethyl ester In analogy to the procedure described in example 14 b], [rac]-2-(4-hydroxy-2-methyl-benzyl)-butyric acid ethyl ester was reacted with 5-chloromethyl-4-methyl-2-(4-trifluoromethyl-phenyl)-thiazole [PCT Int. Appl. (2002), WO 0292590 A1] in the presence of cesium carbonate and potassium iodide to yield [rac]-2-{2-methyl-4-[4-methyl-2-(4-trifluoromethyl-phenyl)-thiazol-5-ylmethoxy]-benzyl}-butyric acid ethyl ester as colorless oil.

e] [rac]-2-{2-Methyl-4-[4-methyl-2-(4-trifluoromethyl-phenyl)-thiazol-5-ylmethoxy]-benzyl}-butyric acid In analogy to the procedure described in example 10 d], [rac]-2-{2-methyl-4-[4-methyl-2-(4-trifluoromethyl-phenyl)-thiazol-5-ylmethoxy]-benzyl}-butyric acid ethyl ester was treated with 3 N NaOH to obtain [rac]-2-{2-methyl-4-[4-methyl-2-(4-trifluoromethyl-phenyl)-thiazol-5-ylmethoxy]-benzyl}-butyric acid as colorless solid.

MS: 462.2 $(M-H)^-$, 311.2.

Example 126 a] 2-[(4-Benzyloxy-2-methyl-phenyl)-hydroxy-methyl]-heptanoic acid methyl ester (mixture of two diastereomeric racemates)

In analogy to the procedure described in example 125 a], methyl heptanoate was deprotonated with lithium diisopropylamide and reacted with 4-benzyloxy-2-methyl-benzaldehyde in tetrahydrofuran to obtain 2-[(4-benzyloxy-2-methyl-phenyl)-hydroxy-methyl]-heptanoic acid methyl ester as a mixture of two diastereomeric racemates as light yellow oil.

MS: 393.3 $(M+Na)^+$, 388.3 $(M+NH_4)^+$, 353.3.

b] (E,Z)-3-(4-Benzyloxy-2-methyl-phenyl)-2-pentyl-acrylic acid methyl ester

In analogy to the procedure described in example 125 b], 2-[(4-benzyloxy-2-methyl-phenyl)-hydroxy-methyl]-heptanoic acid methyl ester (mixture of two diastereomeric racemates) was treated with concentrated sulfuric acid in dimethyl formamide to give (E,Z)-3-(4-benzyloxy-2-methyl-phenyl)-2-pentyl-acrylic acid methyl ester as yellow oil.

MS: 370.4 $(M+NH_4)^+$.

c] [rac]-2-(4-Hydroxy-2-methyl-benzyl)-heptanoic acid methyl ester

In analogy to the procedure described in example 118 a], (E,Z)-3-(4-benzyloxy-2-methyl-phenyl)-2-pentyl-acrylic acid methyl ester was hydrogenated in the presence of palladium on charcoal to obtain [rac]-2-(4-hydroxy-2-methyl-benzyl)-heptanoic acid methyl ester as light brown oil.

MS: 282.4 $(M+NH_4)^+$.

d] [rac]-2-{2-Methyl-4-[4-methyl-2-(4-trifluoromethyl-phenyl)-thiazol-5-ylmethoxy]-benzyl}-heptanoic acid methyl ester In analogy to the procedure described in example 14 b], [rac]-2-(4-hydroxy-2-methyl-benzyl)-heptanoic acid methyl ester was reacted with 5-chloromethyl-4-methyl-2-(4-trifluoromethyl-phenyl)-thiazole [PCT Int. Appl. (2002), WO 0292590 A1] in the presence of cesium carbonate and potassium iodide to yield [rac]-2-{2-methyl-4-(4-methyl-2-(4-trifluoromethyl-phenyl)-thiazol-5-ylmethoxy]-benzyl}-heptanoic acid methyl ester as colorless oil.

MS: 520.4 $(M+H)^+$.

e] [rac]-2-{2-Methyl-4-[4-methyl-2-(4-trifluoromethyl-phenyl)-thiazol-5-ylmethoxy]-benzyl}-heptanoic acid In analogy to the procedure described in example 10 d], [rac]-2-{2-methyl-4-[4-methyl-2-(4-trifluoromethyl-phenyl)-thiazol-5-ylmethoxy]-benzyl}-heptanoic acid methyl ester was treated with 3 N NaOH to obtain [rac]-2-{2-methyl-4-[4-methyl-2-(4-trifluoromethyl-phenyl)-thiazol-5-ylmethoxy]-benzyl}-heptanoic acid as yellow crystals.

MS: 504.3 $(M-H)^-$.

Example 127 a] 2-(4-{Cyclopropyl-[4-methyl-2-(4-trifluoromethyl-phenyl)-thiazol-5-yl]-methoxy]-2-methyl-benzyl)-heptanoic acid methyl ester (mixture of two diastereomeric racemates)

In analogy to the procedure described in example 10 c], [rac]-2-(4-hydroxy-2-methyl-benzyl)-heptanoic acid methyl ester (example 126 c]) was reacted with [rac]-cyclopropyl-[4-methyl-2-(4-trifluoromethyl-phenyl)-thiazol-5-yl]-methanol (example 121 a]) in the presence of tributylphosphine and N,N,N',N'-tetramethyl azodicarboxamide to yield 2-(4-cyclopropyl-[4-methyl-2-(4-trifluoromethyl-phenyl)-thiazol-5-yl]-methoxy}-2-methyl-benzyl)-heptanoic acid methyl ester as a mixture of two diastereomeric racemates as yellow oil.

MS: 560.5 $(M+H)^+$, 421.5.

b] 2-(4-{Cyclopropyl-[4-methyl-2-(4-trifluoromethyl-phenyl)-thiazol-5-yl]-methoxy}-2-methyl-benzyl)-heptanoic acid (mixture of two diastereomeric racemates)

In analogy to the procedure described in example 10 d], 2-(4-{cyclopropyl-[4-methyl-2-(4-trifluoromethyl-phenyl)-thiazol-5-yl]-methoxy}-2-methyl-benzyl)-heptanoic acid methyl ester (mixture of two diastereomeric racemates) was treated with LiOH to obtain 2-(4-{cyclopropyl-[4-methyl-2-(4-trifluoromethyl-phenyl)-thiazol-5-yl]-methoxy}-2-methyl-benzyl)-heptanoic acid as a mixture of two diastereomeric racemates as colorless oil.

MS: 568.3 $(M+Na)^+$, 546.2 $(M+H)^+$.

Example 128 a] 2-(4-{Cyclopropyl-[4-methyl-2-(4-trifluoromethyl-phenyl)-thiazol-5-yl]-methoxy}-2-methyl-benzyl)-butyric acid ethyl ester (mixture of two diastereomeric racemates)

In analogy to the procedure described in example 10 c], [rac]-2-(4-hydroxy-2-methyl-benzyl)-butyric acid ethyl ester (example 125 c]) was reacted with [rac]-cyclopropyl-[4-methyl-2-(4-trifluoromethyl-phenyl)-thiazol-5-yl]-methanol (example 121 a]) in the presence of tributylphosphine and N,N,N',N'-tetramethyl azodicarboxamide to yield 2-(4-{cyclopropyl-[4-methyl-2-(4-trifluoromethyl-phenyl)- thiazol-5-yl]-methoxy}-2-methyl-benzyl)-butyric acid ethyl ester as a mixture of two diastereomeric racemates as light yellow liquid.

MS: 532.5 (M+H)$^+$, 345.4.

b] 2-(4-{Cyclopropyl-[4-methyl-2-(4-trifluoromethyl-phenyl)-thiazol-5-yl]-methoxy}-2-methyl-benzyl)-butyric acid (mixture of two diastereomeric racemates)

In analogy to the procedure described in example 10 d], 2-(4-{cyclopropyl-[4-methyl-2-(4-trifluoromethyl-phenyl)-thiazol-5-yl]-methoxy}-2-methyl-benzyl)-butyric acid ethyl ester (mixture of two diastereomeric racemates) was treated with LiOH to obtain 2-(4-{cyclopropyl-[4-methyl-2-(4-trifluoromethyl-phenyl)-thiazol-5-yl]-methoxy}-2-methyl-benzyl)-butyric acid as a mixture of two diastereomeric racemates as colorless liquid.

MS: 504.4 (M+H)$^+$.

Example 129 a] [rac]-2-(2-Methyl-4-{1-methyl-1-[4-methyl-2-(4-trifluoromethyl-phenyl)-thiazol-5-yl]-ethoxy}-benzyl)-butyric acid ethyl ester In analogy to the procedure described in example 10 c], [rac]-2-(4-hydroxy-2-methyl-benzyl)-butyric acid ethyl ester (example 125 c]) was reacted with 2-[4-methyl-2-(4-trifluoromethyl-phenyl)-thiazol-5-yl]-propan-2-ol [PCT Int. Appl. (2002), WO 02/062774 A1] in the presence of tributylphosphine and N,N,N',N'-tetramethyl azodicarboxamide to yield [rac]-2-(2-methyl-4-{1-methyl-1-[4-methyl-2-(4-trifluoromethyl-phenyl)-thiazol-5-yl]-ethoxy}-benzyl)-butyric acid ethyl ester as colorless oil.

MS: 520.2 (M+H)$^+$, 284.1.

b] [rac]-2-(2-Methyl-4-{1-methyl-1-[4-methyl-2-(4-trifluoromethyl-phenyl)-thiazol-5-yl]-ethoxy]-benzyl)-butyric acid In analogy to the procedure described in example 10 d], [rac]-2-(2-methyl-4-{1-methyl-1-[4-methyl-2-(4-trifluoromethyl-phenyl)-thiazol-5-yl]-ethoxy}-benzyl)-butyric acid ethyl ester was treated with 3 N NaOH to obtain [rac]-2-(2-methyl-4-{1-methyl-1-[4-methyl-2-(4-trifluoromethyl-phenyl)-thiazol-5-yl]-ethoxy}-benzyl)-butyric acid as colorless liquid.

MS: 492.3 (M+H)$^+$.

Example 130 a] [rac]-2-(2-Methyl-4-{1-methyl-1-[4-methyl-2-(4-trifluoromethyl-phenyl)-thiazol-5-yl]-ethoxy}-benzyl)-heptanoic acid methyl ester In analogy to the procedure described in example 10 c], [rac]-2-(4-hydroxy-2-methyl-benzyl)-heptanoic add methyl ester (example 126 c]) was reacted with 2-[4-methyl-2-(4-trifluoromethyl-phenyl)-thiazol-5-yl]-propan-2-ol [PCT Int. Appl. (2002), WO 02/062774 A1] in the presence of tributylphosphine and N,N,N',N'-tetramethyl azodicarboxamide to yield [rac]-2-(2-methyl-4-{1-methyl-1-[4-methyl-2-(4-trifluoromethyl-phenyl)-thiazol-5-yl]-ethoxy}-benzyl)-heptanoic acid methyl ester as colorless oil.

MS: 548.4 (M+H)$^+$.

b] [rac]-2-(2-Methyl-4-{1-methyl-1-[4-methyl-2-(4-trifluoromethyl-phenyl)-thiazol-5-yl]-ethoxy}-benzyl)-heptanoic acid In analogy to the procedure described in example 10 d], [rac]-2-(2-methyl-4-{1-methyl-1-[4-methyl-2-(4-trifluoromethyl-phenyl)-thiazol-5-yl]-ethoxy}-benzyl)-heptanoic acid methyl ester was treated with LiOH to obtain [rac]-2-(2-methyl-4-{1-methyl-1-[4-methyl-2-(4-trifluoromethyl-phenyl)-thiazol-5-yl]-ethoxy}-benzyl)-heptanoic acid as colorless liquid.

MS: 532.3 (M–H)$^-$.

Example 131 a] 3-(4-Benzyloxy-2-methyl-phenyl)-2-butoxy-3-hydroxy-propionic acid methyl ester (mixture of two diastereomeric racemates)

In analogy to the procedure described in example 125 a], butoxy-acetic acid methyl ester (V. Franzen, L. Fikentscher, Ann. 1958, 617, 1–10) was deprotonated with lithium diisopropylamide and treated with 4-benzyloxy-2-methyl-benzaldehyde in tetrahydrofuran at –78° C. for 3 h to obtain 3-(4-benzyloxy-2-methyl-phenyl)-2-butoxy-3-hydroxy-propionic acid methyl ester as a mixture of two diastereomeric racemates as yellow liquid.

MS: 395.4 (M+Na)$^+$, 390.4 (M+NH$_4$)$^+$, 336.5.

b] (E,Z)-3-(4-Benzyloxy-2-methyl-phenyl)-2-butoxy-acrylic acid methyl ester

In analogy to the procedure described in example 125 b], 3-(4-benzyloxy-2-methyl-phenyl)-2-butoxy-3-hydroxy-propionic acid methyl ester (mixture of two diastereomeric racemates) was treated with concentrated sulfuric acid in dimethyl formamide to give (E,Z)-3-(4-benzyloxy-2-methyl-phenyl)-2-butoxy-acrylic acid methyl ester as orange liquid.

MS: 372.5 (M+NH$_4$)$^+$, 355.4 (M+H)$^+$.

c] [rac]-2-Butoxy-3-(4-hydroxy-2-methyl-phenyl)-propionic acid methyl ester

In analogy to the procedure described in example 118 a], (E,Z)-3-(4-benzyloxy-2-methyl-phenyl)-2-butoxy-acrylic acid methyl ester was hydrogenated in the presence of palladium on charcoal to obtain [rac]-2-butoxy-3-(4-hydroxy-2-methyl-phenyl)-propionic acid methyl ester as yellow liquid.

MS: 284.4 (M+NH$_4$)$^+$.

d] [rac]-2-Butoxy-3-{2-methyl-4-[4-methyl-2-(4-trifluoromethyl-phenyl)-thiazol-5-ylmethoxy]-phenyl}-propionic acid methyl ester In analogy to the procedure described in example 14 b], [rac]-2-butoxy-3-(4-hydroxy-2-methyl-phenyl)-propionic acid methyl ester was reacted with 5-chloromethyl-4-methyl-2-(4-trifluoromethyl-phenyl)-thiazole [PCT Int. Appl. (2002), WO 0292590 A1] in the presence of cesium carbonate and potassium iodide to yield [rac]-2-butoxy-3-{2-methyl-4-[4-methyl-2-(4-trifluoromethyl-phenyl)-thiazol-5-ylmethoxy]-phenyl}-propionic acid methyl ester as colorless liquid.

MS: 544.3 (M+Na)$^+$, 522.2 (M+H)$^+$.

e] [rac]-2-Butoxy-3-{2-methyl-4-[4-methyl-2-(4-trifluoromethyl-phenyl)-thiazol-5-ylmethoxy]-phenyl}-propionic acid In analogy to the procedure described in example 10 d], [rac]-2-butoxy-3-{2-methyl-4-[4-methyl-2-(4-trifluoromethyl-phenyl)-thiazol-5-ylmethoxy]-phenyl}-propionic acid methyl ester was treated with 1 N LiOH to obtain [rac]-2-butoxy-3-{2-methyl-4-[4-methyl-2-(4-trifluoromethyl-phenyl)-thiazol-5-ylmethoxy]-phenyl}-propionic acid as yellow solid.

MS: 506.2 (M–H)$^-$.

Example 132 a] 2-Butoxy-3-(4-{cyclopropyl-[4-methyl-2-(4-trifluoromethyl-phenyl)-thiazol-5-yl]-methoxy}-2-methyl-phenyl)-propionic acid methyl ester (mixture of two diastereomeric racemates)

In analogy to the procedure described in example 10 c], [rac]-2-butoxy-3-(4-hydroxy-2-methyl-phenyl)-propionic acid methyl ester (example 131 c]) was reacted with [rac]-cyclopropyl-[4-methyl-2-(4-trifluoromethyl-phenyl)-thiazol-5-yl]-methanol (example 121 a]) in the presence of tributylphosphine and N,N,N',N'-tetramethyl azodicarboxamide to yield 2-(4-{cyclopropyl-[4-methyl-2-(4-trifluoromethyl-phenyl)-thiazol-5-yl]-methoxy}-2-methyl-benzyl)-butyric acid ethyl ester as a mixture of two diastereomeric racemates as yellow liquid.

MS: 584.5 (M+Na)+, 562.4 (M+H)+, 370.4.

b] 2-Butoxy-3-(4-{cyclopropyl-[4-methyl-2-(4-trifluoromethyl-phenyl)-thiazol-5-yl]-methoxy}-2-methyl-phenyl)-propionic acid (mixture of two diastereomeric racemates)

In analogy to the procedure described in example 10 d], 2-butoxy-3-(4-{cyclopropyl-[4-methyl-2-(4-trifluoromethyl-phenyl)-thiazol-5-yl]-methoxy}-2-methyl-phenyl)-propionic acid methyl ester (mixture of two diastereomeric racemates) was treated with LiOH to obtain 2-butoxy-3-(4-{cyclopropyl-[4-methyl-2-(4-trifluoromethyl-phenyl)-thiazol-5-yl]-methoxy}-2-methyl-phenyl)-propionic acid as a mixture of two diastereomeric racemates as yellow liquid.

MS: 546.3 (M−H)−.

Example 133

[rac]-2-Ethoxy-3-(4-{2-[4-methyl-2-(4-trifluoromethyl-phenyl)-thiazol-5-yl]-ethoxy}-5,6,7,8-tetrahydro-naphthalen-1-yl)-propionic acid In analogy to the procedure described in example 1 d], [rac]-2-ethoxy-3-(4-hydroxy-5,6,7,8-tetrahydro-naphthalen-1-yl)-propionic acid methyl ester (example 2 c]) was reacted with 2-[4-methyl-2-(4-trifluoromethyl-phenyl)-thiazol-5-yl]-ethanol [PCT Int. Appl. (2001), WO 01/00603 A1] in tetrahydrofuran in the presence of triphenylphosphine and DBAD (di-tert-butyl azodicarboxylate) to yield [rac]-2-ethoxy-3-(4-{2-[4-methyl-2-(4-trifluoromethyl-phenyl)-thiazol-5-yl]-ethoxy}-5,6,7,8-tetrahydro-naphthalen-1-yl)-propionic acid methyl ester, which was further saponified in analogy to the procedure described in example 1 e], to yield [rac]-2-ethoxy-3-(4-{2-[4-methyl-2-(4-trifluoromethyl-phenyl)-thiazol-5-yl]-ethoxy}-5,6,7,8-tetrahydro-naphthalen-1-yl)-propionic acid as colorless oil.

MS: 532.3 (M−H)−.

Example 134

[rac]-2-Ethoxy-3-{4-[4-methyl-2-(4-trifluoromethyl-phenyl)-thiazol-5-ylmethoxy]-5,6,7,8-tetrahydro-naphthalen-1-yl}-propionic acid In analogy to the procedure described in example 14 b], [rac]-2-ethoxy-3-(4-hydroxy-5,6,7,8-tetrahydro-naphthalen-1-yl)-propionic acid methyl ester (example 2 c]) was reacted with 5-chloromethyl-4-methyl-2-(4-trifluoromethyl-phenyl)-thiazole [PCT Int. Appl. (2001), WO 01/00603 A1] in N,N-dimethylformamide in the presence of cesium carbonate to give [rac]-2-ethoxy-3-{4-[4-methyl-2-(4-trifluoromethyl-phenyl)-thiazol-5-ylmethoxy]-5,6,7,8-tetrahydro-naphthalen-1-yl}-propionic acid methyl ester, which was further saponified in analogy to the procedure described in example 1 e], to yield [rac]-2-ethoxy-3-{4-[4-methyl-2-(4-trifluoromethyl-phenyl)-thiazol-5-ylmethoxy]-5,6,7,8-tetrahydro-naphthalen-1-yl}-propionic acid as colorless solid.

MS: 518.3 (M−H)−.

Example 135

[rac]-2-Ethoxy-3-{4-[2-(4-trifluoromethyl-phenyl)-thiazol-5-ylmethoxy]-5,6,7,8-tetrahydro-naphthalen-1-yl}-propionic acid In analogy to the procedure described in 14 b], [rac]-2-ethoxy-3-(4-hydroxy-5,6,7,8-tetrahydro-naphthalen-1-yl)-propionic acid methyl ester (example 2 c]) was reacted with 5-chloromethyl-2-(4-trifluoromethyl-phenyl)-thiazole (prepared from [2-(4-trifluoromethyl-phenyl)-thiazol-5-yl]-methanol [PCT Int. Appl. (2002), WO 02/62774 A1] and methanesulfonyl chloride, triethylamine in dichloromethane) in N,N-dimethylformamide in the presence of cesium carbonate to give [rac]-2-ethoxy-3-{4-[2-(4-trifluoromethyl-phenyl)-thiazol-5-ylmethoxy]-5,6,7,8-tetrahydro-naphthalen-1-yl}-propionic acid methyl ester, which was further saponified in analogy to the procedure described in example 1 e], to yield [rac]-2-ethoxy-3-{4-[2-(4-trifluoromethyl-phenyl)-thiazol-5-ylmethoxy]-5,6,7,8-tetrahydro-naphthalen-1-yl}-propionic acid as light yellow solid.

MS: 504.2 (M−H)−.

Example 136 a] 4-[4-Methyl-2-(4-trifluoromethyl-phenyl)-thiazol]-5-ylmethoxy}-naphthalene-1-carbaldehyde 0.50 g of 4-hydroxy-naphthalene-1-carbaldehyde (2.90 mmol) was dissolved in 12 ml acetone and treated at 0° C. with 0.847 g of 5-chloromethyl-4-methyl-2-(4-trifluoromethyl-phenyl)-thiazole (1.0 eq.) and 1.04 g of $Cs_2CO_3$ (1.1 eq.) and then kept for 4 h at ambient temperature and for 1 h at 35° C. under stirring, when TLC indicated the disappearance of starting material. The bulk of the solvent was then removed i. V., the residue poured onto crashed ice/AcOEt, the organic layer washed with water, dried over sodium sulfate, and evaporated to dryness. Flash chromatography ($SiO_2$, hexane/AcOEt=7/3) yielded 0.882 g of the title compound as colorless crystals.

MS: 427.3 (M)+.

b] 3-Hydroxy-2-methoxy-3-{4-[4-methyl-2-(4-trifluoromethyl-phenyl)-thiazol-5-ylmethoxy]-naphthalen-1-yl}-propionic acid ethyl ester LDA-solution in THF was prepared according to standard procedure from 0.391 g of diisopropylamine (3.86 mmol) and 2.19 ml of 1.6 M nBuLi (hexane) in 15 ml of abs. THF at −10° C. After cooling to −75° C., 0.415 g of ethyl methoxyacetate (3.51 mmol), dissolved in 1 ml of THF, was added and stirring continued for 30 min. to complete enolate formation. 0.500 g of the above prepared 4-[4-methyl-2-(4-trifluoromethyl-phenyl)-thiazol-5-ylmethoxy]-naphthalene-1-carbaldehyde (1.17 mmol), dissolved in 8 ml of THF, was then added at −75° C. and the mixture kept for another 30 min. at this temperature. Pouring onto crashed ice/$NH_4Cl$, twofold extraction with AcOEt, washing with water, drying over sodium sulfate, and evaporation of the solvents, followed by flash chromatography ($SiO_2$, hexane/AcOEt=55/45) delivered 0.64 g of the title compound (syn/anti-isomers) as colorless oil.

MS: 546.3 (M+H)+.

c] 2-Methoxy-3-{4-[4-methyl-2-(4-trifluoromethyl-phenyl)-thiazol-5-ylmethoxy]-naphthalen-1-yl}-propionic acid ethyl ester 0.64 g of the above 3-hydroxy-2-methoxy-3-{4-[4-methyl-2-(4-trifluoromethyl-phenyl)-thiazol-5-ylmethoxy]-naphthalen-1-yl}-propionic acid ethyl ester (1.18 mmol) was dissolved in 5 ml of trifluoroacetic acid, treated at 0° C. with 1.87 ml of triethylsilane (10 eq.) and then kept for 3 h at 0° C. under vigorous stirring, when TLC indicated the disappearance of starting material. The reaction mixture was then poured onto crashed ice/AcOEt/$Na_2CO_3$, the organic layer washed with water (pH of aq. phase-8), dried over sodium sulfate, and evaporated to dryness. Flash chromatography ($SiO_2$, hexane/AcOEt=8/2) yielded 0.61 g of the title compound as colorless oil.

MS: 530.1 (M+H)+.

d] [rac]-2-Methoxy-3-{4-[4-methyl-2-(4-trifluoromethyl-phenyl)-thiazol-5-ylmethoxy]-naphthalen-1-yl}-propionic acid 0.61 g of the above prepared 2-methoxy-3-{4-[4-methyl-2-(4-trifluoromethyl-phenyl)-thiazol-5-ylmethoxy]-naphthalen-1-yl}-propionic acid ethyl ester (1.15 mmol) was dissolved in 5 ml of THF/EtOH=1/1, treated with 1.15 ml of 2N NaOH (2 eq.), and kept at ambient temperature for 1 h. The reaction mixture was then poured onto crashed ice/AcOEt/HCl dil., the organic layer washed with water, dried over sodium sulfate, and evaporated to dryness. Crystallization from hexane/AcOEt afforded finally 0.50 g of the title compound as white crystals of mp. 190–92° C.

MS: 500.2 (M–H)$^-$.

Example 137

[rac]-2-Ethoxy-3-{4-[4-methyl-2-(4-trifluoromethyl-phenyl)-thiazol-5-ylmethoxy]-naphthalen-1-yl}-propionic acid Was prepared in analogy to example 136, but using in step b] ethyl ethoxyacetate instead of ethyl methoxyacetate, as white crystals of mp. 186–88° C.

MS: 514.3 (M–H)$^-$.

Example 138

[rac]-2-Methoxy-3-{4-[4-methyl-2-(4-trifluoromethyl-phenyl)-thiazol-5-ylmethoxy]-benzo[b]thiophen-7-yl}-propionic acid Was prepared in analogy to example 136, but using in step a] 4-hydroxy-benzo[b]thiophene-7-carbaldehyde instead of 4-hydroxy-naphthalene-1-carbaldehyde, as white solid of mp. 140–42° dec.

MS: 506.2 (M–H)$^-$.

Example 139

[rac]-2-Ethoxy-3-{4-[4-methyl-2-(4-trifluoromethyl-phenyl)-thiazol-5-ylmethoxy]-benzo[b]thiophen-7-yl}-propionic acid Was prepared in analogy to example 137, but using in step a] 4-hydroxy-benzo[b]thiophene-7-carbaldehyde instead of 4-hydroxy-naphthalene-1-carbaldehyde, as white solid of mp. 178–79° C.

MS: 520.2 (M–H)$^-$.

Example 140

[rac]-2-Methoxy-3-(4-{2-methyl-1-[4-methyl-2-(4-trifluoromethyl-phenyl)-thiazol-5-yl]-propoxy}benzo[b]thiophen-7-yl)-propionic acid (1:1 diast. mixture)

Was prepared in analogy to example 138, but using in step a] 5-(1-chloro-2-methyl-propyl)-4-methyl-2-(4-trifluoromethyl-phenyl)-thiazole (prepared from [rac]-2-methyl-1-[4-methyl-2-(4-trifluoromethyl-phenyl)-thiazol-5-yl]-propan-1-ol [PCT Int. Appl. (2002), WO 02/062774 A1 in analogy to the procedure described in example 104 a]) instead of 5-chloromethyl-4-methyl-2-(4-trifluoromethyl-phenyl)-thiazole, as colorless oil.

MS: 548.2 (M–H)$^-$.

Example A

Tablets containing the following ingredients can be manufactured in a conventional manner

| Ingredients | Per tablet |
| --- | --- |
| Compound of formula (I) | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

Example C

Injection solutions can have the following composition:
Compound of formula (I) 3.0 mg

| | |
| --- | --- |
| Compound of formula (I) | 3.0 mg |
| Gelatine | 150.0 mg |
| Phenol | 4.7 mg |
| Sodium carbonate | to obtain a final pH of 7 |
| [0157] Water for injection solutions | [0158] ad 1.0 ml |

What is claimed is:

1. A compound of formula (I)

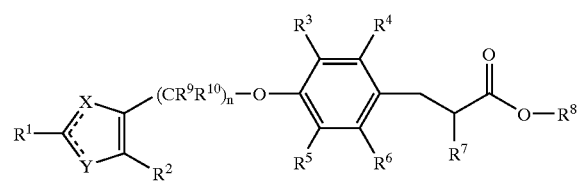

wherein
X is N and Y is S; or
X is S and Y is N;
R$^1$ is aryl or heteroaryl;
R$^2$ is hydrogen, lower-alkyl or fluoro-lower-alkyl;
R$^3$, R$^4$, R$^5$ and R$^6$ independently from each other are selected from hydrogen, hydroxy, lower-alkenyl, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, and lower-alkoxy-lower-alkoxy, wherein at least one of R$^3$, R$^4$, R$^5$ and R$^6$ is not hydrogen, or
R$^3$ and R$^4$ are bonded to each other to form a ring together with the carbon atoms to which they are attached, and R³ and R⁴ together are —CH=CH—S—, —S—CH=CH—, —CH=CH—O—, —O—CH=CH—, —CH=CH—CH=CH—, —(CH₂)₃₋₅—, —O—(CH₂)₂₋₃— or —(CH₂)₂₋₃—O—, and R⁵ and R⁶ are as defined above;

R⁷ is lower-alkyl, lower-alkoxy, lower-alkenyloxy, aryloxy or aryl-lower-alkoxy;

R⁸ is hydrogen or lower-alkyl;

R⁹ and R¹⁰ independently from each other are hydrogen, lower-alkyl, lower-alkenyl, cycloalkyl, phenyl or [1,3]dioxan-2-ethyl;

n is 1, 2 or 3;

or a pharmaceutically acceptable salt or a pharmaceutically acceptable ester thereof.

2. The compound according to claim 1, wherein R⁷ is lower-alkoxy, lower-alkenyloxy, aryloxy or aryl-lower-alkoxy-; R⁹ is hydrogen; and R¹⁰ is hydrogen.

3. The compound according to claim 1, wherein X is N and Y is S.

4. The compound according to claim 1, wherein R¹ is aryl.

5. The compound according to claim 4, wherein R¹ is phenyl or phenyl substituted with 1 to 3 substituents independently selected from the group consisting of lower-alkyl, lower-alkoxy, halogen and CF₃.

6. The compound according to claim 5, wherein R¹ is selected from phenyl, 4-isopropyl-phenyl, 4-chloro-phenyl, 4-trifluoromethyl-phenyl and 3,5-dimethoxy-phenyl.

7. The compound according to claim 1, wherein R² is lower-alkyl or hydrogen.

8. The compound according to claim 7, wherein R² is methyl or hydrogen.

9. The compound according to claim 1, wherein R³, R⁴, R⁵ and R⁶ independently from each other are selected from hydrogen, halogen, lower-alkyl and lower-alkoxy, wherein one or two of R³, R⁴, R⁵ and R⁶ are not hydrogen, or R³ and R⁴ are bonded to each other to form a ring together with the carbon atoms to which they are attached, and R³ and R⁴ together are —CH=CH—S—, —S—CH=CH—, —(CH₂)₃₋₅—, —CH=CH—CH=CH—, —O—CH=CH— or —O—(CH₂)₂₋₃—, and R⁵ and R⁶ are hydrogen.

10. The compound according to claim 9, wherein one or two of R³, R⁴, R⁵ and R⁶ independently from each other are selected from halogen, lower-alkyl and lower-alkoxy, and the others are hydrogen.

11. The compound according to claim 10, wherein R⁴ is methyl and R³, R⁵ and R⁶ are hydrogen.

12. The compound according to claim 9, wherein R⁵ and R⁶ are hydrogen; and R³ and R⁴ are bonded to each other to form a ring together with the carbon atoms to which they are attached, and R³ and R⁴ together are —CH=CH—S—, —S—CH=CH—, —(CH₂)₃₋₅—, —CH=CH—CH=CH—, —O—CH=CH—, or —O—(CH₂)₂₋₃—.

13. The compound according to claim 9, wherein R⁵ and R⁶ are hydrogen; and R³ and R⁴ are bonded to each other to form a ring together with the carbon atoms to which they are attached, and R³ and R⁴ together are —CH=CH—S—, —(CH₂)₃₋₅—, or —CH=CH—CH=CH—.

14. The compound according to claim 1, wherein R⁷ is lower-alkyl or lower-alkoxy.

15. The compound according to claim 14, wherein R⁷ is lower-alkyl which is ethyl or lower-alkoxy selected from ethoxy and isopropoxy.

16. The compound according to claim 1, wherein R⁸ is hydrogen.

17. The compound according to claim 1, wherein n is 1.

18. The compound according to claim 1, wherein n is 2.

19. The compound according to claim 1, wherein n is 3.

20. The compound according to claim 1, wherein R⁹ and R¹⁰ independently from each other are hydrogen, lower-alkyl or cycloalkyl.

21. The compound according to claim 20, wherein R⁹ and R¹⁰ are hydrogen.

22. The compound according to claim 1 selected from the group consisting of

[rac]-2-Ethoxy-3-{4-[2-(5-methyl-2-phenyl-thiazol-4-yl)-ethoxy]-benzo[b]thiophen-7-yl}-propionic acid,

[rac]-2-Ethoxy-3-{4-[2-(4-isopropyl-phenyl)-thiazol-4-ylmethoxy]-3-methyl-phenyl}-propionic acid,

[rac]-2-Ethoxy-3-{3-fluoro-4-[2-(4-trifluoromethyl-phenyl)-thiazol-4-ylmethoxy]-phenyl}-propionic acid,

[rac]-2-Ethoxy-3-{2-methyl-4-[2-(5-methyl-2-phenyl-thiazol-4-yl)-ethoxy]-phenyl}-propionic acid,

[rac]-3-{4-[2-(4-Chloro-phenyl)-thiazol-4-ylmethoxy]-2-methyl-phenyl}-2-ethoxy-propionic acid, (2S)-3-{4-[2-(4-Chloro-phenyl)-thiazol-4-ylmethoxy]-2-methyl-phenyl}-2-ethoxy-propionic acid, (2S)-3-{2-Chloro-4-[2-(4-chloro-phenyl)-thiazol-4-ylmethoxy]-phenyl}-2-ethoxy-propionic acid, and

[rac]-2-Ethoxy-3-(3-fluoro-4-{2-[2-(4-trifluoromethyl-phenyl)-thiazol-4-yl]-ethoxy}-phenyl)-propionic acid, or a pharmaceutically acceptable salt or a pharmaceutically acceptable ester thereof.

23. The compound according to claim 1 selected from the group consisting of

[rac]-2-Ethoxy-3-(3-fluoro-4-{3-[2-(4-isopropyl-phenyl)-thiazol-4-yl]-propoxy}-phenyl)-propionic acid;

[rac]-2-Ethoxy-3-{5-ethoxy-2-fluoro-4-[2-(4-isopropyl-phenyl)-thiazol-4-ylmethoxy]-phenyl}-propionic acid;

[rac]-3-(4-{2-[2-(3,5-Dimethoxy-phenyl)-5-methyl-thiazol-4-yl]-ethoxy}-benzo[b]thiophen-7-yl)-2-isopropoxy-propionic acid;

(S)-3-{4-[2-(4-Chloro-phenyl)-thiazol-4-ylmethoxy]-2-fluoro-phenyl}-2-ethoxy-propionic acid;

2-Ethoxy-3-(2-methyl-4-{1-[4-methyl-2-(4-trifluoromethyl-phenyl)-thiazol-5-yl]-ethoxy}-phenyl)-propionic acid;

2-Ethoxy-3-(2-methyl-4-{2-methyl-1-[4-methyl-2-(4-trifluoromethyl-phenyl)-thiazol-5-yl]-propoxy}-phenyl)-propionic acid;

2-(4-{Cyclopropyl-[4-methyl-2-(4-trifluoromethyl-phenyl)-thiazol-5-yl]-methoxy}-2-methyl-benzyl)-butyric acid;

[rac]-2-Ethoxy-3-{4-[2-(4-trifluoromethyl-phenyl)-thiazol-5-ylmethoxy]-5,6,7,8-tetrahydro-naphthalen-1-yl}-propionic acid; and

[rac]-2-Ethoxy-3-{4-[4-methyl-2-(4-trifluoromethyl-phenyl)-thiazol-5-ylmethoxy]-naphthalen-1-yl}-propionic acid;

or a pharmaceutically acceptable salt or a pharmaceutically acceptable ester thereof.

24. A pharmaceutical composition comprising a compound or a pharmaceutically acceptable salt according to claim 1 and a pharmaceutically acceptable carrier.

25. A method for the treatment of non-insulin dependent diabetes mellitus in a patient and in need of such treatment, which comprises administering a compound or pharmaceutically acceptable salt thereof according to claim 1 to said patient in an amount of from about 1 mg to about 1000 mg per day.

26. The method according to claim 25, wherein said amount administered is from about 1 mg to about 100 mg.

27. A compound of formula (Ia)

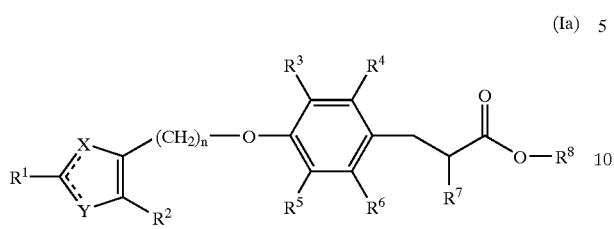

(Ia)

wherein
X is N and Y is S; or
X is S and Y is N;
$R^1$ is aryl or heteroaryl;
$R^2$ is hydrogen, lower-alkyl or fluoro-lower-alkyl;
$R^3$, $R^4$, $R^5$ and $R^6$ independently from each other are selected from hydrogen, hydroxy, lower-alkenyl, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, and lower-alkoxy-lower-alkoxy, wherein at least one of $R^3$, $R^4$, $R^5$ and $R^6$ is not hydrogen, or
$R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH—, —(CH$_2$)$_{3-5}$—, —O—(CH$_2$)$_{2-3}$— or —(CH$_2$)$_{2-3}$—O—, and $R^5$ and $R^6$ are as defined above;
$R^7$ is lower-alkoxy, lower-alkenyloxy, aryloxy or aryl-lower-alkoxy;
$R^8$ is hydrogen or lower-alkyl;
n is 1, 2 or 3;
or a pharmaceutically acceptable salt or a pharmaceutically acceptable ester thereof.

* * * * *